United States Patent
Dhingra et al.

(10) Patent No.: US 11,542,540 B2
(45) Date of Patent: Jan. 3, 2023

(54) CONTROL NUCLEIC ACIDS, AND COMPOSITIONS, KITS, AND USES THEREOF

(71) Applicant: LIFE TECHNOLOGIES CORPORATION, Carlsbad, CA (US)

(72) Inventors: Dalia Dhingra, San Francisco, CA (US); Richard Chien, Foster City, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 285 days.

(21) Appl. No.: 16/622,113

(22) PCT Filed: Jun. 12, 2018

(86) PCT No.: PCT/US2018/037090
§ 371 (c)(1),
(2) Date: Dec. 12, 2019

(87) PCT Pub. No.: WO2018/231818
PCT Pub. Date: Dec. 20, 2018

(65) Prior Publication Data
US 2020/0131563 A1    Apr. 30, 2020

Related U.S. Application Data

(60) Provisional application No. 62/521,141, filed on Jun. 16, 2017.

(51) Int. Cl.
*C12Q 1/68* (2018.01)
*C12Q 1/6806* (2018.01)
*C12Q 1/6869* (2018.01)

(52) U.S. Cl.
CPC .......... *C12Q 1/6806* (2013.01); *C12Q 1/6869* (2013.01)

(58) Field of Classification Search
CPC ............................ C12Q 1/6806; C12Q 1/6869
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 5,194,370 A | 3/1993 | Berninger et al. |
| 5,223,414 A | 6/1993 | Zarling et al. |
| 5,273,881 A | 12/1993 | Sena et al. |
| 5,399,414 A | 3/1995 | Matsuzaki et al. |
| 5,399,491 A | 3/1995 | Kacian et al. |
| 5,409,818 A | 4/1995 | Davey et al. |
| 5,670,316 A | 9/1997 | Sena et al. |
| 6,287,825 B1 | 9/2001 | Weissman et al. |
| 7,057,026 B2 | 6/2006 | Barnes et al. |
| 7,125,861 B2 | 10/2006 | Hebert |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,270,981 B2 | 9/2007 | Armes et al. |
| 7,399,590 B2 | 7/2008 | Piepenburg et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,435,561 B2 | 10/2008 | Piepenburg et al. |
| 7,541,444 B2 | 6/2009 | Milton et al. |
| 7,566,537 B2 | 7/2009 | Balasubramanian et al. |
| 7,592,435 B2 | 9/2009 | Milton et al. |
| 7,635,578 B2 | 12/2009 | Ju et al. |
| 7,666,598 B2 | 2/2010 | Piepenburg et al. |
| 7,713,698 B2 | 5/2010 | Ju et al. |
| 7,741,463 B2 | 6/2010 | Gormley et al. |
| 7,763,427 B2 | 7/2010 | Piepenburg et al. |
| 7,785,796 B2 | 8/2010 | Balasubramanian et al. |
| 7,790,869 B2 | 9/2010 | Ju et al. |
| 7,883,869 B2 | 2/2011 | Ju et al. |
| 7,948,015 B2 | 5/2011 | Rothberg et al. |
| 7,993,842 B2 | 8/2011 | McKernan et al. |
| 8,017,339 B2 | 9/2011 | Piepenburg et al. |
| 8,030,000 B2 | 10/2011 | Piepenburg et al. |
| 8,053,192 B2 | 11/2011 | Bignell et al. |
| 8,062,850 B2 | 11/2011 | Piepenburg et al. |
| 8,071,308 B2 | 12/2011 | Piepenburg et al. |
| 8,088,575 B2 | 1/2012 | Ju et al. |
| 8,158,346 B2 | 4/2012 | Balasubramanian et al. |
| 8,182,989 B2 | 5/2012 | Bignell et al. |

(Continued)

FOREIGN PATENT DOCUMENTS

| WO | 1988/010315 | 12/1988 |
| WO | 2006/084132 A2 | 8/2006 |

(Continued)

OTHER PUBLICATIONS

Stratagene catalog, p. 39 (Year: 1988).*
Bentley, David R et al. "Accurate whole human genome sequencing using reversible terminator chemistry." Nature vol. 456,7218 (2008): 53-9. doi:10.1038/nature07517.
David R Bentley, Whole-genome re-sequencing, Current Opinion in Genetics & Development, vol. 16, Issue 6, 2006, pp. 545-552.
DeAngelis MM, Wang DG, Hawkins TL. Solid-phase reversible immobilization for the isolation of PCR products. Nucleic Acids Res 1995;23(22):4742-4743. doi:10.1093/nar/23.22.4742.

(Continued)

*Primary Examiner* — Jezia Riley
(74) *Attorney, Agent, or Firm* — Workman Nydegger

(57) ABSTRACT

Provided are methods, as well as compositions, kits, and systems for preparing optimized control nucleic acids (polynucleotides) having reduce nucleic acid damage. Provided nucleic acid compositions provide reduced artifacts as compared to nucleic acid compositions prepared by conventional methods. Provided compositions are useful control in a variety of applications, including, but not limited to sequencing workflows to effectively monitor sensitivity, accuracy and/or precision of data.

22 Claims, 15 Drawing Sheets

Specification includes a Sequence Listing.

(56) References Cited

U.S. PATENT DOCUMENTS

| | | | |
|---|---|---|---|
| 8,208,712 | B2 | 6/2012 | Preil et al. |
| 8,262,900 | B2 | 9/2012 | Rothberg et al. |
| 8,399,188 | B2 | 3/2013 | Zhao |
| 8,420,319 | B2 | 4/2013 | Mikawa |
| 8,563,478 | B2 | 10/2013 | Gormley et al. |
| 8,776,573 | B2 | 7/2014 | Rearick et al. |
| 2008/0166727 | A1 | 7/2008 | Esfandyarpour et al. |
| 2009/0026082 | A1 | 1/2009 | Rothberg et al. |
| 2009/0127589 | A1 | 5/2009 | Rothberg et al. |
| 2010/0137143 | A1 | 6/2010 | Rothberg et al. |
| 2010/0197507 | A1 | 8/2010 | Rothberg et al. |
| 2010/0282617 | A1 | 11/2010 | Rothberg et al. |
| 2010/0300559 | A1 | 12/2010 | Schultz et al. |
| 2010/0300895 | A1 | 12/2010 | Nobile et al. |
| 2010/0301398 | A1 | 12/2010 | Rothberg et al. |
| 2013/0079232 | A1* | 3/2013 | Kain .................. C12Q 1/6869 435/6.1 |
| 2014/0155274 | A1 | 6/2014 | Xie et al. |
| 2014/0227705 | A1 | 8/2014 | Vogelstein et al. |
| 2015/0031559 | A1 | 1/2015 | Casbon et al. |
| 2015/0044687 | A1 | 2/2015 | Schmitt et al. |
| 2015/0133314 | A1 | 5/2015 | Shahbazian et al. |
| 2016/0362748 | A1 | 12/2016 | Mongan et al. |
| 2018/0305684 | A1* | 10/2018 | Andruzzi ........... C12N 15/1068 |

FOREIGN PATENT DOCUMENTS

| | | | |
|---|---|---|---|
| WO | 2013/181170 | A1 | 12/2013 |
| WO | 2015/100427 | A1 | 7/2015 |

OTHER PUBLICATIONS

Erik P. Anderson, Jonathan S. Daniels, Heng Yu, Miloslav Karhanek, Thomas H. Lee, Ronald W. Davis, Nader Pourmand, A system for multiplexed direct electrical detection of DNA synthesis, Sensors and Actuators B: Chemical, vol. 129, Issue 1, 2008, pp. 79-86.

Genetic disease detection and DNA amplification using cloned thermostable ligase, F Barany, Proceedings of the National Academy of Sciences Jan. 1991, 88 (1) 189-193.

PCR amplification of up to 35-kb DNA with high fidelity and high yield from lambda bacteriophage templates, W M Barnes, Proceedings of the National Academy of Sciences Mar. 1994, 91 (6) 2216-2220.

PCT Application No. PCT/US2016/023139, filed Mar. 18, 2016.

Pourmand N, Karhanek M, Persson HH, et al. Direct electrical detection of DNA synthesis. Proc Natl Acad Sci U S A. 2006;103(17):6466-6470.

S. Purushothaman, C. Toumazou and J. Georgiou, "Towards fast solid state DNA sequencing," 2002 IEEE International Symposium on Circuits and Systems. Proceedings (Cat. No. 02CH37353), Phoenix-Scottsdale, AZ, USA, 2002, pp. IV-IV.

Toshinari. Sakurai and Yuzuru. Husimi Analytical Chemistry 1992 64 (17), 1996-1997.

Transcription-based amplification system and detection of amplified human immunodeficiency virus type 1 with a bead-based sandwich hybridization format D Y Kwoh, G R Davis, K M Whitfield, H L Chappelle, L J DiMichele, T R Gingeras Proceedings of the National Academy of Sciences Feb. 1989, 86 (4) 1173-1177; DOI: 10.1073/pnas.86.4.1173.

UK Patent Application GB2461127, Filed Jun. 25, 2018.

International Search Report and Written Opinion issued in PCT/US2018/037090 dated Aug. 7, 2018.

Costello et al. "Discovery and Characterization of Artifactual Mutations in Deep Coverage Targeted Capture Sequencing Data Due to Oxidative DNA Damage During Sample Preparation" Nucleic Acids Research, vol. 41, No. 6, Jan. 7, 2013, pp. e67-e67.

Chen et al. "DNA Damage is a Pervasive Cause of Sequencing Errors, Directly Confounding Variant Identification" Science, vol. 355, No. 6326, Feb. 17, 2017, pp. 752-756.

Xavier et al. "Improved Methods of DNA Extraction from Human Spermatozoa That Mitigate Experimentally-Induced Dxidative DNA Damage" Plos One, vol. 13, No. 3, Mar. 26, 2018, p. e0195003.

* cited by examiner

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Synthetic DNA
      12:02 PM 6/11/2018
<220> FEATURE:
<221> NAME/KEY: misc_feature
<222> LOCATION: (1)..(9)
<223> OTHER INFORMATION: where "N" is A,T,C or G

<400> SEQUENCE: 1
nnnactnnnt ga                                                         12

<210> SEQ ID NO 2
<211> LENGTH: 12
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(9)
<223> OTHER INFORMATION: where "N" is A,T,C or G

<400> SEQUENCE: 2
nnnactnnnt gc                                                         12

<210> SEQ ID NO 3
<211> LENGTH: 13
<212> TYPE: DNA
<213> ORGANISM: Homo sapiens

<400> SEQUENCE: 3
agcatacgtg atg                                                        13
```

CONTROL NUCLEIC ACIDS, AND COMPOSITIONS, KITS, AND USES THEREOF

This application claims priority to PCT Application No. PCT/US2018/037090, filed Jun. 12, 2018, entitled "CONTROL NUCLEIC ACIDS, AND COMPOSTIONS, KITS, AND USES THEREOF" which claims s the benefit of priority under 35 U.S.C. § 119 to U.S. Provisional Application No. 62/521,141, filed Jun. 16, 2017, entitle "CONTROL NUCLEIC ACIDS, AND COMPOSTIONS, KITS, AND USES THEREOF", the disclosure of the aforementioned applications are incorporated by reference in their entireties.

Throughout this application various publications, patents, and/or patent applications are referenced. The disclosures of the publications, patents and/or patent applications in their entireties are hereby incorporated by reference into this application in order to more fully describe the state of the art to which this invention pertains.

SEQUENCE LISTING

This application hereby incorporates by reference the material of the electronic Sequence Listing filed concurrently herewith. The material in the electronic Sequence Listing is submitted as a text (.txt) file entitled "LT01268PCT_SequenceListing_ST25.txt" created on 11 Jun. 2018 which has a file size of 2 KB, and is herein incorporated by reference in its entirety.

FIELD OF THE INVENTION

In some embodiments, provided are methods, as well as related compositions, kits, and systems, for reducing nucleic acid damage during fragmentation by fragmenting nucleic acids in the presence of nucleic acid damage-mitigating reagents and/or chelating reagents.

SUMMARY

In one aspect of the invention, methods are provided for preparing nucleic acids having reduced damage comprising providing at least a first plurality of polynucleotides, at least one nucleic acid damage mitigating reagent, and optionally at least one chelating reagent; and fragmenting the polynucleotides to generate a plurality of nucleic acid fragments. In some embodiments, the damage-mitigating reagent is selected from a group consisting of 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; indole-3-acetic acid; insulin chain B fragment; water-soluble chitsan-indole-3-propionic acid conjugates (e.g., see Hebert, U.S. Pat. No. 7,125,861); melatonin (and its derivatives); monoethanolamine; carnitine; acetylcarnitine; β-hydroxy-γ(trimethylammonio)butyrate hydrochloride (DL-carnitine); beta-mercaptoethanol; sodium azide; glutathione; nitrous oxide; superoxide dismutase; glucose oxidase/catalase (GO/Cat); oxidase/peroxidase enzyme systems (e.g., glucose oxidases, alcohol oxidases, cholesterol oxidases, lactate oxidases, pyruvate oxidases, and xanthine oxidases); horseradish peroxidase (HRP); glutathione peroxidase; protocatachaute 3,4 dioxygenase (PCD); ergothioneine; methionine; cysteine; beta-dimethyl cysteine (penicillamine); mercaptopropionylglycine; sodium 2-mercaptoethanesulfonate (MESNA); glutathione; dithiothreitol; N-acetyl cysteine; captopril; imidazole; lycopene; carotene (e.g., alpha-, beta-, and gamma-carotene, and analogs thereof); antheraxanthin; astaxanthin; canthaxanthin; neurosporene; rhodopsin; bixin; norbixin; zeaxanthin; lutein; bilirubin; biliverdin; tocopherols; polyene dialdehydes; vitamin E (e.g., alpha-tocopheryl succinate and its analogs); vitamin B6 (pyridoxine 1 and its derivatives); hydrazine (N2H4); sodium sulfite (Na2S03); hydroxylamine; glutathione; N-acetylcysteine; histidine; tryptophan; Trolox (6-hydroxy-2,5,7,8-tetramethylchroman-2-carboxylic acid and its analogs U-78715F and WIN62079); soluble forms of vitamin E; ascorbic acid (or ascorbate); butylated hydroxytoluene (BTH); nPG (n-propyl gallate); DABCO (1,4-diazabicyclo[2.2.2]octane; TCEP (tris(2-carboxyethyl) phosphine; 2-mercaptoethylamine (MEA); thioglycerol; and/or hydroquinone; or spermidine. In some embodiments, the chelating reagent is selected from a group consisting of an aminopolycarboxylic acid, a phonsphonic acid, EDTA, EDDHA, EDDS, EDTMP and EGTA. In certain embodiments, methods are carried out in a first and a second reaction mixture, each comprising a first and a second plurality of nucleotides, respectively, as well as at least one nucleic acid damage mitigating reagent and at least one chelating agent; and fragmenting the first and optionally fragmenting the second plurality of nucleotides to generate a first and a optionally a second plurality of nucleic acid fragments having reduced damage. In particular embodiments, nucleotides comprising the first and/or second plurality of nucleotides are each separately selected from DNA or RNA or a mixture of DNA and RNA In other aspects of the invention, provided are nucleic acids and compositions thereof prepared according to the methods of the invention; kits comprising nucleic acids prepared according to the methods of the instant invention; as well as systems for carrying out methods provided herein, wherein the system comprises a plurality of nucleotides, at least one nucleic acid damage mitigating reagent and optionally at least one chelating reagent as provided herein. Additionally, applications of the provided methods, as well as methods of use of the instant compositions, kits, and systems are provided herein.

BRIEF DESCRIPTION OF THE DRAWINGS

FIG. 1A depicts results of standards detected in a control sample prepared, tagged and sequenced as described in Examples 1 and 2; FIG. 1B depicts results of standards detected in a control sample prepared, tagged and sequenced as described in Examples 1 and 2.

FIGS. 2A-2D depict results of detected allelic frequencies for control DNA prepared by methods described in the teachings herein, uniquely tagged using a lung primer panel (Oncomine® lung cfDNA Assay kit, catalog No. A31149 from Thermo Fisher Scientific), and sequenced using a massively parallel sequencing platform. FIG. 2A depicts results of standards detected in a control sample prepared, tagged and sequenced as described in Examples 1 and 2; FIG. 2B depicts results of standards detected in a control sample prepared, tagged and sequenced as described in Examples 1 and 2; FIG. 2C depicts results of standards detected in a control sample prepared, tagged and sequences as described in Examples 1 and 2; and FIG. 2D depicts results of standards detected in a control sample prepared, tagged and sequenced as described in Examples 1 and 2.

FIG. 3A shows A variant mean counts. FIG. 3B shows C>A variant mean counts. FIG. 3C shows C>T variant mean counts. FIG. 3D shows G>A variant mean counts. FIG. 3E shows G>T variant mean counts. FIG. 3F shows T>C variant mean counts. FIG. 3G shows T>G variant mean counts.

FIG. 4A shows the level of false positive sequencing reads from control DNA prepared by shearing Acrometrix DNA.

FIG. 5A shows the level of false positive sequencing reads from control DNA prepared by shearing Acrometrix DNA.

FIG. 6A shows the level of false positive sequencing reads from control DNA prepared by shearing Acrometrix DNA.

DESCRIPTION OF THE INVENTION

Figure 1A:
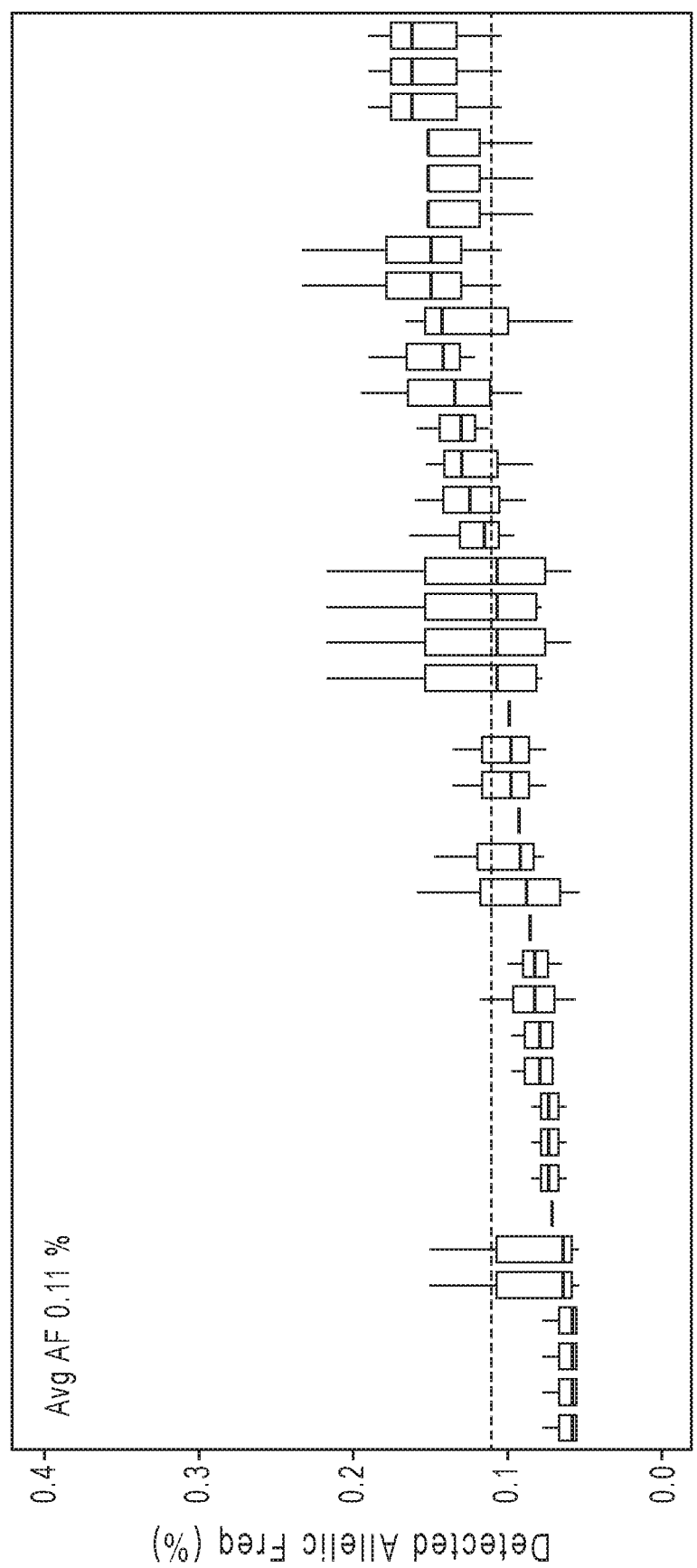
FIGS. 1A-1C depict results of detected allelic frequencies for control DNA prepared by methods described in the teachings herein, uniquely tagged using a colon primer panel (Oncomine® colon cfDNA Assay kit, catalog No. A31182 from Thermo Fisher Scientific), and sequenced using a massively parallel sequencing platform.

In some embodiments, provided are control nucleic acids, comprises: (a) a first plurality of nucleic acid fragments from a first plurality of polynucleotides which have been fragmented using mechanical force in the presence of a nucleic acid damage-mitigating reagent and a chelating reagent to generate the first plurality of nucleic acid fragments having reduced damage compared to a plurality of polynucleotides that are fragmented in the absence of the nucleic acid damage-mitigating regent and the chelating reagent; and optionally (b) a second plurality of nucleic acid fragments from a second plurality of polynucleotides which have been fragmented using mechanical force in the presence of a nucleic acid damage-mitigating reagent and a chelating reagent to generate the second plurality of nucleic acid fragments having reduced damage compared to a plurality of polynucleotides that are fragmented in the absence of the nucleic acid damage-mitigating regent and the chelating reagent. In some embodiments, the damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid. In some embodiments, the chelating reagent is selected from a group consisting of EDTA, EDDHA, EDDS, EDTMP and EGTA. In some embodiments, the reduced damage of the first plurality of nucleic acid fragments and the second plurality of nucleic acid fragments comprises reduced transitions which are selected from a group consisting of C>T, T>C, A>G, and G>A. In some embodiments, the reduced damage of the first plurality of nucleic acid fragments and the second plurality of nucleic acid fragments comprises reduced transversions which are selected from a group consisting of, A>T, T>A, C>T, T>C, A>C, C>A, G>T and T>G. In some embodiments, the mechanical force comprises: acoustic force, nebulizing force, sonication force, cavitation force or shearing force. In some embodiments, the first plurality of nucleic fragments comprise a known amount of at least one wild-type target sequence. In some embodiments, at least one wild-type target sequence is present in the first plurality of nucleic acid fragments at a concentration range of 10%-$10^{-8}$. In some embodiments, the first plurality of nucleic fragments comprise a known amount of at least one variant target sequence. In some embodiments, at least one variant target sequence is present in the first plurality of nucleic acid fragments at a concentration range of 10%-$10^{-8}$. The first plurality of polynucleotides comprises DNA or RNA. In some embodiments, the second plurality of nucleic fragments comprise a known amount of at least one wild-type target sequence. In some embodiments, at least one wild-type target sequence is present in the second plurality of nucleic acid fragments at a concentration range of 10%-$10^{-8}$. In some embodiments, the second plurality of nucleic fragments comprise a known amount of at least one variant target sequence. In some embodiments, at least one variant target sequence is present in the second plurality of nucleic acid fragments at a concentration range of 10%-$10^{-8}$. The second plurality of polynucleotides comprises DNA or RNA. In some embodiments, provided are kits comprising any of the control nucleic acids described herein.

In some embodiments, provided are systems, comprising: (a) a first plurality of polynucleotides and optionally a second plurality of polynucleotides; (b) at least one damage-mitigating reagent; and (c) at least one chelating reagent, wherein the damage-mitigating reagent and the chelating reagent reduces nucleic acid damage compared to a plurality of polynucleotides that are fragmented in the absence of the nucleic acid damage-mitigating regent and the chelating reagent. In some embodiments, the damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L- alanine, indole lactic acid, and indole-3-acetic acid. In some embodiments, the chelating reagent is selected from a group consisting of EDTA, EDDHA, EDDS, EDTMP and EGTA. In some embodiments, the reduced nucleic acid damage of the first plurality of polynucleotides and the second plurality of polynucleotides comprise reduced transitions which are selected from a group consisting of C>T, T>C, A>G, and G>A. In some embodiments, the reduced nucleic acid damage of the first plurality of polynucleotides and the second plurality of polynucleotides comprise reduced transversions which are selected from a group consisting of, A>T, T>A, C>T, T>C, A>C, C>A, G>T and T>G. In some embodiments, the first plurality of polynucleotides comprise a known amount of at least one wild-type target sequence. In some embodiments, the at least one wild-type target sequence is present in the first plurality of polynucleotides at a concentration range of $10\%$-$10^{-8}$. In some embodiments, the first plurality of polynucleotides comprise a known amount of at least one variant target sequence. In some embodiments, the at least one variant target sequence is present in the first plurality of polynucleotides at a concentration range of $10\%$-$10^{-8}$. The first plurality of polynucleotides comprises DNA or RNA. In some embodiments, the second plurality of polynucleotides comprise a known amount of at least one wild-type target sequence. In some embodiments, at least one wild-type target sequence is present in the second plurality of polynucleotides at a concentration range of $10\%$-$10^{-8}$. In some embodiments, the second plurality of polynucleotides comprise a known amount of at least one variant target sequence. In some embodiments, at least one variant target sequence is present in the second plurality of polynucleotides at a concentration range of $10\%$-$10^{-8}$. The second plurality of polynucleotides comprise DNA or RNA. In some embodiments, provided are kits comprising any of the systems described herein.

In some embodiments, provided are methods for preparing control nucleic acids by separately fragmenting different pluralities of polynucleotides, comprising: (a) providing a first single reaction mixture containing (i) a first plurality of polynucleotides, (ii) at least one nucleic acid damage-mitigating reagent, and (iii) at least one chelating reagent; (b) fragmenting the first plurality of polynucleotides to generate a first plurality of nucleic acid fragments having reduced damage compared to a plurality of polynucleotides that are fragmented in the absence of the nucleic acid damage-mitigating regent and the chelating reagent; (c) optionally providing a second single reaction mixture containing (i) a second plurality of polynucleotides, (ii) at least one nucleic acid damage-mitigating reagent, and (iii) at least one chelating reagent; and (d) optionally fragmenting the second plurality of polynucleotides to generate a second plurality of nucleic acid fragments having reduced damage compared to a plurality of polynucleotides that are fragmented in the absence of the nucleic acid damage-mitigating regent and the chelating reagent. In some embodiments, the damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid. In some embodiments, the chelating reagent is selected from a group consisting of EDTA, EDDHA, EDDS, EDTMP and EGTA. In some embodiments, the reduced damage of the first plurality of nucleic acid fragments and the second plurality of nucleic acid fragments comprises reduced transitions which are selected from a group consisting of C>T, T>C, A>G, and G>A. In some embodiments, the reduced damage of the first plurality of nucleic acid fragments and the second plurality of nucleic acid fragments comprises reduced transversions which are selected from a group consisting of, A>T, T>A, C>T, T>C, A>C, C>A, G>T and T>G. In some embodiments, the fragmenting is conducted with mechanical force which comprises: acoustic force, nebulizing force, sonication force, cavitation force or shearing force. In some embodiments, the first plurality of polynucleotides or the first plurality of nucleic fragments comprise a known amount of at least one wild-type target sequence, which includes a first wild-type target sequence. In some embodiments, at least one wild-type target sequence is present in the first plurality of polynucleotides or the first plurality of nucleic acid fragments at a concentration range of $10\%$-$10^{-8}$. In some embodiments, the first plurality of polynucleotides or the first plurality of nucleic fragments comprise a known amount of at least one variant target sequence, which includes a first variant target sequence. In some embodiments, at least one variant target sequence is present in the first plurality of polynucleotides or the first plurality of nucleic acid fragments at a concentration range of $10\%$-$10^{-8}$. The first plurality of polynucleotides comprise DNA or RNA. In some embodiments, the second plurality of polynucleotides or the second plurality of nucleic fragments comprise a known amount of at least one wild-type target sequence, which includes a second wild-type target sequence. In some embodiments, at least one wild-type target sequence is present in the second plurality of polynucleotides or the second plurality of nucleic acid fragments at a concentration range of $10\%$-$10^{-8}$. In some embodiments, the second plurality of polynucleotides or the second plurality of nucleic fragments comprise a known amount of at least one variant target sequence, which includes a second variant target sequence. In some embodiments, at least one variant target sequence is present in the second plurality of polynucleotides or the second plurality of nucleic acid fragments at a concentration range of $10\%$-$10^{-8}$. In some embodiments, the second plurality of polynucleotides comprise DNA or RNA. In some embodiments, the method further comprises: (a) diluting the first plurality of nucleic acid fragments to obtain a desired concentration of at least one wild-type target sequence; and/or (b) diluting the second plurality of nucleic acid fragments to obtain a desired concentration of at least one wild-type target sequence. In some embodiments, the method further comprises: (a) diluting the first plurality of nucleic acid fragments to obtain a desired concentration of at least one variant target sequence; and/or (b) diluting the second plurality of nucleic acid fragments to obtain a desired concentration of at least one variant target sequence. In some embodiments, the method further comprises: mixing together the first plurality of nucleic acid fragments and the second plurality of nucleic acid fragments to form a mixture of fragmented nucleic acids. In some embodiments, the mixture of fragmented nucleic acids comprises a known amount of at least one wild-type target sequence from the first plurality of nucleic fragments. In some embodiments, at least one wild-type target sequence is present in the mixture of fragmented nucleic acids at a concentration range of $10\%$-$10^{-8}$. In some embodiments, the mixture of fragmented nucleic acids comprises a known amount of at least one variant target sequence from the first plurality of nucleic fragments. In some embodiments, at least one variant target sequence is present in the mixture of fragmented nucleic acids at a concentration range of $10\%$-$10^{-8}$. In some embodiments, the mixture of fragmented nucleic acids comprises a known amount of at least one wild-type target sequence from the second plurality of nucleic fragments. In some embodiments, at least one wild-type target sequence is present in the mixture of fragmented nucleic acids at a concentration range of 10%-$10^{-8}$. In some embodiments, the mixture of fragmented nucleic acids comprises a known amount of at least one variant target sequence from the second plurality of nucleic fragments. In some embodiments, at least one variant target sequence is present in the mixture of fragmented nucleic acids at a concentration range of 10%-$10^{-8}$.

In some embodiments, provided are methods for preparing control nucleic acids from a mixture of first and second pluralities of polynucleotides, comprising: (a) providing a single reaction mixture containing (i) a first plurality of polynucleotides, (ii) a second plurality of polynucleotides, (iii) at least one nucleic acid damage-mitigating, and (iv) at least one chelating reagent; and (b) fragmenting the first and second plurality of polynucleotides to generate a mixture of first plurality of nucleic acid fragments and second plurality of nucleic acid fragments having reduced damage compared to a plurality of polynucleotides that are fragmented in the absence of the nucleic acid damage-mitigating regent and the chelating reagent. In some embodiments, the damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid. In some embodiments, the chelating reagent is selected from a group consisting of EDTA, EDDHA, EDDS, EDTMP and EGTA. In some embodiments, the reduced damage of the first plurality of nucleic acid fragments and the second plurality of nucleic acid fragments comprises reduced transitions which are selected from a group consisting of C>T, T>C, A>G, and G>A. In some embodiments, the reduced damage of the first plurality of nucleic acid fragments and the second plurality of nucleic acid fragments comprises reduced transversions which are selected from a group consisting of, A>T, T>A, C>T, T>C, A>C, C>A, G>T and T>G. In some embodiments, the fragmenting is conducted with mechanical force, which comprises: acoustic force, nebulizing force, sonication force, cavitation force or shearing force. In some embodiments, the first plurality of polynucleotides or the first plurality of nucleic fragments comprise a known amount of at least one wild-type target sequence, which includes a first wild-type target sequence. In some embodiments, at least one wild-type target sequence is present in the first plurality of polynucleotides or the first plurality of nucleic acid fragments at a concentration range of 10%-$10^{-8}$. In some embodiments, the first plurality of polynucleotides or the first plurality of nucleic fragments comprise a known amount of at least one variant target sequence, which includes a first variant target sequence. In some embodiments, at least one variant target sequence is present in the first plurality of polynucleotides or the first plurality of nucleic acid fragments at a concentration range of 10%-$10^{-8}$. The first plurality of polynucleotides comprise DNA or RNA. In some embodiments, the second plurality of polynucleotides or the second plurality of nucleic fragments comprise a known amount of at least one wild-type target sequence, which includes a second wild-type target sequence. In some embodiments, at least one wild-type target sequence is present in the second plurality of polynucleotides or the second plurality of nucleic acid fragments at a concentration range of 10%-$10^{-8}$. In some embodiments, the second plurality of polynucleotides or the second plurality of nucleic fragments comprise a known amount of at least one variant target sequence, which includes a second variant target sequence. In some embodiments, at least one variant target sequence is present in the second plurality of polynucleotides or the second plurality of nucleic acid fragments at a concentration range of 10%-$10^{-8}$. In some embodiments, the second plurality of polynucleotides comprise DNA or RNA. In some embodiments, the method further comprises: diluting the mixture of first plurality of nucleic acid fragments and second plurality of nucleic acid fragments to obtain a desired concentration of at least one wild-type target sequence. In some embodiments, the method further comprises: diluting the mixture of first plurality of nucleic acid fragments and second plurality of nucleic acid fragments to obtain a desired concentration of at least one variant target sequence.

In some embodiments, provided are methods for preparing the control nucleic acids by separately fragmenting different polynucleotide or by fragmenting a mixture of first and second pluralities of polynucleotides, where the control nucleic acids can be subjected to nucleic acid manipulation procedures to generate a standard nucleic acid library. In some embodiments, the methods further comprise: generating end-repaired fragmented nucleic acids by converting a 5' overhang end or a 3' overhang end of the first plurality of nucleic acid fragments and/or the second plurality of nucleic acid fragments to generate blunt-ended nucleic acid fragments. In some embodiments, the methods further comprise: generating end-repaired fragmented nucleic acids by adding non-template tails to the 3' ends of the first plurality of nucleic acid fragments and/or the second plurality of nucleic acid fragments to generate tailed nucleic acid fragments. In some embodiments, the methods further comprise: joining one end or both ends of the first plurality of nucleic acid fragments and/or the second plurality of nucleic acid fragments to an oligonucleotide adaptor to generate adaptor-joined nucleic acid fragments. In some embodiments, the oligonucleotide adaptor is joined to one or both ends of the end-repaired fragmented nucleic acids by ligation or primer extension or PCR amplification. In some embodiments, the methods further comprise: amplifying the adaptor-joined nucleic acid fragments to generate nucleic acid amplicons. In some embodiments, the methods further comprise: sequencing the nucleic acid amplicons. In some embodiments, the sequencing comprises massively parallel sequencing. In some embodiments, the sequencing generates no more than 10 false positive sequencing reads which comprise fragmentation-induced nucleic acid transitions which are selected from a group consisting of C>T, T>C, A>G, and G>A. In some embodiments, the sequencing generates no more than 10 false positive sequencing reads which comprise fragmentation-induced nucleic acid transversions which are selected from a group consisting of, A>T, T>A, C>T, T>C, A>C, C>A, G>T and T>G.

In some embodiments, provided are methods for preparing the control nucleic acids by separately fragmenting different polynucleotide or by fragmenting a mixture of first and second pluralities of polynucleotides, where the control nucleic acids can be subjected to nucleic acid manipulation procedures to generate a molecular tagged nucleic acid library. In some embodiments, the methods further comprise: (a) providing single reaction mixture comprising the nucleic acid fragments which includes fragments from the first plurality of polynucleotides and optionally from the second plurality of polynucleotides; (b) appending an oligonucleotide adaptor to one end or both ends of the nucleic acid fragments to generate a plurality of tagged nucleic acids. In some embodiments, the oligonucleotide adaptor includes (i) at least one or any combination of a universal sequence, including an amplification primer sequence, a sequencing primer sequence, a capture primer sequence and/or a cleavable site. In some embodiments, the oligonucleotide adaptor further comprises: at least one unique tag sequence from a repertoire of different unique tag sequences. In some embodiments, the oligonucleotide adaptor further comprises: (i) at least one unique tag sequence from a repertoire of different unique tag sequences, and (ii) at least one fixed tag sequence that is the same sequence in all of the oligonucleotide adaptors. In some embodiments, at least one unique tag sequence comprises a random or degenerate sequence. In some embodiments, at least one unique tag sequence is flanked on both sides by a fixed sequence, or wherein the fixed sequence is flanked on both sides by a unique tag sequence. In some embodiments, the oligonucleotide adaptor comprises two or more different unique tag sequences alternating with two or more fixed tag sequences. In some embodiments, the oligonucleotide adaptor comprises the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10. In some embodiments, the oligonucleotide adaptor comprises a double-stranded linear adaptor, a stem-looped adaptor or a Y-shaped adaptor. In some embodiments, the oligonucleotide adaptor is appended to the nucleic acid fragments by ligation. In some embodiments, the oligonucleotide adaptor comprises a single-stranded primer having a 3' region that specifically binds a target sequence in a nucleic acid fragment and a 5' region including a unique tag sequence. In some embodiments, the oligonucleotide adaptor is appended to the nucleic acid fragments by primer extension or PCR amplification. In some embodiments, the method further comprises: amplifying the plurality of tagged nucleic acids to generate a plurality of tagged nucleic acid amplicons. In some embodiments, the method further comprises: sequencing the plurality of tagged nucleic acid amplicons to generate a plurality of sequencing reads. In some embodiments, the method further comprises: determining the first wild-type target sequence is present in the nucleic acid fragments at an abundance level of $10\%$-$10^{-8}\%$; and optionally determining the second wild-type target sequence is present in the nucleic acid fragments at an abundance level of $10\%$-$10^{-8}\%$. In some embodiments, the method further comprises: determining the first variant target sequence is present in the nucleic acid fragments at an abundance level of $10\%$-$10^{-8}\%$; and optionally determining the second variant target sequence is present in the nucleic acid fragments at an abundance level of $10\%$-$10^{-8}\%$. In some embodiments, the sequencing generates no more than 10 false positive sequencing reads which comprise fragmentation-induced nucleic acid transitions which are selected from a group consisting of C>T, T>C, A>G, and G>A. In some embodiments, the sequencing generates no more than 10 false positive sequencing reads which comprise fragmentation-induced nucleic acid transversions which are selected from a group consisting of, A>T, T>A, C>T, T>C, A>C, C>A, G>T and T>G.

In some embodiments, provided are methods for sequencing the standard nucleic acid library or the molecular tagged nucleic acid library, wherein the sequencing comprises: (a) depositing the adaptor-joined nucleic acid fragments, or the nucleic acid amplicons, onto an array of reaction chambers, wherein at least one reaction chamber is capacitively coupled to a field effect transistor (FET) that detects byproducts of nucleotide incorporations. In some embodiments, the sequencing method further comprises: (b) contacting the adaptor-joined nucleic acid fragments, or the nucleic acid amplicons with a plurality of polymerases; (c) flowing a plurality of nucleotides onto the array of reaction chambers under conditions suitable for nucleotide incorporation wherein the plurality of nucleotides comprises at least one type of un-labeled non-terminator nucleotide; (d) detecting incorporation of the at least one type of un-labeled non-terminator nucleotide by detecting byproducts of nucleotide incorporation; and (e) identifying the incorporated un-labeled non-terminator nucleotide. In some embodiments, the byproducts of nucleotide incorporations comprise: pyrophosphates, hydrogen ions, protons, charge transfer or heat.

In some embodiments, provided are methods for sequencing the standard nucleic acid library or the molecular tagged nucleic acid library, wherein the sequencing comprises: (a) depositing the adaptor-joined nucleic acid fragments, or the nucleic acid amplicons, onto a planar support or an array of reaction chambers. In some embodiments, the method further comprises: (b) contacting the adaptor-joined nucleic acid fragments, or the nucleic acid amplicons with a plurality of polymerases; (c) flowing a plurality of nucleotides onto the planar support or the array of reaction chambers under conditions suitable for nucleotide incorporation, wherein at the plurality of nucleotides comprises at least one type of fluorescently labeled nucleotides; (d) detecting incorporation of the fluorescently labeled nucleotides; and (e) identifying incorporation of the fluorescently labeled nucleotides. In some embodiments, the plurality of nucleotides comprises at least one type of a terminator nucleotide having a blocking moiety linked to the 2' or 3' sugar position of the terminator nucleotide.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is explicitly or implicitly set forth herein that is contrary to or otherwise inconsistent with any definition set forth in the patents, patent applications, published applications, and other publications that are herein incorporated by reference, the definition and/or description set forth herein prevails over the definition that is incorporated by reference.

This description and exemplary embodiments should not be taken as limiting. For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

A typical next generation nucleic acid workflow includes numerous steps including library preparation, massively parallel sequencing, and data analysis. It is important that a proper control sample be included to detect any failures of that may have occurred throughout the workflow, and to determine the level of sensitivity, accuracy and precision of data generated using the workflow. An effective control should simulate size and quantity of input test nucleic acids; and when a workflow is employed to detect low abundance sequence(s)-of-interest, an effective control should also mimic a similar abundance level of the sequences-of-interest in the test sample to effectively validate that a workflow is capable of accurately detecting and analyzing low abundance species. In a similar manner, when a workflow is employed to detect copy number variation of sequences, an effective control should mimic a similar copy number variation ratio of the sequence(s)-of-interest. For example, a dilution series of an effective control sample is useful for establishing the lower end of detection (e.g., sensitivity) of a workflow. Current controls and methods for preparing controls yield nucleic acid samples can convey structurally damaged nucleic acids resulting in artifact sequence mutations. Due to such artifacts that may not be present in an input samples of interest (or not present at the abundance levels in the input sample), currently available control samples, and those prepared with current methodology, may not serve as a dependable control standard(s). This issue is particularly problematic in deep analyses, looking at low frequency target sequences.

Nucleic acid compositions, as well as systems, kits and methods, provided in the present teachings include improved control nucleic acids (and methods for generating the improved control nucleic acids). In particular, provided nucleic acid compositions have reduced amount of structurally damaged nucleic acids and thus generate reduced amount of artifacts in sequence analyses as compared to current available counterparts. Nucleic acids prepared with the methods described in the teachings herein are useful as an improved control sample/control nucleic acid(s) over others those presently available.

Nucleic acid compositions, as well as related systems, kits and methods, described in the present teachings provide improved control nucleic acid samples compared to pre-fragmented synthetic mixtures of diverse DNA sequences which are commercially-available, including for example Acrometrix Oncology Hotspot Control (from Thermo Fisher Scientific, catalog No. 969056) which is described in U.S. published application No. 2015/0133314, incorporated herein by reference in its entirety.

Preparing a nucleic acid library employs numerous steps, many of which are known to damage the nucleic acid resulting in reduced yield of intact material or altered nucleotide sequences. In a typical nucleic acid library preparation workflow, nucleic acids are manipulated e.g., by sample-handling, fragmentation, end-repairing, internal-repairing, end-tailing, size-selection, adaptor-joining, nick-translation, amplification, quantification and/or sequencing.

Provided herein are methods, as well as related compositions, kits, and systems, for reducing nucleic acid damage during fragmentation and nucleic acid preparation. Nucleic acids prepared in this manner have reduced artifact base mutations and/or reduced structural damage, compared to nucleic acids that are prepared without employing the nucleic acid damage-mitigating reagents and/or chelating reagents described herein. In particular aspects, nucleic acids prepared in this manner can be used as an effective control nucleic acid in deep analyses, e.g., a massively parallel sequencing workflow, to monitor the sensitivity, accuracy and/or precision of a data analysis.

Thus, provided are methods, as well as related compositions, kits, and systems, for reducing nucleic acid damage, by fragmenting nucleic acids in the presence of at least one or a combination of a nucleic acid damage-mitigating reagent (e.g., antioxidant reagents, free radical scavengers, oxygen scavenger, triple quenchers and/or reagents that reduce fading of fluorescent compounds) and/or at least one or any combination of a chelating reagent, to generate fragmented nucleic acids that exhibit reduced damage compared to nucleic acids that are fragmented in the absence of a nucleic acid damage-mitigating regent and/or a chelating reagent.

In some embodiments, input nucleic acids (polynucleotides) for preparing control nucleic acids contain at least one known wild-type and/or at least one known variant sequence, wherein input nucleic acids are fragmented in the presence of nucleic acid damage-mitigating reagents and/or chelating reagents, to generate nucleic acid fragments having a known wild-type and known variant sequences with reduced amount of structurally damaged nucleic acids and reduced amount of artifact sequence mutations (intact nucleic acid fragments), compared to nucleic acids that are fragmented in the absence of a nucleic acid damage-mitigating regent and/or a chelating reagent.

In some embodiments, control nucleic acids having known wild-type, and control nucleic acids having the known variant sequences, both of which are prepared by any of the methods described herein, are mixed together to prepare a control nucleic acid having a known concentration of the variant sequence and/or the known wild-type sequence. In some embodiments, the final concentration of the at least one sequence-of-interest (e.g., variant or the wild-type sequence-of-interest) is in a range of about 0.00001%-10%, or about $10^{-8}$-$10^{-1}$, or about $10^{-1}$ to 99%.

In some embodiments, fragmented nucleic acids and control nucleic acids, which are prepared by any method described herein, are diluted so that the final concentration of at least one of the sequences-of-interest in the dilution is present at a desired concentration. In some embodiments, the final concentration of the at least one sequence-of-interest is in a range of about 0.00001%-10%, or about $10^{-8}$-$10^{-1}$, or about $10^{-1}$ to 99%.

In some embodiments, control nucleic acids which are prepared by any of the methods described herein, and having the known wild-type and known variant sequences are used in a next generation library preparation and sequencing workflow to detect/determine that level of abundance of at least one wild-type or variant sequence-of-interest that is present in a control preparation at 10%-0.0000001%.

In some embodiments, control nucleic acids which is prepared by the methods described herein, and having the known wild-type and known variant sequences with reduced amount of structurally damaged nucleic acids and reduced amount of artifact sequence mutations are used in a next generation library preparation and sequencing workflow that yields a reduced number of false positive sequencing reads (e.g., zero-10, or zero-5, or zero-2 false positive sequencing reads from control nucleic acids). In some embodiments, the false positive sequencing reads correlate with one or more artifact sequence mutations.

In some embodiments, fragmented nucleic acids and control nucleic acids, prepared using the methods provided herein, are used for any one or any combination of nucleic acid manipulation steps including: end-repairing, internal-repairing, end-tailing, size-selecting, adaptor-joining, nick-translating, amplifying, measuring, quantifying, diluting and/or sequencing.

One advantage of the systems, as well as related compositions, kits and methods, described in the present teachings is that they are used to prepare fragmented nucleic acids having a reduced amount of structurally damaged nucleic acids and a reduced amount of artifact sequence mutations. These fragmented nucleic acids are used as a control sample which is subjected to a next generation library preparation and sequencing workflow, in parallel with one or more test samples, and the results of the control and the test samples are compared.

In some embodiments, one advantage of using the fragmentation systems and methods described in the present teachings, is that that the fragmentation conditions are modulated to generate customized fragmented nucleic acids having the desired characteristics. For example, the type of fragmentation force, the length of fragmentation time and the fragmentation temperature are increased or decreased to generate fragmented nucleic acids having the desired size range.

In some embodiments, one advantage of using the fragmentation systems and methods described in the present teachings, is that that they are used to generate two or more separate preparations of fragmented nucleic acids which are mixed together to create a mixed control nucleic acid having the desired known variant and wild-type sequences at the desired concentrations. For example, a mixture of different plasmids (or plasmid-like molecules) carrying different known variant sequences can be fragmented, and mixed with fragmented normal background DNA (e.g., a source of known wild-type sequences) together to generate a mixture of fragmented nucleic acids having a known concentration of the known variant sequence. In some embodiments, mixed control nucleic acids contain the same concentration of different known variant sequences. In one example, the concentration of each of the different variant sequences contained in the mixed control is about 0.1%. In some embodiments, mixed control nucleic acids contain different concentrations of the different known variant sequences within the mixed control. In one example, the concentration of a first variant sequence in the mixed control is about 0.1%, and the concentration of a second variant sequence in the mixed control is about 0.5%. A dilution series are prepared from the mixed control nucleic acids.

In some embodiments, one advantage of using the fragmentation systems and methods described in the present teachings, is that that they are used to prepare control nucleic acids having known fusion DNA sequence or known fusion RNA sequences. In one example, RNA is extracted from one or more cell lines that are known have a fusion mutation. Cell lines, such as H2228, HCC78 and Lc2/AD are known to carry ALK, RET and ROS1 fusion mutations (e.g., ROS-ALK fusion RNA), and RNA isolated from these cell lines will have fusion RNA sequences. RNA isolated from these cell lines is fragmented to a desired size or size range, and the fragmented RNA is mixed with cfDNA or with fragmented DNA (e.g., prepare using the methods described herein), or mixed with cell-free total nucleic acids that contains both DNA and RNA. The mixture can contain any concentration of fragmented RNA, including a range of about 0.001-10%.

In some embodiments, one advantage of using the fragmentation systems and methods described in the present teachings, is that that they are used to prepare control nucleic acids having known copy number variations. In some embodiments, DNA is isolated from cells or cell culture that is known to carry a copy number variation of a sequence or gene or interest. The isolated DNA is fragmented to a desired size or size range, and the fragmented DNA is mixed with fragmented background normal DNA (known to lack copy number variation). The background DNA can also be fragmented using the methods described herein. The mixture can contain any concentration of fragmented copy number variation DNA, including a range of about 0.001-10%.

Control samples are useful as a dependable nucleic acid control sample. Control samples are useful for detecting a nucleic acid sequence associated with a disease or abnormal condition. Control samples are useful for detecting the abundance level of mutant or variant nucleic acids that are associated with a disease or abnormal condition. Control samples are useful for validating the abundance level of a sequence-of-interest in a test sample. Control samples are useful for validating the copy number variation of a sequence-of-interest in a test sample. Control samples are useful for establishing the lower end of detection (sensitivity) of a next gen library preparation and sequencing workflow. Control samples are useful as a dependable control nucleic acid (a proper control sample) for comparing the detection of low abundance sequences and/or copy number variations in a test sample. In some embodiments, the test sample comprises DNA or RNA or recombinant DNA or recombinant RNA. In some embodiments, the test sample comprises cell-free nucleic acids from a biological fluid, nucleic acids from a biopsied tissue, nucleic acids from a needle biopsy, or nucleic acids from cells. In some embodiments, the test sample comprises nucleic acids isolated from a tumor, tumor cells or circulating tumor cells.

In some embodiments, provided are methods, as well as related compositions, kits, and systems, for fragmenting nucleic acids with any one or any combination of mechanical stress, changes in temperature or pH, chemical compounds, enzymatic reactions, and/or radiation energy. In some embodiments, fragmenting nuclei acids with mechanical stress can damage nucleic acids. In some embodiments, mechanical stresses that damage nucleic acids include shearing forces, fluid shear, hydrodynamic shear, pulsatile shear or cavitation. In some embodiments, mechanical forces that can damage nucleic acids include acoustic force, nebulizing force, sonication force, cavitation force or shearing force. In some embodiments, apparatuses that can damage nucleic acids during fragmentation including acoustic shearing apparatuses, nebulizing apparatuses, sonication apparatuses, needle shearing apparatuses or French press apparatuses. Other examples of mechanical stress that produce nucleic acid damage include pipetting, stirring, centrifuging, pumping, filtering, spray drying, injecting or container-filling.

In some embodiments, the nucleic acid fragmentation procedures involving mechanical stress, generate reactive free radicals or reactive oxygen species which can damage the nucleic acids or convert the bases (oxidative mutation).

In some embodiments, provided are methods, as well as related compositions, kits, and systems, for reducing nucleic acid damage during exposure to reactive free radicals or reactive oxygen species, such as for example during fragmentation procedures using mechanical stress which can generate reactive free radicals or reactive oxygen species.

In some embodiments, the nucleic acid damage includes damage to any portion of the nucleic acid. The nucleic acid damage includes a break in any phosphate backbone bond (or analogous backbone bonds in nucleic acids with alternative backbones), a break in any bond in the sugar ring structure or any bond in the base ring structure, or a break in any of the bonds that link the base to the sugar or any bonds that link the sugar to the phosphate groups. In some embodiments, nucleic acid damage includes generating one or more abasic sites. In some embodiments, nucleic acid damage includes strand scission.

In some embodiments, nucleic acid damage includes oxidative damage which generates nucleic acid sequence mutation artifacts in the form of base substitutions, including base transitions and base transversions. Base transitions include interchanging purine bases resulting in converting an adenine to guanine, or converting guanine to adenine (A↔G), or interchange of one-ring pyrimidines resulting in converting cytosine to thymine, or converting thymine to cytosine (C↔T). Base transversions include interchanging pyrimidine bases with purine bases. For example, oxidative damage can convert guanines to 8-oxo-guanine. 8-oxo guanine pairs with cytosine and adenosine and during PCR amplification which can lead to base transversions (e.g., C>A and G>T).

In some embodiments, nucleic acid damage includes base transitions, including: C>T, T>C, A>G, and G>A.

In some embodiments, nucleic acid damage includes base transversions, including: A>T, T>A, C>T, T>C, A>C, C>A, G>T and T>G.

In some embodiments, a base transition or a base transversion is detected in a next generation library preparation and sequencing workflow as a false positive sequencing read.

In some embodiments, provided are methods, as well as related compositions, kits, and systems, for reducing nucleic acid damage by fragmenting nucleic acids in the presence of a damage-mitigating reagent and optionally a chelating reagent, to reduce nucleic acid base transitions and/or base transversions.

In some embodiments, provided are methods, as well as related compositions, kits, and systems, for reducing nucleic acid damage by fragmenting nucleic acids in the presence of a damage-mitigating reagent and optionally a chelating reagent, to reduce the number or percentage of false positive sequencing reads which can be caused by nucleic acid base transitions and/or base transversions.

In some embodiments, provided are methods, as well as related compositions, kits, and systems, for preparing a control nucleic acid which includes reducing nucleic acid damage, by fragmenting nucleic acids in the presence of at least one or a combination of a nucleic acid damage-mitigating reagent and/or chelating reagent. In some embodiments, a nucleic acid damage-mitigating reagent comprises an antioxidant reagent, free radical scavenger, oxygen scavenger, triple quenchers and/or reagents that reduce fading of fluorescent compounds.

In some embodiments, nucleic acids are fragmented in the presence of any one or any combination of a nucleic acid damage-mitigating reagent, including: 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; indole-3-acetic acid; insulin chain B fragment; water-soluble chitsan-indole-3-propionic acid conjugates (e.g., see Hebert, U.S. Pat. No. 7,125,861); melatonin (and its derivatives); monoethanolamine; carnitine; acetylcarnitine; β-hydroxy-γ(trimethylammonio)butyrate hydrochloride (DL-carnitine); beta-mercaptoethanol; sodium azide; glutathione; nitrous oxide; superoxide dismutase; glucose oxidase/catalase (GO/Cat); oxidase/peroxidase enzyme systems (e.g., glucose oxidases, alcohol oxidases, cholesterol oxidases, lactate oxidases, pyruvate oxidases, and xanthine oxidases); horseradish peroxidase (HRP); glutathione peroxidase; protocatachaute 3,4 dioxygenase (PCD); ergothioneine; methionine; cysteine; beta-dimethyl cysteine (penicillamine); mercaptopropionylglycine; sodium 2-mercaptoethanesulfonate (MESNA); glutathione; dithiothreitol; N-acetyl cysteine; captopril; imidazole; lycopene; carotene (e.g., alpha-, beta-, and gamma-carotene, and analogs thereof); antheraxanthin; astaxanthin; canthaxanthin; neurosporene; rhodopsin; bixin; norbixin; zeaxanthin; lutein; bilirubin; biliverdin; tocopherols; polyene dialdehydes; vitamin E (e.g., alpha-tocopheryl succinate and its analogs); vitamin B6 (pyridoxine 1 and its derivatives); hydrazine (N2H4); sodium sulfite (Na2S03); hydroxylamine; glutathione; N-acetylcysteine; histidine; tryptophan; Trolox (6-hydroxy-2,5,7,84etramethylchroman-2-carboxylic acid and its analogs U-78715F and WIN62079); soluble forms of vitamin E; ascorbic acid (or ascorbate); butylated hydroxytoluene (BTH); nPG (n-propyl gallate); DABCO (1,4-diazabicyclo[2.2.2]octane; TCEP (tris(2-carboxyethyl) phosphine; 2-mercaptoethylamine (MEA); thioglycerol; and/or hydroquinone; spermidine; and the like.

In some embodiments, provided are methods, as well as related compositions, kits, and systems, for preparing a control nucleic acid which includes reducing nucleic acid damage, by fragmenting nucleic acids in the presence of at least one or a combination of a nucleic acid damage-mitigating reagent and/or chelating reagent.

In some embodiments, nucleic acids are fragmented in the presence of any one or any combination of a chelating reagent, which chelates a metal (e.g., a metal chelating reagent). In some embodiment, a chelating reagent includes an aminopolycarboxylic acid or phosphonic acid. In some embodiments, a chelating reagent chelates antimony, arsenic, bismuth, calcium, copper, gold, iron, lead, manganese, mercury, or thallium.

In some embodiments, nucleic acids are fragmented in the presence of any one or any combination of a chelating reagent, including: ethylenediamine-N,N'-bis(2-hydroxyphenylacetic acid) (EDDHA); ethylenediamine-N,N'-disuccinic acid (EDDS); ethylenediaminetetraacetic acid (EDTA); ethylenediamine tetra(methylene phosphonic acid) (EDTMP); and/or ethylene glycol-bis(β-aminoethyl ether)-N,N,N',N'-tetraacetic acid (EGTA).

In some embodiments, compounds that comprise a nucleic acid damage-mitigating reagent or chelating reagent are dissolved or formulated in appropriate solvents, including water, alcohol (e.g., ethanol, methanol), and/or DMSO.

In some embodiments, nucleic acids are fragmented in the presence of any one or any combination of a nucleic acid damage-mitigating reagent at a concentration of: about 0.01-0.1 mM; or about 0.1-1 mM; or about 1-2.5 mM; or about 2.5-5 mM; or about 5-10 mM; or about 10-25 mM; or about 25-50 mM; or about 50-100 mM.

In some embodiments, nucleic acids are fragmented in the presence of any one or any combination of a nucleic acid damage-mitigating reagent, including: 3-indole-propionic acid and monoethanolamine; carnitine and monoethanolamine; sodium-azide and monoethanolamine; 2-mercaptoehtylamine (MEA) and β-hydroxy-γ(trimethylammonio) butyrate hydrochloride (DL-carnitine); 3-indole-propionic acid and monoethanolamine and at least one chelating reagent (e.g., EDDHA, EDDS, EDTA, EDTMP, EGTA); 3-indole-propionic acid and at least one chelating reagent (e.g., EDDHA, EDDS, EDTA, EDTMP, EGTA); carnitine and monoethanolamine and at least one chelating reagent (e.g., EDDHA, EDDS, EDTA, EDTMP, EGTA); and sodium-azide and monoethanolamine and at least one chelating reagent (e.g., EDDHA, EDDS, EDTA, EDTMP, EGTA).

In some embodiments, nucleic acids are fragmented in the presence of any one or any combination of a nucleic acid damage-mitigating reagent and/or chelating reagent, including: 0.01-30 mM 3-indole-propionic acid; 5-50 mM carnitine; 10-100 mM sodium-azide; 1-10 mM 3-indole-propionic acid and 100 mM monoethanolamine; 5-50 mM carnitine and 100 mM monoethanolamine; or 10-100 mM sodium-azide and 100 mM monoethanolamine; 0.01-30 mM 3-indole-propionic acid and 0.01-30 mM of at least one chelating reagent (e.g., EDDHA, EDDS, EDTA, EDTMP, EGTA).

In some embodiments, provided are systems for reducing nucleic acid damage during fragmentation, wherein an exemplary system comprises: (a) a first plurality of polynucleotides; (b) at least one nucleic acid damage-mitigating reagent; and (c) optionally at least one chelating reagent.

In some embodiments, provided are systems for reducing nucleic acid damage during fragmentation, wherein a system comprises: (a) a single reaction mixture of nucleic acids, containing at least a first plurality of polynucleotides and a second plurality of polynucleotide; (b) at least one nucleic acid damage-mitigating reagent; and (c) optionally at least one chelating reagent.

In some embodiments, the damage-mitigating reagent and the chelating reagent reduce fragmentation-induced nucleic acid base transitions which are selected from a group consisting of C>T, T>C, A>G, and G>A.

In some embodiments, the damage-mitigating reagent and the chelating reagent reduce fragmentation-induced nucleic acid base transversions which are selected from a group consisting of, A>T, T>A, C>T, T>C, A>C, C>A, G>T and T>G.

In some embodiments, the system further comprises a nucleic acid fragmenting apparatus. In some embodiments, the nucleic acid fragmenting apparatus randomly fragments nucleic acids. In some embodiments, the nucleic acid fragmenting apparatus exerts acoustic force, nebulizing force, sonication force, or shearing force. In some embodiments, the nucleic acid fragmenting apparatus comprises: an acoustic shearing apparatus, a nebulizing apparatus, a sonication apparatus, a needle shearing apparatus or a French press apparatus.

In some embodiments, the first plurality of polynucleotides and/or second plurality of polynucleotides comprise at least one polynucleotide having a known variant sequence. In some embodiments, the first plurality of polynucleotides and/or second plurality of polynucleotides comprise 1-10000 polynucleotides having known variant sequences.

In some embodiments, the known variant sequence originates from human chromosome 1, 2, 3, 4, 5, 6, 7, 8, 9, 10, 11, 12, 13, 14, 15, 16, 17, 18, 19, 20, 21, 22, X or Y.

In some embodiments, the first plurality of polynucleotides and/or second plurality of polynucleotides comprise at least one polynucleotide having a known wild-type sequence. In some embodiments, the first plurality of polynucleotides and/or second plurality of polynucleotides comprise 1-10000 polynucleotides having known wild-type sequences.

In some embodiments, the known wild-type sequence is from human chromosome 1, 2, 3, 4, 5, 6, 7, 8, 9, 10, 11, 12, 13, 14, 15, 16, 17, 18, 19, 20, 21, 22, X or Y.

In some embodiments, the first plurality of polynucleotides and/or second plurality of polynucleotides comprise a known amount of at least one variant sequence.

In some embodiments, the first plurality of polynucleotides and/or second plurality of polynucleotides comprise a known amount of at least one wild-type sequence.

In some embodiments, the first plurality of polynucleotides and/or second plurality of polynucleotides comprise 1-1000 different variant sequences, or 1-500 different variant sequences.

In some embodiments, provided are systems for reducing nucleic acid damage during fragmentation, wherein a system comprises: a single reaction mixture, containing at least (i) a plurality of polynucleotides which includes at least one polynucleotide having a known variant sequence or a known aneuploidy variation, and the plurality of polynucleotides includes at least one polynucleotide having a known wild-type sequence; (ii) at least one nucleic acid damage-mitigating reagent selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, indole-3-acetic acid; and (iii) at least one chelating reagent selected from a group consisting of EDTA, EDDHA, EDDS, EDTMP and EGTA.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the system further comprises a nucleic acid fragmenting apparatus. In some embodiments, the nucleic acid fragmenting apparatus randomly fragments nucleic acids. In some embodiments, the nucleic acid fragmenting apparatus exerts acoustic force, nebulizing force, sonication force, or shearing force. In some embodiments, the nucleic acid fragmenting apparatus comprises: an acoustic shearing apparatus, a nebulizing apparatus, a sonication apparatus, a needle shearing apparatus or a French press apparatus.

In some embodiments, the single reaction mixture further comprises at least a second plurality of polynucleotides which includes least one polynucleotide having a known variant sequence or a known aneuploidy variation, or a plurality of polynucleotides which includes at least one polynucleotide having a known wild-type sequence.

In some embodiments, the single reaction mixture further comprises at least a second plurality of polynucleotides which includes polynucleotides having 1-1000 known variant sequences or 1-1000 known aneuploidy variations, or a plurality of polynucleotides which includes polynucleotide having 1-1000 known wild-type sequence.

In some embodiments, the plurality of polynucleotides originate from any one or any combination of human chromosome 1, 2, 3, 4, 5, 6, 7, 8, 9, 10, 11, 12, 13, 14, 15, 16, 17, 18, 19, 20, 21, 22, X and/or Y.

In some embodiments, provided is a system for preparing fragmented nucleic acids for use as a control nucleic acid having reduced nucleic acid damage, wherein the system comprises: a single reaction mixture, containing at least (i) a first plurality of polynucleotides which includes at least one polynucleotide having a known wild-type sequence; and (ii) a second plurality of polynucleotides which includes at least one polynucleotide having a known variant sequence or a known aneuploidy variation; (iii) at least one nucleic acid damage-mitigating reagent selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, indole-3-acetic acid, and (iv) at least one chelating reagent selected from a group consisting of EDTA, EDDHA, EDDS, EDTMP and EGTA.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the system further comprises a nucleic acid fragmenting apparatus. In some embodiments, the nucleic acid fragmenting apparatus randomly fragments nucleic acids. In some embodiments, the nucleic acid fragmenting apparatus exerts acoustic force, nebulizing force, sonication force, or shearing force. In some embodiments, the nucleic acid fragmenting apparatus comprises: an acoustic shearing apparatus, a nebulizing apparatus, a sonication apparatus, a needle shearing apparatus or a French press apparatus.

In some embodiments, wherein the single reaction mixture comprises the first plurality of polynucleotides which includes polynucleotides having 1-1000 known wild-type sequence; and (ii) a second plurality of polynucleotides which includes polynucleotides having 1-1000 known variant sequence or a known aneuploidy variation.

In some embodiments, provided are control nucleic acids having reduced nucleic acid damage, wherein the control nucleic acids comprise: a plurality of nucleic acid fragments from a first plurality of polynucleotides which have been fragmented in the presence of at least one nucleic acid damage-mitigating reagent and optionally at least one chelating reagent to generate the plurality of nucleic acid fragments from the first plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides comprise fragments of about 50-500 bp, or about 100-450 bp, or about 100-200 bp.

In some embodiments, the concentration of a fragment having the wild-type sequence is in a range of 10%-0.00001% of the total concentration of the plurality of nucleic acids, wherein the total concentration of the plurality of nucleic acids includes the plurality of nucleic acid fragments from the first plurality of polynucleotides. In some embodiments, the concentration of a fragment having the wild-type sequence is about $10^{-8}$-$10^{-1}$, or about $10^{-1}$ to 99%, of the total concentration of the plurality of nucleic acids.

In some embodiments, the concentration of a fragment having the variant sequence or the aneuploidy variation is in a range of 10%-0.00001% of the total concentration of the plurality of nucleic acids in the single vessel, wherein the total concentration of the plurality of nucleic acids includes the plurality of nucleic acid fragments from the first plurality of polynucleotides. In some embodiments, the concentration of a fragment having the variant sequence or the aneuploidy variation is about $10^{-8}$-$10^{-1}$, or about $10^{-1}$ to 99%, of the total concentration of the plurality of nucleic acids.

In some embodiments, provided are control nucleic acids having reduced nucleic acid damage, wherein the control nucleic acids comprise: a mixture of nucleic acid fragments which have been fragmented in the presence of at least one nucleic acid damage-mitigating reagent and optionally in the presence of at least one chelating reagent, wherein the mixture of nucleic acid fragments contains at least a plurality of nucleic acid fragments from a first plurality of polynucleotides and a plurality of nucleic acid fragments from a second plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides and the nucleic acid fragments from the second plurality of polynucleotides have a reduced number of any one or any combination of nucleic acid transitions C>T, T>C, A>G, and G>A and/or wherein the nucleic acid fragments from the first plurality of polynucleotides and the nucleic acid fragments from the second plurality of polynucleotides have a reduced number of any one or any combination of nucleic acid transversions A>T, T>A, C>T, T>C, A>C, C>A, G>T and T>G, compared to the nucleic acid fragments from the first plurality of polynucleotides and the nucleic acid fragments from the second plurality of polynucleotides that have been fragmented in the absence of the nucleic acid damage-mitigating reagent and the chelating reagent.

In some embodiments, the nucleic acid fragments from the first plurality of polynucleotides comprise fragments of about 50-500 bp, or about 100-450 bp, or about 100-200 bp.

In some embodiments, the concentration of a fragment having the wild-type sequence is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the wild-type sequence is about $10^{-8}$-$10^{-1}$, or about $10^{-1}$ to 99%, of the total concentration of the plurality of nucleic acids.

In some embodiments, the concentration of a fragment having the variant sequence or the aneuploidy variation is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the variant sequence or the aneuploidy variation is about $10^{-8}$-$10^{-1}$, or about $10^{-1}$ to 99%, of the total concentration of the plurality of nucleic acids.

In some embodiments, provided are control nucleic acids having reduced nucleic acid damage, wherein the control nucleic acids comprise: (i) a plurality of nucleic acid fragments from a first plurality of polynucleotides which contains at least one polynucleotide having a known wild-type sequence, wherein the first plurality of polynucleotides have been fragmented in the presence of at least one nucleic acid damage-mitigating reagent and at least one chelating reagent to generate the plurality of nucleic acid fragments from the first plurality of polynucleotides; and (ii) a plurality of nucleic acid fragments from a second plurality of polynucleotides which contains at least one polynucleotide having a known variant sequence or a known aneuploidy variation, wherein the second plurality of polynucleotides have been fragmented in the presence of at least one nucleic acid damage-mitigating reagent and at least one chelating reagent to generate the plurality of nucleic acid fragments from the second plurality of polynucleotides; and wherein the nucleic acid damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid, and wherein the chelating reagent is selected from a group consisting of EDTA, EDDHA, EDDS, EDTMP and EGTA.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides and the nucleic acid fragments from the second plurality of polynucleotides have a reduced number of any one or any combination of nucleic acid transitions C>T, T>C, A>G, and G>A and/or wherein the nucleic acid fragments from the first plurality of polynucleotides and the nucleic acid fragments from the second plurality of polynucleotides have a reduced number of any one or any combination of nucleic acid transversions A>T, T>A, C>T, T>C, A>C, C>A, G>T and T>G, compared to the nucleic acid fragments from the first plurality of polynucleotides and the nucleic acid fragments from the second plurality of polynucleotides that have been fragmented in the absence of the nucleic acid damage-mitigating reagent and the chelating reagent.

In some embodiments, the nucleic acid fragments from the first plurality of polynucleotides comprise fragments of about 50-500 bp, or about 100-450 bp, or about 100-200 bp.

In some embodiments, the nucleic acid fragments from the second plurality of polynucleotides comprise fragments of about 50-500 bp, or about 100-450 bp, or about 100-200 bp.

In some embodiments, the nucleic acid fragments from the first plurality of polynucleotides and the nucleic acid fragments from the second plurality of polynucleotides are contained in a single vessel.

In some embodiments, the nucleic acid fragments from the first plurality of polynucleotides is contained in a first vessel and the nucleic acid fragments from the second plurality of polynucleotides is contained in a second vessel.

In some embodiments, the concentration of a fragment having the known wild-type sequence in the single vessel is in a range of 10%-0.00001% of the total concentration of the plurality of nucleic acids in the single vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having the known variant sequence or the known aneuploidy variation in the single vessel is in a range of 10%-0.00001% of the total concentration of the plurality of nucleic acids in the single vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, the concentration of a fragment having the known wild-type sequence in the first vessel is in a range of 10%-0.00001% of the total concentration of the plurality of nucleic acids in the first vessel, wherein the total concentration of the plurality of nucleic acids includes the plurality of nucleic acid fragments from the first plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having the known variant sequence or the known aneuploidy variation in the second vessel is in a range of 10%-0.00001% of the total concentration of the plurality of nucleic acids in the second vessel, wherein the total concentration of the plurality of nucleic acids includes the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, provided are kits comprising: a plurality of nucleic acid fragments from a first plurality of polynucleotides which have been fragmented in the presence of at least one nucleic acid damage-mitigating reagent and optionally at least one chelating reagent to generate the plurality of nucleic acid fragments from the first plurality of polynucleotides. In some embodiments, the kit comprises a control nucleic acid which includes the plurality of nucleic acid fragments from the first plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides have a reduced number of any one or any combination of nucleic acid transitions C>T, T>C, A>G, and G>A and/or wherein the nucleic acid fragments from the first plurality of polynucleotides have a reduced number of any one or any combination of nucleic acid transversions A>T, T>A, C>T, T>C, A>C, C>A, G>T and T>G, compared to the nucleic acid fragments from the first plurality of polynucleotides that have been fragmented in the absence of the nucleic acid damage-mitigating reagent and the chelating reagent.

In some embodiments, the plurality of nucleic acid fragments from the first plurality of polynucleotides are fragmented to any size range including size ranges of about 20-2000 bp, or about 50-500 bp, or about 100-450 bp, or about 100-200 bp.

In some embodiments, provided are kits comprising: (a) a plurality of nucleic acid fragments from a first plurality of polynucleotides; (b) a plurality of nucleic acid fragments from a second plurality of polynucleotides; wherein the first and second plurality of polynucleotides have been fragmented in the presence of at least one nucleic acid damage-mitigating reagent and optionally at least one chelating reagent to generate the plurality of nucleic acid fragments from the first plurality of polynucleotides and the plurality of nucleic acid fragments from the second plurality of polynucleotides. In some embodiments, the kit comprises a control nucleic acid which includes the plurality of nucleic acid fragments from the first plurality of polynucleotides and the plurality of nucleic acid fragments from the second plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides and the nucleic acid fragments from the second plurality of polynucleotides have a reduced number of any one or any combination of nucleic acid transitions C>T, T>C, A>G, and G>A and/or wherein the nucleic acid fragments from the first plurality of polynucleotides and the nucleic acid fragments from the second plurality of polynucleotides have a reduced number of any one or any combination of nucleic acid transversions A>T, T>A, C>T, T>C, A>C, C>A, G>T and T>G, compared to the nucleic acid fragments from the first plurality of polynucleotides and the nucleic acid fragments from the second plurality of polynucleotides that have been fragmented in the absence of the nucleic acid damage-mitigating reagent and the chelating reagent.

In some embodiments, the nucleic acid fragments from the first plurality of polynucleotides and the nucleic acid fragments from the second plurality of polynucleotides comprise fragments about 50-500 bp, or about 100-450 bp, or about 100-200 bp.

In some embodiments, provided is a kit for use as a control nucleic acid, the kit comprising: (a) a plurality of nucleic acid fragments from a first plurality of polynucleotides which contains at least one polynucleotide having at least one known wild-type sequence; and (b) a plurality of nucleic acid fragments from a second plurality of polynucleotides which contains at least one polynucleotide having at least one known variant sequence or a known aneuploidy variation; wherein the plurality of nucleic acid fragments from the first plurality of polynucleotides and the plurality of nucleic acid fragments from the second plurality of polynucleotides have been prepared by fragmenting a first plurality of polynucleotides and a second plurality of polynucleotides in the presence of at least one nucleic acid damage-mitigating reagent and at least one chelating reagent to generate the plurality of nucleic acid fragments from the first plurality of polynucleotides and the plurality of nucleic acid fragments from the second plurality of polynucleotides; wherein the nucleic acid damage-mitigating reagent is selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid, and wherein the chelating reagent is selected from a group consisting of EDTA, EDDHA, EDDS, EDTMP and EGTA. In some embodiments, the kit comprises a control nucleic acid which includes the plurality of nucleic acid fragments from the first plurality of polynucleotides and the plurality of nucleic acid fragments from the second plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides and the nucleic acid fragments from the second plurality of polynucleotides have a reduced number of any one or any combination of nucleic acid transitions C>T, T>C, A>G, and G>A and/or wherein the nucleic acid fragments from the first plurality of polynucleotides and the nucleic acid fragments from the second plurality of polynucleotides have a reduced number of any one or any combination of nucleic acid transversions A>T, T>A, C>T, T>C, A>C, C>A, G>T and T>G, compared to the nucleic acid fragments from the first plurality of polynucleotides and the nucleic acid fragments from the second plurality of polynucleotides that have been fragmented in the absence of the nucleic acid damage-mitigating reagent and the chelating reagent.

In some embodiments, the nucleic acid fragments from the first plurality of polynucleotides and the nucleic acid fragments from the second plurality of polynucleotides comprise fragments of about 50-500 bp, or about 100-450 bp, or about 100-200 bp.

In some embodiments, the plurality of nucleic acid fragments from the first plurality of polynucleotides and the plurality of nucleic acid fragments from the second plurality of polynucleotides are contained in a single vessel.

In some embodiments, the plurality of nucleic acid fragments from the first plurality of polynucleotides is contained in a first vessel and the plurality of nucleic acid fragments from the second plurality of polynucleotides is contained in a second vessel.

In some embodiments, the concentration of a fragment having the known wild-type sequence in the single vessel is in a range of 10%-0.00001% of the total concentration of the plurality of nucleic acids in the single vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having the known variant sequence or the known aneuploidy variation in the single vessel is in a range of 10%-0.00001% of the total concentration of the plurality of nucleic acids in the single vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, the concentration of a fragment having the known wild-type sequence in the first vessel is in a range of 10%-0.00001% of the total concentration of the plurality of nucleic acids in the first vessel, wherein the total concentration of the plurality of nucleic acids includes the plurality of nucleic acid fragments from the first plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having the known variant sequence or the known aneuploidy variation in the second vessel is in a range of 10%-0.00001% of the total concentration of the plurality of nucleic acids in the second vessel, wherein the total concentration of the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, in the first vessel, the plurality of nucleic acid fragments from the first plurality of polynucleotides comprise 1-1000 different known wild-type sequences. In some embodiments, in the second vessel, the plurality of nucleic acid fragments from the second plurality of polynucleotides comprises 1-10000 different known variant sequences.

In some embodiments, provided are methods for fragmenting nucleic acids, comprising: (a) providing a single reaction mixture containing (i) a first plurality of polynucleotides, (ii) at least one nucleic acid damage-mitigating reagent, and optionally (iii) at least one chelating reagent; and (b) fragmenting the first plurality of polynucleotides to generate a plurality of nucleic acid fragments from the first plurality of polynucleotides. In some embodiments, the methods for fragmenting nucleic acids are used to prepare a control nucleic acid.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, fragmenting the first plurality of polynucleotides in the presence of the nucleic acid damage-mitigating reagent and the chelating reagent reduces the number of any one or any combination of nucleic acid transitions C>T, T>C, A>G, and G>A and/or wherein fragmenting the first plurality of polynucleotides in the presence of the nucleic acid damage-mitigating reagent and the chelating reagent reduces the number of any one or any combination of nucleic acid transversions A>T, T>A, C>T, T>C, A>C, C>A, G>T and T>G, compared to fragmenting the first plurality of polynucleotides in the absence of the nucleic acid damage-mitigating reagent and the chelating reagent.

In some embodiments, the nucleic acid fragments from the first plurality of polynucleotides comprise fragments of about 50-500 bp, or about 100-450 bp, or about 100-200 bp.

In some embodiments, the first plurality of polynucleotides contains 1-1000 known variant sequences. In some embodiments, the first plurality of polynucleotides contains 1-1000 known wild-type sequences.

In some embodiments, the concentration of a fragment having a known wild-type sequence in is in a range of 10%-0.00001% of the total concentration of the plurality of nucleic acids in the, wherein the total concentration of the plurality of nucleic acids includes the plurality of nucleic acid fragments from the first plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having a known variant sequence in is in a range of 10%-0.00001% of the total concentration of the plurality of nucleic acids in the, wherein the total concentration of the plurality of nucleic acids includes the plurality of nucleic acid fragments from the first plurality of polynucleotides. In some embodiments, the concentration of a fragment having the known variant sequence is about $10^{-8}$-$10^{-1}$, or about $10^{-1}$ to 99%, of the total concentration of the plurality of nucleic acids.

In some embodiments, the method further comprises: (c) providing a second single reaction mixture containing (i) a second plurality of polynucleotides, (ii) at least one nucleic acid damage-mitigating reagent, and optionally (iii) at least one chelating reagent; and (d) fragmenting the second plurality of polynucleotides to generate a plurality of nucleic acid fragments from the second plurality of polynucleotides.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, fragmenting the second plurality of polynucleotides in the presence of the nucleic acid damage-mitigating reagent and the chelating reagent reduces the number of any one or any combination of nucleic acid transitions C>T, T>C, A>G, and G>A and/or wherein fragmenting the second plurality of polynucleotides in the presence of the nucleic acid damage-mitigating reagent and the chelating reagent reduces the number of any one or any combination of nucleic acid transversions A>T, T>A, C>T, T>C, A>C, C>A, G>T and T>G, compared to fragmenting the second plurality of polynucleotides in the absence of the nucleic acid damage-mitigating reagent and the chelating reagent.

In some embodiments, the nucleic acid fragments from the second plurality of polynucleotides comprise fragments of about 50-500 bp, or about 100-450 bp, or about 100-200 bp.

In some embodiments, the second plurality of polynucleotides contains 1-1000 known variant sequences. In some embodiments, the second plurality of polynucleotides contains 1-1000 known wild-type sequences.

In some embodiments, the plurality of nucleic acid fragments from the second plurality of polynucleotides contains a known amount of at least one variant sequence.

In some embodiments, the plurality of nucleic acid fragments from the second plurality of polynucleotides contains a known amount of at least one wild-type sequence.

In some embodiments, the concentration of a fragment having a known wild-type sequence in is in a range of 10%-0.00001% of the total concentration of the plurality of nucleic acids in the, wherein the total concentration of the plurality of nucleic acids includes the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having a known variant sequence in is in a range of 10%-0.00001% of the total concentration of the plurality of nucleic acids in the, wherein the total concentration of the plurality of nucleic acids includes the plurality of nucleic acid fragments from the second plurality of polynucleotides. In some embodiments, the concentration of a fragment having the known variant sequence is about $10^{-8}$-$10^{-1}$, or about $10^{-1}$ to 99%, of the total concentration of the plurality of nucleic acids.

In some embodiments, the method further comprises: (e) mixing together the plurality of nucleic acid fragments from the first plurality of polynucleotides and the plurality of nucleic acid fragments from the second plurality of polynucleotides.

In some embodiments, the ratio of the plurality of nucleic acid fragments from the first plurality of polynucleotides and the plurality of nucleic acid fragments from the second plurality of polynucleotides is 1:1.

In some embodiments, the concentration of a fragment having a known wild-type sequence is in a range of 10%-0.00001% of the total concentration of the plurality of nucleic acids in the mixture, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having a known variant sequence or the known aneuploidy variation is in a range of 10%-0.00001% of the total concentration of the plurality of nucleic acids in the mixture, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, provided are methods for fragmenting nucleic acids, comprising: (a) providing a single reaction mixture containing (i) a first plurality of polynucleotides, (ii) a second plurality of polynucleotides, (iii) at least one nucleic acid damage-mitigating reagent, and optionally (iv) at least one chelating reagent; and (b) fragmenting the first and second plurality of polynucleotides to generate a plurality of nucleic acid fragments from the first plurality of polynucleotides and a plurality of nucleic acid fragments from the second plurality of polynucleotides. In some embodiments, the methods for fragmenting nucleic acids are used to prepare a control nucleic acid.

In some embodiments, the damage-mitigating reagent and the chelating reagent reduce fragmentation-induced nucleic acid transitions which are selected from a group consisting of C>T, T>C, A>G, and G>A.

In some embodiments, the damage-mitigating reagent and the chelating reagent reduce fragmentation-induced nucleic acid transversions which are selected from a group consisting of, A>T, T>A, C>T, T>C, A>C, C>A, G>T and T>G.

In some embodiments, the fragmenting the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transitions C>T, T>C, A>G, and G>A and/or wherein fragmenting the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transversions A>T, T>A, C>T, T>C, A>C, C>A, G>T and T>G, compared to fragmenting the nucleic acid fragments from the first plurality of polynucleotides and the nucleic acid fragments from the second plurality of polynucleotides in the absence of the nucleic acid damage-mitigating reagent and the chelating reagent.

In some embodiments, the nucleic acid fragments from the first plurality of polynucleotides and the nucleic acid fragments from the second plurality of polynucleotides comprise fragments of about 50-500 bp, or about 100-450 bp, or about 100-200 bp.

In some embodiments, the first plurality of polynucleotides and the second plurality of polynucleotides are fragmented in a single reaction vessel.

In some embodiments, the plurality of nucleic acid fragments from the first plurality of polynucleotides and/or the plurality of nucleic acid fragments from the second plurality of polynucleotides contains a known amount of at least one variant sequence.

In some embodiments, the plurality of nucleic acid fragments from the first plurality of polynucleotides and/or the plurality of nucleic acid fragments from the second plurality of polynucleotides contains a known amount of at least one wild-type sequence.

In some embodiments, the plurality of nucleic acid fragments from the first plurality of polynucleotides and/or the plurality of nucleic acid fragments from the second plurality of polynucleotides contain 1-1000 different known variant sequences.

In some embodiments, the plurality of nucleic acid fragments from the first plurality of polynucleotides and/or the plurality of nucleic acid fragments from the second plurality of polynucleotides contain 1-1000 different known wild-type sequences.

In some embodiments, the concentration of a fragment having a known wild-type sequence is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having a known variant sequence or the known aneuploidy variation is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, the method further comprises: (a) providing an aliquot of the control nucleic acid containing the plurality of nucleic acid fragments from the first plurality of polynucleotides and the plurality of nucleic acid fragments from the second plurality of polynucleotides; and (b) appending an oligonucleotide adaptor to one end or both ends of the plurality of nucleic acid fragments from the first plurality of polynucleotides and the plurality of nucleic acid fragments from the second plurality of polynucleotides to generate a plurality of tagged fragment polynucleotides. An aliquot of the control nucleic acid includes a portion or all of the control nucleic acid.

In some embodiments, the oligonucleotide adaptor is appended via ligation, primer extension or PCR amplification.

In some embodiments, the oligonucleotide adaptor which is appended via ligation comprises a double-stranded linear adaptor, a stem-looped adaptor or a Y-shaped adaptor.

In some embodiments, the oligonucleotide adaptor which is appended via primer extension or PCR amplification comprises a single-stranded primer having (i) a 3' region that specifically binds a target sequence in the plurality of polynucleotides from the nucleic acid sample, and (ii) a 5' tail having a sequence that is not complementary to a target sequence in the plurality of polynucleotides from the nucleic acids sample. In some embodiments, the 5' tail can contain a unique tag sequence and optionally a sample-specific barcode sequence. In some embodiments, the 5' tail can contain a universal sequence, including at least one or any combination of a universal sequence, including an amplification primer sequence, a sequencing primer sequence, a capture primer sequence and/or a cleavable site. In some embodiments, the nucleic acid fragments which are generated using any of the fragmenting procedures described in the teachings herein are appended with one or more adaptors carrying a unique randomer tag, for example using a molecular tagging method described in U.S. published application No. 2016/0362748, published Dec. 15, 2016, entitled "Methods, Systems, Compositions, Kits, Apparatus and Computer-Readable Media for Molecular Tagging" which is incorporated by reference in its entirety. In some embodiments, the unique tag sequence can uniquely identify an individual polynucleotide to which it is appended, and distinguish the individual tagged polynucleotide from other tagged polynucleotide in a mixture. In some embodiments, the oligonucleotide adaptor comprises a unique tag sequence from a repertoire of different unique tag sequences. In some embodiments, the repertoire of different unique tag sequences includes $10^4$-$10^9$ different unique sequences. In some embodiments, the unique tag sequence comprises at least one random or degenerate sequence. In some embodiments, the oligonucleotide adaptor comprises at least one fixed sequence that is the same sequence in all of the oligonucleotide adaptors. In some embodiments, the oligonucleotide adaptor comprises a unique tag sequence from a repertoire of different tag sequences and a fixed tag sequence that is the same sequence in all of the oligonucleotide adaptors. In some embodiments, the oligonucleotide adaptor comprises a unique tag sequence from a repertoire of different tag sequences and two or more different fixed tag sequences. In some embodiments, the oligonucleotide adaptor comprises two unique tag sequences from a repertoire of different tag sequences and two or more different fixed tag sequences. In some embodiments, the oligonucleotide adaptor comprises a random sequence flanked on both sides by a fixed sequence, or a fixed sequence flanked on both sides by a random sequence. In some embodiments, the oligonucleotide adaptor comprises two or more different unique tag sequences alternating with two or more fixed tag sequences.

In some embodiments, the oligonucleotide adaptors comprise the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10. In some embodiments, the fixed tag sequences "$(X)_x$" and "$(Y)_y$" are sequence alignment anchors.

In some embodiments, the polynucleotides are appended with a sample-specific barcode that identifies the sample or source from which polynucleotides are derived. The sample-specific barcode can be part of the adaptor containing the unique tag sequence, or can be contained on a separate adaptor. The sample-specific barcode sequence can be appended to the polynucleotide by ligation, primer extension or PCR amplification.

In some embodiments, the method further comprises: amplifying the plurality of tagged fragment polynucleotides to generate a plurality of tagged fragment amplicons.

In some embodiments, the method further comprises: sequencing at least a portion of the tagged fragment amplicons to generate a plurality of sequencing reads.

In some embodiments, the method further comprises: determining that at least one sequence of interest is present in the aliquot of the control nucleic acid at an abundance level of about $10^{-8}$ to about 10%. In some embodiments, the at least one sequence of interest comprises a variant sequence or a wild-type sequence.

In some embodiments, the aliquot contains 1-1000 different variant sequences.

In some embodiments, the at least one sequence of interest comprises a variant sequence which is from human chromosome 1, 2, 3, 4, 5, 6, 7, 8, 9, 10, 11, 12, 13, 14, 15, 16, 17, 18, 19, 20, 21, 22, X or Y.

In some embodiments, the aliquot contains 1-1000 different wild-type sequences.

In some embodiments, the at least one sequence of interest comprises a wild-type sequence which is from human chromosome 1, 2, 3, 4, 5, 6, 7, 8, 9, 10, 11, 12, 13, 14, 15, 16, 17, 18, 19, 20, 21, 22, X or Y.

In some embodiments, the aliquot of the control nucleic acid contains about 1-100 ng, or about 1-50 ng, or about 1-25 ng.

In some embodiments, the method further comprises: detecting 0-10 or 0-5 false positive sequencing reads. In some embodiments, the false positive sequencing reads comprises a fragmentation-induced nucleic acid transitions which are selected from a group consisting of C>T, T>C, A>G, and G>A. In some embodiments, the false positive sequencing reads comprises a fragmentation-induced nucleic acid transversions which are selected from a group consisting of, A>T, T>A, C>T, T>C, A>C, C>A, G>T and T>G.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) determining that at least one sequence of interest is present in the aliquot of the test sample at an abundance level of about $10^{-8}$ to about 10%. In some embodiments, the at least one sequence of interest comprises a variant sequence or a wild-type sequence. An aliquot of the test sample includes a portion or all of the test sample.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) detecting 1-10 or 0-5 false positive sequencing reads. An aliquot of the test sample includes a portion or all of the test sample.

In some embodiments, provided are methods for fragmenting nucleic acids (e.g., methods for preparing a control nucleic acid), comprising: (a) providing a first single reaction mixture containing (i) a first plurality of polynucleotides, (ii) at least one nucleic acid damage-mitigating reagent selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid, and (iii) at least one chelating reagent selected from a group consisting of EDTA, EDDHA, EDDS, EDTMP and EGTA; (b) fragmenting the first plurality of polynucleotides to generate a plurality of nucleic acid fragments from the first plurality of polynucleotides; (c) optionally providing a second single reaction mixture containing (i) a second plurality of polynucleotides, (ii) at least one nucleic acid damage-mitigating reagent selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, and indole-3-acetic acid, and (iii) at least one chelating reagent selected from a group consisting of EDTA, EDDHA, EDDS, EDTMP and EGTA; and (d) optionally fragmenting the second plurality of polynucleotides to generate a plurality of nucleic acid fragments from the second plurality of polynucleotides.

In some embodiments, the damage-mitigating reagent and the chelating reagent in steps (a) and (c) reduce fragmentation-induced nucleic acid transitions which are selected from a group consisting of C>T, T>C, A>G, and G>A.

In some embodiments, the damage-mitigating reagent and the chelating reagent in steps (a) and (c) reduce fragmentation-induced nucleic acid transversions which are selected from a group consisting of, A>T, T>A, C>T, T>C, A>C, C>A, G>T and T>G.

In some embodiments, the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transitions C>T, T>C, A>G, and G>A and/or wherein fragmenting the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transversions A>T, T>A, C>T, T>C, A>C, C>A, G>T and T>G, compared to fragmenting the nucleic acid fragments from the first plurality of polynucleotides and the nucleic acid fragments from the second plurality of polynucleotides in the absence of the nucleic acid damage-mitigating reagent and the chelating reagent.

In some embodiments, the nucleic acid fragments from the first plurality of polynucleotides and the nucleic acid fragments from the second plurality of polynucleotides comprise fragments of about 50-500 bp, or about 100-450 bp, or about 100-200 bp.

In some embodiments, the first plurality of polynucleotides are fragmented in a first reaction vessel and the second plurality of polynucleotides are fragmented in a second reaction vessel.

In some embodiments, the first plurality of polynucleotides in the first vessel contains 1-1000 different known wild-type sequences.

In some embodiments, the second plurality of polynucleotides in the second vessel contains 1-1000 different known variant sequences.

In some embodiments, the method further comprises: forming a mixed fragments reaction vessel by mixing at least a portion of the plurality of nucleic acid fragments from the first plurality of polynucleotides from the first reaction vessel with at least a portion of the plurality of nucleic acid fragments from the second plurality of polynucleotides from the second reaction vessel.

In some embodiments, the mixed fragments reaction vessel, the ratio of the nucleic acid fragments from the second plurality of polynucleotides to the nucleic acid fragments from the first plurality of polynucleotides in the single vessel is a range of 1:1 to 1:1,000,000.

In some embodiments, the plurality of nucleic acid fragments from the first plurality of polynucleotides and/or the plurality of nucleic acid fragments from the second plurality of polynucleotides contain at least one polynucleotide having a known wild-type sequence, or contains at least one polynucleotide having a known variant sequence or a known aneuploidy variation.

In some embodiments, the plurality of nucleic acid fragments from the first plurality of polynucleotides and/or the plurality of nucleic acid fragments from the second plurality of polynucleotides contain 1-1000 different variant sequences.

In some embodiments, the plurality of nucleic acid fragments from the first plurality of polynucleotides and/or the plurality of nucleic acid fragments from the second plurality of polynucleotides comprise a known amount of the polynucleotide having the wild-type sequence.

In some embodiments, the plurality of nucleic acid fragments from the first plurality of polynucleotides and/or the plurality of nucleic acid fragments from the second plurality of polynucleotides comprise a known amount of the polynucleotide having the variant sequence or a known amount of the polynucleotide having the aneuploidy variation.

In some embodiments, the concentration of a fragment having a known wild-type sequence in the mixed fragments reaction vessel is in a range of 10%-0.00001% of the total concentration of the plurality of nucleic acids in the mixed fragments reaction vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known wild-type sequence is about $10^{-8}$-$10^{-1}$, or about $10^{-1}$ to 99%, of the total concentration of the plurality of nucleic acids.

In some embodiments, the concentration of a fragment having a known variant sequence or the known aneuploidy variation in the mixed fragments reaction vessel is in a range of 10%-0.00001% of the total concentration of the plurality of nucleic acids in the mixed fragments reaction vessel, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of a fragment having the known variant sequence or the aneuploidy variation is about $10^{-8}$-$10^{-1}$, or about $10^{-1}$ to 99%, of the total concentration of the plurality of nucleic acids.

In some embodiments, the concentration of a fragment having a known wild-type sequence or a known variant sequence in a first vessel is in a range of 10%-0.00001% of the total concentration of the plurality of nucleic acids in the first vessel, wherein the first vessel contains the plurality of nucleic acid fragments from the first plurality of polynucleotides, and wherein the total concentration of the plurality of nucleic acids in the first vessel includes the plurality of nucleic acid fragments from the first plurality of polynucleotides. In some embodiments, the concentration of a fragment having the known wild-type sequence or the known variant sequence is about $10^{-8}$-$10^{-1}$, or about $10^{-1}$ to 99%, of the total concentration of the plurality of nucleic acids.

In some embodiments, the concentration of a fragment having a known wild-type sequence or a known variant sequence in a second vessel is in a range of 10%-0.00001% of the total concentration of the plurality of nucleic acids in the second vessel, wherein the second vessel contains the plurality of nucleic acid fragments from the second plurality of polynucleotides, and wherein the total concentration of the plurality of nucleic acids in the second vessel includes the plurality of nucleic acid fragments from the second plurality of polynucleotides. In some embodiments, the concentration of a fragment having the known wild-type sequence or known variant sequence is about $10^{-8}$-$10^{-1}$, or about $10^{-1}$ to 99%, of the total concentration of the plurality of nucleic acids.

In some embodiments, the method further comprises: measuring the amount of a first sequence of interest contained in the plurality of nucleic acid fragments from the first plurality of polynucleotides, wherein the first sequence of interest includes a first known wild-type sequence, first known variant sequence, or first known aneuploidy variation.

In some embodiments, the method further comprises: measuring the amount of a second sequence of interest contained in the plurality of nucleic acid fragments from the second plurality of polynucleotides, wherein the second sequence of interest includes a second known wild-type sequence, second known variant sequence, or second known aneuploidy variation.

In some embodiments, the method further comprises: diluting the first sequence of interest in the plurality of nucleic acid fragments from the first plurality of polynucleotides to a range of 10%-0.00001% of the total concentration of the plurality of nucleic acids. In some embodiments, the concentration of the first sequence of interest is about $10^{-8}$-$10^{-1}$, or about $10^{-1}$ to 99%, of the total concentration of the plurality of nucleic acids.

In some embodiments, the method further comprises: diluting the second sequence of interest in the plurality of nucleic acid fragments from the second plurality of polynucleotides to a range of 10%-0.00001% of the total concentration of the plurality of nucleic acids. In some embodiments, the concentration of the second sequence of interest is about $10^{-8}$-$10^{-1}$, or about $10^{-1}$ to 99%, of the total concentration of the plurality of nucleic acids.

In some embodiments, the method further comprises: (a) providing single reaction mixture containing an aliquot from the diluted first sequence of interest, wherein the aliquot contains the plurality of nucleic acid fragments from the first plurality of polynucleotides; and (b) appending an oligonucleotide adaptor to one end or both ends of the plurality of nucleic acid fragments from the first plurality of polynucleotides to generate a plurality of tagged fragment polynucleotides, wherein the oligonucleotide adaptor includes (i) at least one or any combination of a universal sequence, including an amplification primer sequence, a sequencing primer sequence, a capture primer sequence and/or a cleavable site, and (ii) at least one unique tag sequence from a repertoire of different unique tag sequences, and (iii) at least one fixed sequence. An aliquot of the diluted first sequence of interest includes a portion or all of the diluted first sequence of interest.

In some embodiments, the method further comprises: amplifying the plurality of tagged fragment polynucleotides to generate a plurality of tagged first fragment amplicons.

In some embodiments, the method further comprises: sequencing at least a portion of the tagged first fragment amplicons thereby generating a plurality of sequencing reads.

In some embodiments, the method further comprises: determining that the first sequence of interest is present in the aliquot from the diluted first sequence of interest at an abundance level of about $10^{-8}$ to about 10%.

In some embodiments, the aliquot from the diluted first sequence of interest contains 1-1000 different variant sequences.

In some embodiments, the method further comprises: mixing the plurality of nucleic acid fragments from the first plurality of polynucleotides with the plurality of nucleic acid fragments from the second plurality of polynucleotides in a single reaction vessel to make a mixed fragments reaction vessel, wherein the first sequence of interest is present in the mixed fragments reaction vessel at a concentration of 10%-0.0001% and the first sequence of interest comprises the first known wild-type sequence, the first known variant sequence, or the first known aneuploidy variation, and wherein the second sequence of interest is present in the mixed fragments reaction vessel at a concentration of 0.0001%-10% and the second sequence of interest comprises the second known wild-type sequence, the second known variant sequence, or the second known aneuploidy variation. In some embodiments, the concentration of the first and/or the second sequence of interest is about $10^{-8}$-$10^{-1}$, or about $10^{-1}$ to 99%, of the total concentration of the plurality of nucleic acids.

In some embodiments, the method further comprises: (a) providing single reaction mixture containing an aliquot from the mixed fragments reaction vessel, wherein the aliquot contains the plurality of nucleic acid fragments from the first plurality of polynucleotides and the plurality of nucleic acid fragments from the second plurality of polynucleotides; and (b) appending an oligonucleotide adaptor to one end or both ends of the plurality of nucleic acid fragments from the first plurality of polynucleotides and the plurality of nucleic acid fragments from the second plurality of polynucleotides to generate a plurality of tagged fragment polynucleotides, wherein the oligonucleotide adaptor includes (i) at least one or any combination of a universal sequence, including an amplification primer sequence, a sequencing primer sequence, a capture primer sequence and/or a cleavable site, and (ii) at least one unique tag sequence from a repertoire of different unique tag sequences, and (iii) at least one fixed sequence. An aliquot from the mixed fragments reaction vessel includes a portion or all of the from the mixed fragments reaction vessel.

In some embodiments, the oligonucleotide adaptor is appended via ligation, primer extension or PCR amplification.

In some embodiments, the oligonucleotide adaptor which is appended via ligation comprises a double-stranded linear adaptor, a stem-looped adaptor or a Y-shaped adaptor.

In some embodiments, the oligonucleotide adaptor which is appended via primer extension or PCR amplification comprises a single-stranded primer having (i) a 3' region that specifically binds a target sequence in the plurality of polynucleotides from the nucleic acid sample, and (ii) a 5' tail having a sequence that is not complementary to a target sequence in the plurality of polynucleotides from the nucleic acids sample. In some embodiments, the 5' tail can contain a unique tag sequence and optionally a sample-specific barcode sequence. In some embodiments, the 5' tail can contain a universal sequence, including at least one or any combination of a universal sequence, including an amplification primer sequence, a sequencing primer sequence, a capture primer sequence and/or a cleavable site.

In some embodiments, the nucleic acid fragments which are generated using any of the fragmenting procedures described in the teachings herein are appended with one or more adaptors carrying a unique randomer tag, for example using a molecular tagging method described in U.S. published application No. 2016/0362748, published Dec. 15, 2016, entitled "Methods, Systems, Compositions, Kits, Apparatus and Computer-Readable Media for Molecular Tagging" which is incorporated by reference in its entirety. In some embodiments, the unique tag sequence can uniquely identify an individual polynucleotide to which it is appended, and distinguish the individual tagged polynucleotide from other tagged polynucleotide in a mixture. In some embodiments, the oligonucleotide adaptor comprises a unique tag sequence from a repertoire of different unique tag sequences. In some embodiments, the repertoire of different unique tag sequences includes $10^4$-$10^9$ different unique sequences. In some embodiments, the unique tag sequence comprises at least one random or degenerate sequence. In some embodiments, the oligonucleotide adaptor comprises at least one fixed sequence that is the same sequence in all of the oligonucleotide adaptors. In some embodiments, the oligonucleotide adaptor comprises a unique tag sequence from a repertoire of different tag sequences and a fixed tag sequence that is the same sequence in all of the oligonucleotide adaptors. In some embodiments, the oligonucleotide adaptor comprises a unique tag sequence from a repertoire of different tag sequences and two or more different fixed tag sequences. In some embodiments, the oligonucleotide adaptor comprises two unique tag sequences from a repertoire of different tag sequences and two or more different fixed tag sequences. In some embodiments, the oligonucleotide adaptor comprises a random sequence flanked on both sides by a fixed sequence, or a fixed sequence flanked on both sides by a random sequence. In some embodiments, the oligonucleotide adaptor comprises two or more different unique tag sequences alternating with two or more fixed tag sequences.

In some embodiments, the oligonucleotide adaptors comprise the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10. In some embodiments, the fixed tag sequences "$(X)_x$" and "$(Y)_y$" are sequence alignment anchors.

In some embodiments, the polynucleotides are appended with a sample-specific barcode that identifies the sample or source from which polynucleotides are derived. The sample-specific barcode can be part of the adaptor containing the unique tag sequence, or can be contained on a separate adaptor. The sample-specific barcode sequence can be appended to the polynucleotide by ligation, primer extension or PCR amplification.

In some embodiments, the method further comprises: amplifying the plurality of tagged fragment polynucleotides to generate a plurality of tagged first fragment amplicons.

In some embodiments, the method further comprises: sequencing at least a portion of the tagged first fragment amplicons thereby generating a plurality of sequencing reads.

In some embodiments, the method further comprises: determining that the first sequence of interest is present in the aliquot from the mixed fragments reaction vessel at an abundance level of about $10^{-8}$ to about 10%.

In some embodiments, the method further comprises: determining that the second sequence of interest is present in the aliquot from the mixed fragments reaction vessel at an abundance level of about $10^{-8}$ to about 10%.

In some embodiments, the aliquot from the mixed fragments reaction vessel contains 1-1000 different variant sequences.

In some embodiments, the aliquot of the control nucleic acid contains about 1-100 ng, or about 1-50 ng, or about 1-25 ng.

In some embodiments, the method further comprises: detecting 0-10 or 0-5 false positive sequencing reads. In some embodiments, the false positive sequencing reads comprises a fragmentation-induced nucleic acid transitions which are selected from a group consisting of C>T, T>C, A>G, and G>A. In some embodiments, the false positive sequencing reads comprises a fragmentation-induced nucleic acid transversions which are selected from a group consisting of, A>T, T>A, C>T, T>C, A>C, C>A, G>T and T>G.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) determining that at least one sequence of interest is present in the aliquot of the test sample at an abundance level of about $10^{-8}$ to about 10%. In some embodiments, the at least one sequence of interest comprises a variant sequence or a wild-type sequence. An aliquot of the test sample includes a portion or all of the test sample.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) detecting 1-10 or 0-5 false positive sequencing reads. An aliquot of the test sample includes a portion or all of the test sample.

In some embodiments, provided are methods for fragmenting nucleic acids (e.g., method for preparing a control nucleic acid), comprising: (a) providing a single reaction mixture containing (i) a first plurality of polynucleotides, (ii) a second plurality of polynucleotides, (iii) at least one nucleic acid damage-mitigating reagent selected from a group consisting of 3-indole-propionic acid, phenylacetic acid, DL-indole-3-lactic acid, 1-methyl-2-oxindole, indole-3-pyruvic acid, indole-3-carboxylic acid, 3-indoleacrylic acid, N-(3-indolylacetyle)-L-alanine, indole lactic acid, indole-3-acetic acid, and (iv) at least one chelating reagent selected from a group consisting of EDTA, EDDHA, EDDS, EDTMP and EGTA; and (b) fragmenting the first plurality of polynucleotides and the second plurality of polynucleotides to generate a fragment mixture comprising a plurality of nucleic acid fragments from the first plurality of polynucleotides and plurality of nucleic acid fragments from the second plurality of polynucleotides.

In some embodiments, the damage-mitigating reagent and the chelating reagent in step (a) reduce fragmentation-induced nucleic acid transitions which are selected from a group consisting of C>T, T>C, A>G, and G>A.

In some embodiments, the damage-mitigating reagent and the chelating reagent in step (a) reduce fragmentation-induced nucleic acid transversions which are selected from a group consisting of, A>T, T>A, C>T, T>C, A>C, C>A, G>T and T>G.

In some embodiments, fragmenting the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transitions C>T, T>C, A>G, and G>A and/or wherein fragmenting the nucleic acid fragments from the first plurality of polynucleotides and the nucleic acid fragments from the second plurality of polynucleotides in the presence of the nucleic acid damage-mitigating reagent and the chelating reagent reduces the number of any one or any combination of nucleic acid transversions A>T, T>A, C>T, T>C, A>C, C>A, G>T and T>G, compared to fragmenting the nucleic acid fragments from the first plurality of polynucleotides and the nucleic acid fragments from the second plurality of polynucleotides in the absence of the nucleic acid damage-mitigating reagent and the chelating reagent.

In some embodiments, the nucleic acid fragments from the first plurality of polynucleotides and the nucleic acid fragments from the second plurality of polynucleotides comprise fragments of about 50-500 bp, or about 100-450 bp, or about 100-200 bp.

In some embodiments, the nucleic acid fragments from the first plurality of polynucleotides contains at least one polynucleotide having a known wild-type sequence, or contains at least one polynucleotide having a known variant sequence or a known aneuploidy variation.

In some embodiments, the nucleic acid fragments from the first plurality of polynucleotides contains 1-1000 different variant sequences.

In some embodiments, the nucleic acid fragments from the second plurality of polynucleotides contains at least one polynucleotide having a known wild-type sequence, or contains at least one polynucleotide having a known variant sequence or a known aneuploidy variation.

In some embodiments, the nucleic acid fragments from the second plurality of polynucleotides contains 1-1000 different variant sequences.

In some embodiments, the nucleic acid fragments from the first plurality of polynucleotides comprise a known amount of the polynucleotide having the wild-type sequence, or a known amount of the polynucleotide having the variant sequence or a known amount of the polynucleotide having the aneuploidy variation.

In some embodiments, the concentration of a fragment having a known wild-type sequence is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of the known wild-type sequence is about $10^{-8}$-$10^{-1}$, or about $10^{-1}$ to 99%, of the total concentration of the plurality of nucleic acids.

In some embodiments, the nucleic acid fragments from the second plurality of polynucleotides comprise a known amount of the polynucleotide having the wild-type sequence, or a known amount of the polynucleotide having the variant sequence or a known amount of the polynucleotide having the aneuploidy variation.

In some embodiments, the concentration of a fragment having a known wild-type sequence is in a range of 10%-0.00001% of the total concentration of the plurality of nucleic acids, wherein the total concentration of the plurality of nucleic acids includes the plurality of nucleic acid fragments from the first plurality of polynucleotides and the plurality of nucleic acid fragments from the second plurality of polynucleotides. In some embodiments, the concentration of known wild-type sequence is about $10^{-8}$-$10^{-1}$, or about $10^{-1}$ to 99%, of the total concentration of the plurality of nucleic acids.

In some embodiments, the method further comprises: measuring the amount of a first sequence of interest contained in the plurality of nucleic acid fragments from the first plurality of polynucleotides, wherein the first sequence of interest includes the known wild-type sequence, the known variant sequence, or the known aneuploidy variation.

In some embodiments, the method further comprises: measuring the amount of a second sequence of interest contained in the plurality of nucleic acid fragments from the second plurality of polynucleotides, wherein the second sequence of interest includes the known wild-type sequence, the known variant sequence, or the known aneuploidy variation.

In some embodiments, the method further comprises: diluting the first sequence of interest in the plurality of nucleic acid fragments from the first plurality of polynucleotides to a range of 10%-0.00001% of the total concentration of the plurality of nucleic acids. In some embodiments, the concentration of the first sequence of interest is about $10^{-8}$-$10^{-1}$, or about $10^{-1}$ to 99%, of the total concentration of the plurality of nucleic acids.

In some embodiments, the method further comprises: diluting the second sequence of interest in the plurality of nucleic acid fragments from the second plurality of polynucleotides to a range of 10%-0.00001% of the total concentration of the plurality of nucleic acids. In some embodiments, the concentration of the second sequence of interest is about $10^{-8}$-$10^{-1}$, or about $10^{-1}$ to 99%, of the total concentration of the plurality of nucleic acids.

In some embodiments, the method further comprises: (a) providing single reaction mixture containing an aliquot of the plurality of nucleic acid fragments from the first plurality of polynucleotides and the plurality of nucleic acid fragments from the second plurality of polynucleotides; and (b) appending an oligonucleotide adaptor to one end or both ends of the plurality of nucleic acid fragments from the first plurality of polynucleotides and the plurality of nucleic acid fragments from the second plurality of polynucleotides to generate a plurality of tagged fragment polynucleotides, wherein the oligonucleotide adaptor includes (i) at least one or any combination of a universal sequence, including an amplification primer sequence, a sequencing primer sequence, a capture primer sequence and/or a cleavable site, and (ii) at least one unique tag sequence from a repertoire of different unique tag sequences, and (iii) at least one fixed sequence. An aliquot of the plurality of nucleic acid fragments includes a portion or all of the plurality of nucleic acid fragments.

In some embodiments, the oligonucleotide adaptor is appended via ligation, primer extension or PCR amplification.

In some embodiments, the oligonucleotide adaptor which is appended via ligation comprises a double-stranded linear adaptor, a stem-looped adaptor or a Y-shaped adaptor.

In some embodiments, the oligonucleotide adaptor which is appended via primer extension or PCR amplification comprises a single-stranded primer having (i) a 3' region that specifically binds a target sequence in the plurality of polynucleotides from the nucleic acid sample, and (ii) a 5' tail having a sequence that is not complementary to a target sequence in the plurality of polynucleotides from the nucleic acids sample. In some embodiments, the 5' tail can contain a unique tag sequence and optionally a sample-specific barcode sequence. In some embodiments, the 5' tail can contain a universal sequence, including at least one or any combination of a universal sequence, including an amplification primer sequence, a sequencing primer sequence, a capture primer sequence and/or a cleavable site.

In some embodiments, the nucleic acid fragments which are generated using any of the fragmenting procedures described in the teachings herein are appended with one or more adaptors carrying a unique randomer tag, for example using a molecular tagging method described in U.S. published application No. 2016/0362748, published Dec. 15, 2016, entitled "Methods, Systems, Compositions, Kits, Apparatus and Computer-Readable Media for Molecular Tagging" which is incorporated by reference in its entirety. In some embodiments, the unique tag sequence can uniquely identify an individual polynucleotide to which it is appended, and distinguish the individual tagged polynucleotide from other tagged polynucleotide in a mixture. In some embodiments, the oligonucleotide adaptor comprises a unique tag sequence from a repertoire of different unique tag sequences. In some embodiments, the repertoire of different unique tag sequences includes $10^4$-$10^9$ different unique sequences. In some embodiments, the unique tag sequence comprises at least one random or degenerate sequence. In some embodiments, the oligonucleotide adaptor comprises at least one fixed sequence that is the same sequence in all of the oligonucleotide adaptors. In some embodiments, the oligonucleotide adaptor comprises a unique tag sequence from a repertoire of different tag sequences and a fixed tag sequence that is the same sequence in all of the oligonucleotide adaptors. In some embodiments, the oligonucleotide adaptor comprises a unique tag sequence from a repertoire of different tag sequences and two or more different fixed tag sequences. In some embodiments, the oligonucleotide adaptor comprises two unique tag sequences from a repertoire of different tag sequences and two or more different fixed tag sequences. In some embodiments, the oligonucleotide adaptor comprises a random sequence flanked on both sides by a fixed sequence, or a fixed sequence flanked on both sides by a random sequence. In some embodiments, the oligonucleotide adaptor comprises two or more different unique tag sequences alternating with two or more fixed tag sequences.

In some embodiments, the oligonucleotide adaptors comprise the structure $(N)_n(X)_x(M)_m(Y)_y$, (i) wherein "N" represents a random tag sequence wherein each base position in the random tag sequence is independently selected from A, G, C or T, and wherein the length "n" is 2-10; (ii) wherein "X" represents a fixed tag sequence that is the same in all of the plurality of tags, and wherein the length "x" is 2-10; (iii) wherein "M" represents a random tag sequence wherein each base position in the random tag sequence is independently selected from A, G, C or T, wherein the random tag sequence "M" differs from the random tag sequence "N", and wherein the length "m" is 2-10; and (iv) wherein "Y" represents a fixed tag sequence that is the same in all of the plurality of tags, wherein the fixed tag sequence of "Y" differs from the fixed tag sequence of "X", and wherein the length "y" is 2-10. In some embodiments, the fixed tag sequences "$(X)_x$" and "$(Y)_y$" are sequence alignment anchors.

In some embodiments, the polynucleotides are appended with a sample-specific barcode that identifies the sample or source from which polynucleotides are derived. The sample-specific barcode can be part of the adaptor containing the unique tag sequence, or can be contained on a separate adaptor. The sample-specific barcode sequence can be appended to the polynucleotide by ligation, primer extension or PCR amplification.

In some embodiments, the method further comprises: amplifying the plurality of tagged fragment polynucleotides to generate a plurality of tagged fragment amplicons.

In some embodiments, the method further comprises: sequencing at least a portion of the tagged fragment amplicons.

In some embodiments, the method further comprises: determining that the first sequence of interest is present in the aliquot at an abundance level of about $10^{-8}$ to about 10%, wherein the first sequence of interest comprises includes the known wild-type sequence, the known variant sequence, or the known aneuploidy variation.

In some embodiments, the method further comprises: determining that the second sequence of interest is present in the aliquot at an abundance level of about $10^{-8}$ to about 10%, wherein the second sequence of interest comprises includes the known wild-type sequence, the known variant sequence, or the known aneuploidy variation.

In some embodiments, the aliquot contains 1-1000 different variant sequences.

In some embodiments, the aliquot of the control nucleic acid contains about 1-100 ng, or about 1-50 ng, or about 1-25 ng.

In some embodiments, the method further comprises: detecting 0-10 or 0-5 false positive sequencing reads. In some embodiments, the false positive sequencing reads comprises a fragmentation-induced nucleic acid transitions which are selected from a group consisting of C>T, T>C, A>G, and G>A. In some embodiments, the false positive sequencing reads comprises a fragmentation-induced nucleic acid transversions which are selected from a group consisting of, A>T, T>A, C>T, T>C, A>C, C>A, G>T and T>G.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) determining that at least one sequence of interest is present in the aliquot of the test sample at an abundance level of about $10^{-8}$ to about 10%. In some embodiments, the at least one sequence of interest comprises a variant sequence or a wild-type sequence. An aliquot of the test sample includes a portion or all of the test sample.

In some embodiments, the method further comprises: comparing the abundance level of the sequence of interest present in an aliquot of a test sample containing a plurality of polynucleotides, wherein the aliquot of the test sample has been subjected to a parallel workflow that includes: (a) appending an oligonucleotide adaptor to one end or both ends of the plurality polynucleotides of the test sample to generate a plurality of tagged fragment polynucleotides; (b) amplifying the plurality of tagged fragment polynucleotides to generate a plurality of tagged fragment amplicons; (c) sequencing at least a portion of the tagged fragment amplicons to generate a plurality of sequencing reads; and (d) detecting 1-10 or 0-5 false positive sequencing reads. An aliquot of the test sample includes a portion or all of the test sample.

In some embodiments, provided are methods, as well as related compositions, kits, and systems, for fragmenting nucleic acids and/or for preparing a control nucleic acid which includes detecting and quantifying the amount structurally damage nucleic acid, base transitions or base transversions resulting from the fragmentation step using art-known methods, including quantitative or semi-quantitative methods such as PCR, digital PCR, digital droplet PCR, fluorometry, electrophoresis, or optical density (e.g., absorbance). In some embodiments, the presence of 8-oxo guanine is detected by employing an ELISA reaction using an anti-8-oxoG antibody (e.g., from Enzo Biosciences). The amount structurally damage nucleic acid, base transitions or base transversions resulting from fragmentation in the presence or absence of at least one nucleic acid damage-mitigating reagent and/or at least one chelating reagent can be compared.

In some embodiments, provided are methods, as well as related compositions, kits, and systems, for fragmenting nucleic acids and/or for preparing a control nucleic acid which includes quantifying the amount of input nucleic acids will be fragmented. In some embodiments, any amount of input nucleic acids is fragmented in the presence of at least one nucleic acid damage-mitigating reagent and/or at least one chelating reagent, including 10 ng-1 ug. The amount of input nucleic acids can be quantitated using any art-known method, including PCR, digital PCR, digital droplet PCR, Qubit™ or RNaseP assay on qPCR.

In some embodiments, provided are systems, as well as related compositions, kits, and methods, for reducing nucleic acid damage and/or for fragmenting nucleic acids and/or for preparing a control nucleic acid, wherein the first and/or the second plurality of polynucleotides, or the plurality of nucleic acid fragments from the first and/or second plurality of polynucleotides, comprise DNA or RNA or recombinant DNA or recombinant RNA.

In some embodiments, the first and/or the second plurality of polynucleotides, or the plurality of nucleic acid fragments from the first and/or second plurality of polynucleotides, comprise linear or circular nucleic acid molecules.

In some embodiments, the first and/or the second plurality of polynucleotides, or the plurality of nucleic acid fragments from the first and/or second plurality of polynucleotides, comprise cell-free nucleic acids from a biological fluid, nucleic acids from a biopsied tissue, nucleic acids from a needle biopsy, or nucleic acids from cells.

In some embodiments, the first and/or the second plurality of polynucleotides, or the plurality of nucleic acid fragments from the first and/or second plurality of polynucleotides, comprise nucleic acids isolated from a tumor, tumor cells or circulating tumor cells.

In some embodiments, the first and/or the second plurality of polynucleotides, or the plurality of nucleic acid fragments from the first and/or second plurality of polynucleotides, comprise genomic DNA or mitochondrial DNA. In some embodiments, the genomic DNA comprises NA12878, NA12891 or NA12892.

In some embodiments, the first and/or the second plurality of polynucleotides, or the plurality of nucleic acid fragments from the first and/or second plurality of polynucleotides, comprise a plurality of nucleic acid vectors, plasmids, phagemids, phasmids or cosmids. In some embodiments, the plurality of nucleic acid vectors, plasmids, phagemids, phasmids or cosmids comprise a known wild-type sequence, a known variant sequence or a known aneuploidy variation. In some embodiments, individual nucleic acid vectors, plasmids, phagemids, phasmids or cosmids within the plurality of nucleic acid vectors, plasmids, phagemids, phasmids or cosmids comprise a different known wild-type sequence, or a different known variant sequence or a different known aneuploidy variation. In some embodiments, a nucleic acid vector, plasmid, phagemid, phasmid or cosmid comprises and extrachromosomal nucleic acid that can replicate in a host cell independent of the host cell's chromosomal nucleic acids. In some embodiments, a nucleic acid vector, plasmid, phagemid, phasmid or cosmid comprises one copy of a known sequence (e.g., wild-type or variant sequence), or multiple copies of a known sequence (e.g., wild-type or variant sequence). The multiple copies of a known sequence comprise the same or different sequences. The multiple copies can be arranged in a tandem manner. The multiple copies of the known sequences can be separated by at least one restriction endonuclease recognition sequence which are the same or different. The multiple copies can be released from the vector, plasmid, phagemid, phasmid or cosmid, by digesting with an appropriate restriction enzyme, and the exact copy number of the released known sequences is predictable. A vector, plasmid, phagemid, phasmid or cosmid that contains tandem copies of known sequences is sometimes referred to as a cassette (U.S. published application No. 2015/0133314, entitled Reagents and Methods for Sequencing, which is incorporated herein by reference in its entirety).

In some embodiments, the first and/or the second plurality of polynucleotides, or the plurality of nucleic acid fragments from the first and/or second plurality of polynucleotides, is isolated from a single cell, a plurality of cells, tissue, cell culture or cell line. In some embodiments, the cell line comprises human GM24385, GM24149, GM24143, GM24385, GM24631 or GM12878.

In some embodiments, the first and/or the second plurality of polynucleotides, or the plurality of nucleic acid fragments from the first and/or second plurality of polynucleotides, is isolated from one or more plants, insects, bacteria, virus or fungus.

In some embodiments, the first and/or the second plurality of polynucleotides, or the plurality of nucleic acid fragments from the first and/or second plurality of polynucleotides, is isolated from any organism including human, canine, feline, bovine, equine, murine, porcine, caprine, lupine, ranine, piscine, simian, or ape.

In some embodiments, the first and/or the second plurality of polynucleotides, or the plurality of nucleic acid fragments from the first and/or second plurality of polynucleotides, is isolated from any organ, including head, neck, brain, breast, ovary, cervix, colon, rectum, endometrium, gallbladder, intestines, bladder, prostate, testicles, liver, lung, kidney, esophagus, pancreas, thyroid, pituitary, thymus, skin, heart, larynx, or other organs.

In some embodiments, the first and/or the second plurality of polynucleotides, or the plurality of nucleic acid fragments from the first and/or second plurality of polynucleotides, is isolated from a biological fluid obtained from blood, serum, plasma, saliva, sputum, sweat, tears, lavage fluid, amniotic fluid (e.g., from a pregnant female), cerebrospinal fluid, ascites, urine, stool, feces, or semen.

In some embodiments, the first and/or the second plurality of polynucleotides, or the plurality of nucleic acid fragments from the first and/or second plurality of polynucleotides, is isolated from a formalin fixed paraffin-embedded (FFPE) sample.

In some embodiments, the first and/or the second plurality of polynucleotides, or the plurality of nucleic acid fragments from the first and/or second plurality of polynucleotides, is isolated from water, soil or food.

In some embodiments, the first and/or the second plurality of polynucleotides, or the plurality of nucleic acid fragments from the first and/or second plurality of polynucleotides, is isolated from a healthy source, a diseased source or an infected source.

In some embodiments, the first and/or the second plurality of polynucleotides, or the plurality of nucleic acid fragments from the first and/or second plurality of polynucleotides, comprise at least one wild-type sequence, variant sequence, allelic sequence, or mutant sequence.

In some embodiments, the variant sequence comprises a single nucleotide polymorphism (SNP), one or more multiple nucleotide polymorphisms (MNPs), substitution, insertion, deletion, rearrangement, aberrant splice junction, truncation, transversion, non-sense mutation, gene fusion, duplication, inversion, repeat polymorphism, or homopolymer.

In some embodiments, the variant sequence is associated with a genetic disease, hereditary disease, or infection. In some embodiments, the variant sequence comprises a copy number variation, aneuploidy, partial aneuploidy, or polyploidy. In some embodiments, the variant sequence is associated with an aneuploidy condition.

In some embodiments, provided are systems, as well as related compositions, kits, and methods, for reducing nucleic acid damage and/or for fragmenting nucleic acids and/or for preparing a control nucleic acid, wherein the first and/or the second plurality of polynucleotides, or the plurality of nucleic acid fragments from the first and/or second plurality of polynucleotides, comprises at least one of the genes from the catalog of somatic cancer mutations in the COSMIC database (e.g., see http://cancer.sanger.ac.uk/cosmic), or comprises at least one of the genes from a list of Oncology Hotspot mutant sequences (e.g., from Acrometrix, catalog No. 969056, FRM0016300, Rev. A.00, Thermo Fisher Scientific, Inc.), and/or is selected from the following list: ABI1; ABL1; ABL2; ACSL3; ACSL6; AFF1; AFF3; AFF4; AKAP9; AKT1; AKT2; ALK; APC; ARHGAP26; ARHGEF12; ARID1A; ARNT; ASPSCR1; ASXL1; ATF1; ATIC; ATM; AXIN2; BAP1; BARD1; BCAR3; BCL10;

BCL11A; BCL11B; BCL2; BCL3; BCL6; BCL7A; BCL9; BCR; BIRC3; BLM; BMPR1A; BRAF; BRCA1; BRCA2; BRD3; BRD4; BRIP1; BUB1B; CARD11; CARS; CASC5; CBFA2T3; CBFB; CBL; CBLB; CBLC; CCDC6; CCNB11P1; CCND1; CCND2; CD74; CD79A; CDC73; CDH1; CDH11; CDK4; CDK6; CDKN2A; CDKN2B; CDKN2C; CDX2; CEBPA; CEP110; CHEK1; CHEK2; CHIC2; CHN1; CIC; CIITA; CLP1; CLTC; CLTCL1; COL1A1; CREB1; CREB3L2; CREBBP; CRTC1; CRTC3; CSF1R; CTNNB1; CXCR7; CYLD; CYTSB; DCLK3; DDB2; DDIT3; DDR2; DDX10; DDXS; DDX6; DEK; DGKG; DICER1; DNMT3A; EEF1B2; EGFR; EIF4A2; ELF4; ELL; ELN; EML4; EP300; EPS15; ERBB2; ERBB4; ERC1; ERCC2; ERCC3; ERCC4; ERCC5; ERG; ETV1; ETV4; ETV5; ETV6; EWSR1; EXT1; EXT2; EZH2; FAM123B; FANCA; FANCC; FANCD2; FANCE; FANCF; FANCG; FAS; FBXW7; FCRL4; FGFR1; FGFR10P; FGFR2; FGFR3; FH; FIP1L1; FLCN; FLI1; FLT1; FLT3; FNBP1; FOXL2; FOXO1; FOXO3; FOXO4; FOXP1; FUS; GAS7; GATA1; GATA2; GATA3; GMPS; GNAQ; GNAS; GOLGA5; GOPC; GPC3; GPHNGPR124; HIM; HIST1H4I; HLF; HNF1A; HNRNPA2B1; HOOK3; HOXA11; HOXA13; HOXA9; HOXC11; HOXC13; HOXD13; HRAS; HSP90AA1; HSP90AB1; IDH1; IDH2; IKZF1; IL2; IL21R; IL6ST; IRF4; ITGA10; ITGA9; ITK; JAK1; JAK2; JAK3; KDM5A; KDM5C; KDM6A; KDR; KDSR; KIAA1549; KIT; KLF6; KLK2; KRAS; KTN1; LASP1; LCK; LCP1; LHFP; LIFR; LMO2; LPP; MAF; MALT1; MAML2; MAP2K1; MAP2K4; MDM2; MDM4; MECOM; MEN1; MET; MITF; MKL1; MLH1; MLL; MLLT1; MLLT10; MLLT3; MLLT4; MLLT6; MN1; MPL; MRE11A; MSH2; MSH6; MSI2; MSN; MTCP1; MTOR; MUC1; MYB; MYC; MYCL1; MYCN; MYH11; MYH9; MYST3; MYST4; NACA; NBN; NBPF10, NCOA1; NCOA2; NCOA4; NEK9; NF1; NF2; NFE2L2; NFKB2; NIN; NKX2-1; NLRP1; NONO; NOTCH1; NOTCH2; NPM1; NR4A3; NRAS; NSD1; NTRK1; NTRK3; NUMA1; NUP214; NUP98; OLIG2; OMD; PAFAH1B2; PALB2; PATZ1; PAX3; PAX5; PAX7; PAX8; PBRM1; PBX1; PCM1; PDE4DIP; PDGFB; PDGFRA; PDGFRB; PER1; PHOX2B; PICALM; PIK3CA; PIK3R1; PIM1; PLAG1; PML; PMS1; PMS2; POU2AF1; POU5F1; PPARG; PPP2R1A; PRCC; PRDM16; PRF1; PRF19; PRKAR1A; PRRX1; PSIP1; PTCH1; PTEN; PTPN11; RABEP1; RAD50; RAD51L1; RAF1; RANBP17; RAP1GDS1; RARA; RB1; RBM15; RECQL4; REL; RET; RHOH; RNF213; ROS1; RPN1; RPS6KA2; RSBN1L; RUNX1; RUNX1T1; SBDS; SDHAF2; SDHB; SETD2; SFPQ; SFRS3; SH3GL1; SLC6A18; SLC45A3; SMAD4; SMARCA4; SMARCB1; SMO; SOCS1; SRC; SRGAP3; SS18; SS18L1; STIL; STK11; STK36; SUFU; SYK; TAF15; TAF1L; TAL1; TAL2; TCF12; TCF3; TCL1A; TET1; TET2; TEX14; TFE3; TFEB; TFG; TFRC; THRAP3; TLX1; TLX3; TMPRSS2; TNFAIP3; TOP1; TP53; TPM3; TPM4; TPR; TRIM27; TRIM33; TRIP11; TSC1; TSC2; TSHR; USP6; VHL; WAS; WASH3P; WHSC1L1; WRN; WT1; XPA; XPC; ZBTB16; ZMYM2; ZNF331; ZNF384; and ZNF521.

In some embodiments, provided are methods, as well as related compositions, kits, and systems, for reducing nucleic acid damage and/or for fragmenting nucleic acids and/or for preparing a control nucleic acid, which includes at least one washing step. The washing step can be conducted at any time during the fragmentation procedures described by the teachings herein. In some embodiments, a washing step can remove excess or unreacted components of the nucleic acid synthesis (e.g., amplification) or enrichment reactions.

In some embodiments, provided are methods, as well as related compositions, kits, and systems, for reducing nucleic acid damage and/or for fragmenting nucleic acids and/or for preparing a control nucleic acid, which includes subjecting the nucleic acid fragments to any size-selection procedure to obtain fragments having any desired size range. In some embodiments, nucleic acid fragments are not size-selected. A nucleic acid size selection method includes without limitation: solid phase adherence or immobilization; electrophoresis, such as gel electrophoresis; and chromatography, such as HPLC and size exclusion chromatography. A solid phase adherence/immobilization methods typically involves micro paramagnetic beads coated with a chemical functional group that interacts with nucleic acids under certain ionic strength conditions with or without polyethylene glycol or polyalkylene glycol.

Examples of solid phase adherence/immobilization methods include but are not limited to: SPRI (Solid Phase Reversible Immobilization) beads from Agencourt (see Hawkins 1995 Nucleic Acids Research 23:22) which are carboxylate-modified paramagnetic beads; MAGNA PURE magnetic glass particles (Roche Diagnostics, Hoffmann-La Roche Ltd.); MAGNESIL magnetic bead kit from Promega; BILATEST magnetic bead kit from Bilatec AG; MAGTRATION paramagnetic system from Precision System Science, Inc.; MAG BIND from Omega Bio-Tek; MAGPREP silica from Merck/Estapor; SNARe DNA purification system from Bangs; and CHEMAGEN M-PVA beads from CHEMAGEN.

In some embodiments, size-selected nucleic acid fragments are about 50 base pairs in length to about 3000 base pairs in length, or 50-2000 base pairs in length, or about 50-1500 base pairs in length, or about 50-1000 base pairs in length, or about 50-700 base pairs in length. In some embodiments, size-selected nucleic acid fragments are about 1000-2000 base pairs in length, or about 100-1000 base pairs in length, or about 100-500 base pairs in length, or about 100-250 base pairs in length; or about 50-150 base pairs in length. In some embodiments, size-selected nucleic acid fragments are about 1-5 kb, or about 5-10 kb, or about 10-25 kb, or about 25-50 kb, or longer.

In some embodiments, provided are methods, as well as related compositions, kits, and systems, for reducing nucleic acid damage and/or for fragmenting nucleic acids and/or for preparing a control nucleic acid, which includes subjecting the nucleic acid fragments to enzymatic repairing procedures. Nucleic acid fragments include a first end and a second end. A fragmenting step can generate first ends, second ends, or internal portions, having undesirable features, such as nicks, overhang ends, ends lacking a phosphorylated end, ends having a phosphorylated end, or nucleic acid fragments having apurinic or apyrimidinic residues. In some embodiments, enzymatic reactions are conducted to repair one or more ends or internal portions (e.g., "end repairing" or "repairing the ends" or "repair"). In some embodiments, enzymatic reactions are conducted to convert overhang ends to blunt ends, or to phosphorylate or de-phosphorylate the 5' end of a strand, or to close nicks, to repair oxidized purines or pyrimidines, to repair deaminated cytosines, or to hydrolyze the apurinic or apyrimidinic residues. In some embodiments, repairing or end-repairing nucleic acid fragments includes contacting nucleic acid fragments, or contacting a plurality of first ends and/or second ends with: an enzyme to close single-stranded nicks in duplex DNA (e.g., T4 DNA ligase); an enzyme to phosphorylate the 5' end of at least one strand of a duplex DNA (e.g., T4 polynucleotide kinase); an enzyme to remove a 5' or 3'phosphate (e.g., any phosphatase enzyme, such as calf intestinal alkaline phosphatase, bacterial alkaline phosphatase, shrimp alkaline phosphatase, Antarctic phosphatase, and placental alkaline phosphatase); an enzyme to remove 3' overhang ends (e.g., DNA polymerase I, Large (Klenow) fragment, T4 DNA polymerase, mung bean nuclease); an enzyme to fill-in 5' overhang ends (e.g., T4 DNA polymerase, Tfi DNA polymerase, Tli DNA polymerase, Taq DNA polymerase, Large (Klenow) fragment, phi29 DNA polymerase, Mako DNA polymerase (Enyzmatics, Beverly, Mass.), or any heat-stable or heat-labile DNA polymerase); an enzyme to remove 5' overhang ends (e.g., Sl nuclease); an enzyme to remove 5' or 3' overhang ends (e.g., mung bean nuclease); an enzyme to hydrolyze single-stranded DNA (e.g., nuclease P1); an enzyme to remove both strands of double-stranded DNA (e.g., nuclease Bal-31); and/or an enzyme to remove an apurinic or apyrimidinic residue (e.g., endonuclease IV). In some embodiments, the polymerases can have exonuclease activity, or have a reduced or lack exonuclease activity.

A repairing or end-repairing reaction can be supplemented with additional repairing enzymes in any combination and in any amount, including: endonuclease IV (apurinic-apyrimidinic removal), Bst DNA polymerase (5'>3' exonuclease for nick translation), formamidopyrimidine DNA glycosylase (FPG) (e.g., base excision repair for oxidize purines), uracil DNA glycosylase (uracil removal), T4 endonuclease V (pyrimidine removal) and/or endonuclease VIII (removes oxidized pyrimidines). In some embodiments, a repairing or end-repairing reaction is conducted in the presence of appropriate co-factors, including dNTPs, NAD, $(NH_4)SO_4$, KCl, and/or $MgSO4$. In some embodiments, the additional repairing enzymes are included in a repair or end-repairing reaction at any concentration, including: about 0.1-1 U/uL, or about 1-2 U/uL, or about 2-3 U/uL, or about 3-4 U/uL, or about 5 U/uL, or about 5-10 U/uL, or about 10-15 U/uL, or about 15-20 U/uL, or more.

In some embodiments, a repairing or end-repairing step is performed in the presence of appropriate buffers and/or nucleotides, and at an appropriate pH and temperature(s). A repairing or end-repairing step can be conducted in the presence of a nucleic acid damage mitigating composition.

In some embodiments, provided are methods, as well as related compositions, kits, and systems, for reducing nucleic acid damage and/or for fragmenting nucleic acids and/or for preparing a control nucleic acid, which includes subjecting the nucleic acid fragments to an enzymatic tailing reaction. Adding a nucleotide tail to a first end and/or a second end of a nucleic acid fragment may be desirable. In some embodiments, a DNA polymerase is used to add one or more non-template nucleotides to a 3' end of a nucleic acid strand. In some embodiments, a non-proofreading DNA polymerase is used to add a single non-template A-residue to a 3' end a of a nucleic acid strand. In some embodiments, a DNA polymerase is a Taq DNA polymerase (or a derivative thereof). In some embodiments, DNA polymerases having proofreading activity are used to add a single non-template 3' A-tail. In some embodiments, a DNA polymerase is a Tfi (exo-) DNA polymerase, large (Klenow) fragment (3'>5' exo minus), or derivative polymerases thereof. In some embodiments, T4 DNA polymerase (e.g., exo-) is used to add a non-template, single nucleotide residue to a 3' end of a nucleic acid strand.

In some embodiments, provided are methods, as well as related compositions, kits, and systems, for reducing nucleic acid damage and/or for fragmenting nucleic acids and/or for preparing a control nucleic acid, which includes appending at least one oligonucleotide adaptor to one or both ends of control nucleic acids.

In some embodiments, an adaptor can include at least one tag (e.g., at least one randomer tag).

In some embodiments, polynucleotides are joined or appended to at least one adaptor, or lack any adaptor. In some embodiments, one or more adaptors is joined to a polynucleotide by ligation.

In some embodiments, an adaptor comprises a nucleic acid, including DNA, RNA, RNA/DNA molecules, or analogs thereof. In some embodiments, an adaptor can include one or more deoxyribonucleoside or ribonucleoside residues. In some embodiments, an adaptor is single-stranded or double-stranded nucleic acids, or can include single-stranded and/or double-stranded portions. In some embodiments, an adaptor can have any structure, including linear, hairpin, forked (Y-shaped), or stem-loop. For example, Y-shaped adaptors can include a first oligonucleotide having one end portion hybridized to an end portion of a second oligonucleotide to form a duplex stem portion, and the other end portions of the first and second oligonucleotides are not hybridized to each other. Examples of Y-shaped adaptors include U.S. Pat. No. 8,563,478 (Gormley), U.S. Pat. No. 8,053,192 (Bignell), U.S. Pat. No. 7,741,463 (Gormley), U.S. Pat. No. 8,182,989 (Bignell), U.S. Pat. No. 6,287,825 (Weissman), U.S. Pat. No. 8,420,319 (Mikawa) and U.S. Pat. No. 7,993,842 (McKernan).

Optionally, a linear, hairpin, stem-looped, or Y-shaped adaptor contains at least one tag sequence (e.g., at least one randomer tag sequence). For example the stem portion of the hairpin, stem-looped or Y-shaped adaptor contains at least one tag (e.g., at least one randomer tag). Examples of Y-shaped adaptors used for molecular tagging methods can be found in U.S Application Publication Nos. 2015/0044687; 2015/0031559; 2014/0155274; 2014/0227705; and International Publication Nos. WO 2013/181170 and WO 2015/100427.

In some embodiments, an adaptor can have any length, including fewer than 10 bases in length, or about 10-20 bases in length, or about 20-50 bases in length, or about 50-100 bases in length, or longer.

In some embodiments, an adaptor can have any combination of blunt end(s) and/or sticky end(s). In some embodiments, at least one end of an adaptor is compatible with at least one end of a nucleic acid fragment. In some embodiments, a compatible end of an adaptor is joined to a compatible end of a nucleic acid fragment. In some embodiments, an adaptor can have a 5' or 3' overhang end.

In some embodiments, an adaptor can have a 5' or 3' overhang tail. In some embodiments, the tail is any length, including 1-50 or more nucleotides in length.

In some embodiments, an adaptor can include an internal nick. In some embodiments, an adaptor can have at least one strand that lacks a terminal 5' phosphate residue. In some embodiments, an adaptor lacking a terminal 5' phosphate residue is joined to a nucleic acid fragment to introduce a nick at the junction between the adaptor and the nucleic acid fragment.

In some embodiments, an adaptor can include a nucleotide sequence that is identical or complementary to any portion of the polynucleotide, capture primer, fusion primer, solution-phase primer, amplification primer, or a sequencing primer.

In some embodiments, the adaptor can include an oligo-dA, oligo-dT, oligo-dC, oligo-dG or oligo-U sequences.

In some embodiments, an adaptor can include a unique identifier sequence (e.g., barcode sequence). In some embodiments, a plurality of barcoded adaptors (e.g., plurality of different barcoded adaptors) is used for constructing a multiplex library of polynucleotides. In some embodiments, barcoded adaptors are appended to a polynucleotide and used for sorting or tracking the source of the polynucleotide. For example, a population of polynucleotides can be appended to a common barcoded adaptor which identifies the polynucleotides as being obtained from a common source. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences.

In some embodiments, an adaptor can include degenerate sequences. In some embodiments, an adaptor can include one or more inosine residues.

In some embodiments, an adaptor can include at least one scissile linkage. In some embodiments, the scissile linkage is susceptible to cleavage or degradation by an enzyme or chemical compound. Optionally, an adaptor includes at least one uracil base. In some embodiments, an adaptor can include at least one phosphorothiolate, phosphorothioate, and/or phosphoramidate linkage. For example, a tag containing at least one uracil base is cleavable with uracil DNA glycosylase (UDG) and formamidopyrimidine DNA glycosylase (Fpg).

In some embodiments, an adaptor can include any type of restriction enzyme recognition sequence, including type I, type II, type IIs, type IIB, type III, type IV restriction enzyme recognition sequences, or recognition sequences having palindromic or non-palindromic recognition sequences.

In some embodiments, an adaptor can include a cell regulation sequences, including a promoter (inducible or constitutive), enhancers, transcription or translation initiation sequence, transcription or translation termination sequence, secretion signals, Kozak sequence, cellular protein binding sequence, and the like.

In some embodiments, provided are methods, as well as related compositions, kits, and systems, for reducing nucleic acid damage and/or for fragmenting nucleic acids and/or for preparing a control nucleic acid, which includes appending at least one oligonucleotide adaptor to one or both ends of fragmented nucleic acids that are generated by any method described by the teachings herein. In some embodiments, an oligonucleotide adaptor comprises at least one unique tag (e.g., a randomer tag) which includes at least one random sequence and at least one fixed sequence, or comprises a random sequence flanked on both sides by a fixed sequence, or comprises a fixed sequence flanked on both sides by a random sequence. In some embodiments, a randomer tag contains different random tag sequences alternating with fixed tag sequences. In some embodiments, a randomer tag contains two or more different random tag sequences alternating with two or more fixed tag sequences. In some embodiments, a randomer tag comprises 3 random sequences alternating with 3 fixed sequences, or 4 random sequences alternating with 4 fixed sequences. One skilled in the art will recognize that a randomer tag can include any number of random sequence units alternating with any number of fixed sequence units.

In some embodiments, a fixed sequence within the randomer tag comprises 1-20 or more nucleotides, or analogs thereof. In some embodiments, a random sequence within a randomer tag comprises 1-20 or more nucleotides, or analogs thereof. In some embodiments, each position within a random sequence of a randomer tag is a nucleotide selected from A, T, G, C, I, U, or analogs thereof.

The random sequence within a randomer tag is represented by "N", and the fixed sequence is represented by "X". The randomer tag can include a fixed sequence that is 2-2000 nucleotides or base-pairs in length. The randomer tag can include a random sequence that is 2-2000 nucleotides or base-pairs in length. Thus, a randomer tag can be represented by $N_1N_2N_3X_1X_2X_3$ or by $N_1N_2N_3X_1X_2X_3N_4N_5N_6X_4X_5X_6$. Optionally, the randomer tag can have a random sequence in which some or all of the nucleotide positions can be randomly selected from a group consisting of A, G, C, T, U and I. For example, a nucleotide for each position within a random sequence can be independently selected from any one of A, G, C, T, U or I, or can be selected from a subset of these six different types of nucleotides. Optionally, a nucleotide for each position within a random sequence can be independently selected from any one of A, G, C or T. In some embodiments, the randomer tag comprises the sequence 5'-NNNACTNNNTGA-3' (SEQ ID NO:1), where "N" represents a position within the random sequence that is generated randomly from A, G, C or T. The number of possible distinct randomer tags is calculated to be $4^6$ (or 4^6) is about 4096, and the number of possible different combinations of two randomer tags is $4^{12}$ (or 4^12) is about 16.78 million. In some embodiments, the fixed sequences within the randomer tag sequence can serve as a sequence alignment anchor that is used to generate error-corrected sequencing data, including generating a family of error-corrected sequencing reads. In some embodiments, the randomer tag sequence is not used to correct any sequencing read, but instead, the candidate sequencing read that contains an error (e.g., an error in the randomer tag sequence) is discarded.

An advantage of performing a molecular tagging procedure using randomer tags that contain alternating unit sequences of fixed and random sequences, is that the randomer tag sequence can be used for error-correction of the sequencing reads (e.g., error-correction of a family of sequencing reads). For example, the candidate sequencing reads can be grouped into families based on a common randomer tag sequence. The fixed sequences within the randomer tag sequences can be used as a sequence alignment anchor to impose a strict requirement that all members of any given tag family must contain the length, sequence and spacing that is identical to a reference sequence of the fixed sequences. The candidate sequencing reads that do not meet this requirement may be removed from further analysis. For example, in a reference randomer tag having the sequence 5'-NNNACTNNNTGA-3' (SEQ ID NO:1), the length, sequence and spacing of the two fixed sequences 5'-ACT-3' and 5'-TGA-3' can be used as sequence alignment anchors for comparison with the tag sequence portion of a candidate sequencing read. If the tag sequence portion of the candidate sequencing read does not match the length, sequence and spacing of the two fixed sequences, then the candidate sequencing read may be discarded. This type of comparison with a randomer tag sequence, and decision to retain or discard a sequencing read, can be applied to any candidate sequencing read. The candidate sequencing reads that do not carry a match for the fixed sequences will likely correspond to polynucleotide products of primer extension or amplification having spurious errors that are introduced by polymerase-mediated nucleotide mis-incorporation or strand slippage. Strand slippage may result from secondary structure formation (e.g., loop formation) of the nascent strand or the template strand during primer extension (or amplification). Thus, the fixed sequences within the randomer tag sequence can serve as a sequence alignment anchor that is used to generate error-corrected sequencing data, including generating a family of error-corrected sequencing reads. A molecular tagging procedure which uses tags that lack alternating fixed and random sequences cannot identify sequencing reads carrying errors in the tag region, and therefore cannot generate error-corrected sequencing data in this manner.

In some embodiments, the reference sequence of a randomer tag is used to correct the sequence of a randomer tag in a candidate sequencing read. For example, if a candidate sequencing read shows that a randomer tag sequence is 5'-NNNACTNNNTGC-3' (SEQ ID NO:2), and the reference sequence is known to be 5'-NNNACTNNNTGA-3' (SEQ ID NO:1), then an error-correction algorithm would be applied to change the erroneous base from C to A, to yield an error-corrected sequencing read which is 5'-NN-NACTNNNTGA-3' (SEQ ID NO:1). In some embodiments, the randomer tag sequence is not used to correct any sequencing read, but instead, the candidate sequencing read that contains an error (e.g., an error in the randomer tag sequence) is discarded.

Another advantage of using randomer tags having more than one unit of a random sequence, is that a population of randomer tags will provide enough sequence diversity to serve as a substantially non-depleting population of unique tag sequences. The presence of more than one random sequence increases the diversity of a repertoire of randomer tag sequences. The number of possible unique randomer tags will be dictated by the length of the random sequence and the number of possible different nucleotide bases that can be used to generate the random sequence, along with the length of the fixed sequence. Additionally, the overall length of a randomer tag, which contains alternating fixed/random sequences, can be minimized to reduce the amount of time and reagents needed to sequence one or both tags and the target sequence, while enabling error-corrected sequencing data.

In some embodiments, provided are kits, comprising at least one aliquot of fragmented nucleic acids prepared using any of the methods described herein. In some embodiments, kits also include at least two components or reagents used to generate the tagged nucleic acids as described in the present teachings. For example, a kit contains any combination of at least two of the following reagents: a plurality of randomer tags in the form of double-stranded adaptors or single-stranded tailed primers or both, enzymes (e.g., polymerases and/or ligases), nucleotides, divalent cations, binding partners, and/or buffer(s). Optionally, a kit also contains target nucleic acids to be used as positive or negative control polynucleotides (e.g., any of the control nucleic acids described herein). A kit contains a plurality of randomer tags which comprise oligonucleotides having at least two random sequences alternating with at least two fixed sequences. The polymerases and ligases include recombinant, fusion, mutant, heat-stable or heat labile forms. The nucleotides include compounds having structures the same as or similar to naturally-occurring nucleotides, or nucleotide analogs having derivatized base, sugar and/or phosphate groups, or labeled or non-labeled nucleotides. The divalent cations include magnesium, manganese and/or calcium. The binding partners include biotin and avidin-like compounds, such as avidin or streptavidin. The buffer(s) comprise a source of ions, such as KCl, K-acetate, $NH_4$-acetate, K-glutamate, $NH_4Cl$, or ammonium sulfate. The buffer(s) includes Tris, Tricine, HEPES, MOPS, ACES, MES, or inorganic buffers such as phosphate or acetate-based buffers which can provide a pH range of about 4-12. The buffer(s) include chelating agents such as EDTA or EGTA. The buffer(s) include dithiothreitol (DTT), glycerol, spermidine, and/or BSA (bovine serum albumin). The buffer(s) includes ATP.

In some embodiments, provided are methods, as well as related compositions, kits, and systems, for reducing nucleic acid damage and/or for fragmenting nucleic acids and/or for preparing a control nucleic acid, which include use of at least one nucleotide. In some embodiments, the nucleotides include one type, or a mixture of different types of nucleotides. A nucleotide comprises any compound that can bind selectively to, or can be polymerized by, a polymerase. Typically, but not necessarily, selective binding of the nucleotide to the polymerase is followed by polymerization of the nucleotide into a nucleic acid strand by the polymerase. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain is attached to any carbon of a sugar ring, such as the 5' carbon. The phosphorus chain can be linked to the sugar with an intervening O or S. In some embodiments, one or more phosphorus atoms in the chain is part of a phosphate group having P and O. In some embodiments, the phosphorus atoms in the chain is linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In some embodiments, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281.

Some examples of nucleotides include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. In some embodiments, a nucleotide can include a purine or pyrimidine base, including adenine (A), guanine (G), cytosine (C), thymine (T), uracil (U) or inosine (I). In some embodiments, a nucleotide includes deoxyadenosine triphosphate (dATP), deoxyguanosine triphosphate (dGTP), deoxycytidine triphosphate (dCTP), deoxythymidine triphosphate (dTTP) and deoxyuridine triphosphate (dUTP).

In some embodiments, the nucleotide is unlabeled. In some embodiments, the nucleotide comprises a label and referred to herein as a "labeled nucleotide". In some embodiments, the label is in the form of a fluorescent dye attached to any portion of a nucleotide including a base, sugar or any intervening phosphate group or a terminal phosphate group, i.e., the phosphate group most distal from the sugar.

In some embodiments, the nucleotide is a terminator nucleotide. In some embodiments, the terminator nucleotide will, once incorporated, inhibit or block further nucleotide incorporations at the 3' end of the nucleic acid molecule. The terminator nucleotide includes a terminator group (also referred to as a terminator moiety or a blocking moiety or blocking group) that confers the ability to inhibit or block further nucleotide incorporations. In some embodiments, the terminator nucleotides is operably linked to at least one terminator group or moiety. In some embodiments, at least one terminator group is operably linked to any portion of the base, sugar (e.g., 2' or 3' position), phosphate group or any phosphate in the phosphate chain. In some embodiments, the terminator group is neutralized, cleaved, or otherwise removed from the terminator nucleotide via suitable treatments. In some embodiments, neutralization, cleavage or removal of the terminator group can permit subsequent nucleotide incorporations to occur. In some embodiments, the non-extendible end is converted to an extendible end via cleavage, neutralization or removal of the terminator group. In some embodiments, the terminator group cannot be neutralized, cleaved, or otherwise removed from the terminator nucleotide via suitable treatments (e.g., non-reversible terminator nucleotides). Examples of terminator nucleotide can be found in U.S. Pat. Nos. 7,057,026; 7,566,537; 7,785, 796; 8,158,346; 7,541,444; 7,057,026; 7,592,435; 7,414, 116; 7,427,673; 8,399,188; 7,713,698; 7,790,869; 8,088, 575; 7,635,578; and 7,883,869; and in PCT Application No. PCT/US2016/023139, filed Mar. 18, 2016, which are all expressly incorporated herein by reference as if set forth in full.

In some embodiments, provided are methods, as well as related compositions, kits, and systems, for reducing nucleic acid damage and/or for fragmenting nucleic acids and/or for preparing a control nucleic acid, include a nucleic acid amplification reaction includes a polymerase chain reaction (PCR) (U.S. Pat. Nos. 4,683,195 and 4,683,202 both granted to Mullis), ligase chain reaction (LCR) (Barany 1991 Proceedings National Academy of Science USA 88:189-193; Barnes 1994 Proceedings National Academy of Science USA91:2216-2220), or isothermal self-sustained sequence reaction (Kwoh 1989 Proceedings National Academy of Science USA 86:1173-1177; WO 1988/10315; and U.S. Pat. Nos. 5,409,818, 5,399,491, and 5,194,370), or recombinase polymerase amplification (RPA) (U.S. Pat. No. 5,223,414 to Zarling, U.S. Pat. Nos. 5,273,881 and 5,670,316 both to Sena, and U.S. Pat. Nos. 7,270,981, 7,399,590, 7,435,561, 7,666,598, 7,763,427, 8,017,339, 8,030,000, 8,062,850, and 8,071,308).

In some embodiments, provided are methods, as well as related compositions, kits, and systems, for reducing nucleic acid damage and/or for fragmenting nucleic acids and/or for preparing a control nucleic acid, includes sequencing a control nucleic acid on a massively parallel sequencing procedure including sequencing by oligonucleotide probe ligation and detection (e.g., SOLiD™ from Life Technologies, WO 2006/084132), probe-anchor ligation sequencing (e.g., Complete Genomics or Polonator™), sequencing-by-synthesis (e.g., Genetic Analyzer™ and HiSeq™ from Illumina (Bentley 2006 Current Opinion Genetics & Development 16:545-552; and Bentley, et al., 2008 Nature 456:53-59; and U.S. Pat. No. 7,566,537)), pyrophosphate sequencing (e.g., Genome Sequencer FLX™ from 454 Life Sciences (U.S. Pat. Nos. 7,211,390, 7,244,559 and 7,264, 929)), ion-sensitive sequencing (e.g., Personal Genome Machine (Ion PGM™) and Ion Proton™ Sequencer, both from Ion Torrent Systems, Inc.), and single molecule sequencing platforms (e.g., Heliscope™ from Helicos).

In some embodiments, provided are methods, as well as related compositions, kits, and systems, for reducing nucleic acid damage and/or for fragmenting nucleic acids and/or for preparing a control nucleic acid, which includes sequencing control nucleic acids prepared by any of the methods described herein. In some embodiments, a sequencing platform that employs sequence-by-synthesis includes attaching a plurality of polynucleotides to a support (e.g., immobilized polynucleotides). The control nucleic acids can include an adaptor having a universal capture sequence (e.g., universal amplification sequence), and the support can include capture primers attached thereon. The control nucleic acids can be deposited onto the support. The control nucleic acids can be attached to the support by binding/hybridizing the universal capture sequence of the control nucleic acids to the capture primer on the support. The plurality of control nucleic acids can be covalently attached to the support via the bridge amplification reaction described herein. The support can be a part of a flowcell, and the support includes a substantially planar surface, grooves or a plurality of wells (e.g., microwells or nanowells) arranged in an array. A sequencing reaction site includes any site on the support where a sequencing reaction is conducted. A plurality of sequencing reaction sites can be located at any location on the planar surface, on any region of the grooves, or within any of the wells. Sequencing primers can be hybridized to the plurality of the immobilized control nucleic acids. An aqueous solution that contains one, two, three, four or more, types of nucleotides (e.g., deoxyribose triphosphate nucleotides) can be flowed onto the plurality of immobilized control nucleic acids, and in the presence of a polymerase that binds the polynucleotides and catalyzes nucleotide incorporation, the sequencing reaction begins. A nucleotide that is complementary to template strand is incorporated onto the primer, an optional wash step removes non-incorporated nucleotides, and the identity of the incorporated nucleotide is determined. In some embodiments, the nucleotides in the flow are attached to an optically-detectable label. For example, the different types of nucleotides (e.g., A, G, C and T) can be attached to a different label that differentiates one type of nucleotide from the other types. The optically-detectable label can be attached to the base of the nucleotides. The different types of nucleotides can be attached to a blocking moiety that confers the ability to inhibit or block further nucleotide incorporations (e.g., a terminator blocking moiety). The blocking moiety can be attached to the 2' or 3' sugar position. The nucleotides can be attached at the base position to the optically-detectable label, and attached at the 2' or 3' sugar position to the blocking moiety. The linker that attaches the label to the base, and attaches the blocking moiety to the sugar, can be the same or different type of linker. After a nucleotide is incorporated, the identity of the incorporated nucleotide is determined by exposing the incorporated nucleotide with radiation energy (e.g., light) and the emitted signal from the label is detected. The optically-detectable label and/or the blocking moiety are removed from the incorporated nucleotide by reacting the linker with a cleaving agent. If the same type of linker is used to attach the label to the base and attach the blocking moiety to the sugar, then one type of cleaving agent can be used to remove the label and blocking moiety. If a different type of linker is used to attach the label to the base and attach the blocking moiety to the sugar, then two types of cleaving agent can be used to remove the label and blocking moiety. The next sequencing cycle begins by performing a subsequent nucleotide flow, and the washing, identifying, and linker cleaving steps are repeated. In some embodiments, the sequence-by-synthesis methods include those described by Illumina (U.S. Pat. Nos. 7,057,026; 7,566,537; 7,785,796; 8,158,346; 7,541,444; 7,057,026; 7,592,435; 7,414,116; 7,427,673 and 8,399,188) and described by Jingyu Ju (U.S. Pat. Nos. 7,713,698; 7,790,869; 8,088,575; 7,635,578; and 7,883,869) which are all expressly incorporated herein by reference as if set forth in full.

In some embodiments, provided are methods, as well as related compositions, kits, and systems, for reducing nucleic acid damage and/or for fragmenting nucleic acids and/or for preparing a control nucleic acid, which includes sequencing control nucleic acids, using a suitable electrical or optical detector. In some embodiments, any of the fragmented nucleic acids and/or the control nucleic acid that have been generated according to the present teachings is sequenced or detected by any sequencing method or detection means, including sequencing-by-synthesis, ion-based sequencing involving the detection of sequencing byproducts using field effect transistors (e.g., FETs and ISFETs), chemical degradation sequencing, ligation-based sequencing, hybridization sequencing, pyrosequencing or pyrophosphate detection sequencing, capillary electrophoresis, gel electrophoresis, next-generation, massively parallel sequencing platforms, sequencing platforms that detect hydrogen ions or other sequencing by-products, and sequencing platforms that can detect single molecule sequencing platforms. In some embodiments, a sequencing reaction is conducted using at least one sequencing primer that can hybridize to any portion of the amplicons, including a nucleic acid adaptor (e.g., universal sequence) or a target polynucleotide sequence.

In some embodiments, the sequencing reaction is conducted on a support having one or more reaction sites coupled to a sensor.

In some embodiments, any of the fragmented nucleic acids and/or the control nucleic acid produced according to the present teachings is sequenced using an array having CMOS. The sequencing may be conducted through non-optical (detecting reaction byproducts) or optical methods. The optical methods may include dye-labeled tags on the sequences or on any nucleotides hybridized to the sequence.

In some embodiments, any of the fragmented nucleic acids and/or the control nucleic acid produced according to the present teachings is sequenced using methods that detect one or more byproducts of nucleotide incorporation. The detection of polymerase extension by detecting physicochemical byproducts of the extension reaction, can include pyrophosphate, hydrogen ion, charge transfer, heat, and the like, as disclosed, for example, in U.S. Pat. No. 7,948,015 to Rothberg et al.; and Rothberg et al, U.S. Patent Publication No. 2009/0026082, hereby incorporated by reference in their entireties. Other examples of methods of detecting polymerase-based extension can be found, for example, in Pourmand et al, Proc. Natl. Acad. Sci., 103: 6466-6470 (2006); Purushothaman et al., IEEE ISCAS, IV-169-172; Anderson et al, Sensors and Actuators B Chem., 129: 79-86 (2008); Sakata et al., Angew. Chem. 118:2283-2286 (2006); Esfandyapour et al., U.S. Patent Publication No. 2008/01666727; and Sakurai et al., Anal. Chem. 64: 1996-1997 (1992). In addition detection may be based on a change in capacitance, impedance or conductivity or voltammetry.

Reactions involving the generation and detection of ions are widely performed. The use of direct ion detection methods to monitor the progress of such reactions can simplify many current biological assays. For example, template-dependent nucleic acid synthesis by a polymerase can be monitored by detecting hydrogen ions that are generated as natural byproducts of nucleotide incorporations catalyzed by the polymerase. Ion-sensitive sequencing (also referred to as "pH-based" or "ion-based" nucleic acid sequencing) exploits the direct detection of ionic byproducts, such as hydrogen ions, that are produced as a byproduct of nucleotide incorporation. In one exemplary system for ion-based sequencing, the nucleic acid to be sequenced is captured in a microwell, and nucleotides are flowed across the well, one at a time or two or more different types, under nucleotide incorporation conditions. The polymerase incorporates the appropriate nucleotide into the growing strand, and the hydrogen ion that is released can change the pH in the solution, which is detected by an ion sensor that is coupled with the well. This technique does not require labeling of the nucleotides or expensive optical components, and allows for far more rapid completion of sequencing runs. Examples of such ion-based nucleic acid sequencing methods and platforms include the Ion PGM™, Ion Proton™, and Ion S5sequencer (Ion Torrent™ Systems, Thermo Fisher Scientific).

In some embodiments, any of the fragmented nucleic acids and/or the control nucleic acid produced using the methods, systems, compositions or kits of the present teachings are used as a substrate for a biological or chemical reaction that is detected and/or monitored by a sensor including a field-effect transistor (FET). In various embodiments the FET is a chemFET, FinFET or an ISFET. A "chemFET" or chemical field-effect transistor, is a type of field effect transistor that acts as a chemical sensor. It is the structural analog of a MOSFET transistor, where the charge on the gate electrode is applied by a chemical process. An "ISFET" or ion-sensitive field-effect transistor, is used for measuring ion concentrations in solution; when the ion concentration (such as H+) changes, the current through the transistor will change accordingly. A detailed theory of operation of an ISFET is given in "Thirty years of ISFETOLOGY: what happened in the past 30 years and what may happen in the next 30 years," P. Bergveld, Sens. Actuators, 88 (2003), pp. 1-20. A Fin Field Effect Transistor or "FinFET" is a type of non-planar or three-dimensional transistor. Additionally, a nanowire may be used either alone or in conjunction with the FET.

In some embodiments, the FET may be a FET array. As used herein, an "array" is a planar arrangement of elements such as sensors or wells. The array may be one or two dimensional. A one dimensional array can be an array having one column (or row) of elements in the first dimension and a plurality of columns (or rows) in the second dimension. The number of columns (or rows) in the first and second dimensions may or may not be the same. The FET or array can comprise $10^2$, $10^3$, $10^4$, $10^5$, $10^6$, $10^7$ or more FETs.

In some embodiments, one or more microfluidic structures are fabricated above the FET sensor array to provide for containment and/or confinement of a biological or chemical reaction. For example, in one implementation, the microfluidic structure(s) are configured as one or more wells (or microwells, or reaction chambers, or reaction wells, as the terms are used interchangeably herein) disposed above one or more sensors of the array, such that the one or more sensors over which a given well is disposed detect and measure analyte presence, level, and/or concentration in the given well. In some embodiments, there is a 1:1 correspondence of FET sensors and reaction wells. Exemplary embodiments of FET sensor arrays can be found in U.S. Pat. Nos. 7,948,015; 8,262,900; 8,776,573; 8,208,712.

Microwells or reaction chambers are typically hollows or wells having well-defined shapes and volumes which can be manufactured into a substrate and can be fabricated using conventional microfabrication techniques, e.g. as disclosed in the following references: Doering and Nishi, Editors, Handbook of Semiconductor Manufacturing Technology, Second Edition (CRC Press, 2007); Saliterman, Fundamentals of BioMEMS and Medical Microdevices (SPIE Publications, 2006); Elwenspoek et al, Silicon Micromachining (Cambridge University Press, 2004); and the like. Examples of configurations (e.g. spacing, shape and volumes) of microwells or reaction chambers are disclosed in Rothberg et al, U.S. patent publication 2009/0127589; Rothberg et al, U.K. patent application GB24611127.

In some embodiments, the biological or chemical reaction is performed in a solution or a reaction chamber that is in contact with, operatively coupled, or capacitively coupled to a FET such as a chemFET, FinFET, or an ISFET. The FET (FinFET or chemFET or ISFET) and/or reaction chamber is an array of FETs or reaction chambers, respectively.

In some embodiments, a biological or chemical reaction is carried out in a two-dimensional or three-dimensional array of reaction chambers, wherein each reaction chamber is coupled to a FET, and each reaction chamber is no greater than 10 $\mu m^3$ (i.e., 1 pL) in volume. In some embodiments each reaction chamber is no greater than 0.34 pL, 0.096 pL or even 0.012 pL in volume. A reaction chamber can optionally be no greater than 2, 5, 10, 15, 22, 32, 42, 52, 62, 72, 82, 92, or 102 square microns in cross-sectional area at the top. Preferably, the array has at least $10^2$, $10^3$, $10^4$, $10^5$, $10^6$, $10^7$, $10^8$, $10^9$, or more reaction chambers. In some embodiments, at least one of the reaction chambers is operatively coupled to at least one of the FETs.

FET arrays as used in various embodiments according to the disclosure can be fabricated according to conventional CMOS fabrications techniques, as well as modified CMOS fabrication techniques and other semiconductor fabrication techniques beyond those conventionally employed in CMOS fabrication. Additionally, various lithography techniques can be employed as part of an array fabrication process.

Exemplary FET arrays suitable for use in the disclosed methods, as well as microwells and attendant fluidics, and methods for manufacturing them, are disclosed, for example, in U.S. Patent Publication No. 2010/0301398; U.S. Patent Publication No. 2010/0300895; U.S. Patent Publication No. 2010/0300559; U.S. Patent Publication No. 2010/0197507, U.S. Patent Publication No. 2010/0137143; U.S. Patent Publication No. 2009/0127589; and U.S. Patent Publication No. 2009/0026082, which are incorporated by reference in their entireties.

In one aspect, the disclosed methods, compositions, systems, apparatuses and kits are used for carrying out label-free nucleic acid sequencing, and in particular, ion-based nucleic acid sequencing. The concept of label-free detection of nucleotide incorporation has been described in the literature, including the following references that are incorporated by reference: Rothberg et al, U.S. patent publication 2009/0026082; Anderson et al, Sensors and Actuators B Chem., 129: 79-86 (2008); and Pourmand et al, Proc. Natl. Acad. Sci., 103: 6466-6470 (2006). Briefly, in nucleic acid sequencing applications, nucleotide incorporations are determined by measuring natural byproducts of polymerase-catalyzed extension reactions, including hydrogen ions, polyphosphates, PPi, and Pi (e.g., in the presence of pyrophosphatase). Examples of such ion-based nucleic acid sequencing methods and platforms include the Ion PGM™ or Ion Proton™, or Ion S5® sequencer (Ion Torrent™ Systems, Thermo Fisher Scientific).

In some embodiments, provided are methods for sequencing any of the fragmented nucleic acids and/or the control nucleic acid produced by the teachings provided herein. In one exemplary embodiment, provided is a method for obtaining sequence information from amplicons, comprising: (a) generating the fragmented nucleic acids and/or the control nucleic acid; and (b) sequencing the fragmented nucleic acids and/or the control nucleic acid by performing template-dependent nucleic acid synthesis using at least one of the target nucleic acids or amplicons produced during step (a) as a template. The amplifying can optionally be performed according to any of the amplification methods described herein.

In some embodiments, the template-dependent synthesis includes incorporating one or more nucleotides in a template-dependent fashion into a newly synthesized nucleic acid strand.

Optionally, the methods can further include producing one or more ionic byproducts of such nucleotide incorporation.

In some embodiments, the methods can further include detecting the incorporation of the one or more nucleotides into the sequencing primer. Optionally, the detecting can include detecting the release of hydrogen ions.

In another embodiment, provided are methods for sequencing a control nucleic acid, comprising: (a) attaching the control nucleic acids to sequencing particles by amplifying the target nucleic acids in the presence of sequencing particles to generate at least one particle attached with a substantially monoclonal polynucleotide population containing a portion of one of the target nucleic acids, according to the teachings disclosed herein; and (b) disposing the particles into a reaction chambers, wherein one or more of the reaction chambers are in contact with a field effect transistor (FET). Optionally, the method further includes contacting the substantially monoclonal polynucleotide population, which are disposed into one of the reaction chambers, with a polymerase thereby synthesizing a new nucleic acid strand by sequentially incorporating one or more nucleotides into a nucleic acid molecule. Optionally, the method further includes generating one or more hydrogen ions as a byproduct of such nucleotide incorporation. Optionally, the method further includes detecting the incorporation of the one or more nucleotides by detecting the generation of the one or more hydrogen ions using the FET.

In some embodiments, the detecting includes detecting a change in voltage and/or current at the at least one FET within the array in response to the generation of the one or more hydrogen ions.

In some embodiments, the FET is selected from the group consisting of: ion-sensitive FET (ISFET) and chemically-sensitive FET (chemFET).

In some embodiments, provided are methods (and related compositions, systems, kits and apparatuses) for nucleic acid sequencing, comprising identifying a series of contiguous nucleotides in a nucleic acid template according to any of the methods disclosed herein.

One exemplary system involving sequencing via detection of ionic byproducts of nucleotide incorporation is the Ion PGM™ or Ion Proton™ or Ion S5 ® sequencer (Ion Torrent System, Thermo Fisher Scientific), which is an ion-based sequencing system that sequences nucleic acid templates by detecting hydrogen ions produced as a byproduct of nucleotide incorporation. Typically, hydrogen ions are released as byproducts of nucleotide incorporations occurring during template-dependent nucleic acid synthesis by a polymerase. The Ion PGM™, Ion Proton™, or Ion 55® sequencer detects the nucleotide incorporations by detecting the hydrogen ion byproducts of the nucleotide incorporations. The Ion PGM™, Ion Proton™, or Ion 55® sequencer can include a plurality of nucleic acid templates to be sequenced, each template disposed within a respective sequencing reaction well in an array. The wells of the array can each be coupled to at least one ion sensor that can detect the release of $H^+$ ions or changes in solution pH produced as a byproduct of nucleotide incorporation. The ion sensor comprises a field effect transistor (FET) coupled to an ion-sensitive detection layer that can sense the presence of $H^+$ ions or changes in solution pH. The ion sensor can provide output signals indicative of nucleotide incorporation which can be represented as voltage changes whose magnitude correlates with the $H^+$ ion concentration in a respective well or reaction chamber. Different nucleotide types can be flowed serially into the reaction chamber, and can be incorporated by the polymerase into an extending primer (or polymerization site) in an order determined by the sequence of the template. Alternatively, one type of nucleotide can be flowed into the reaction chamber, and can be incorporated by the polymerase into an extending primer (or polymerization site) in an order determined by the sequence of the template. Each nucleotide incorporation can be accompanied by the release of $H^+$ ions in the reaction well, along with a concomitant change in the localized pH. The release of $H^+$ ions can be registered by the FET of the sensor, which produces signals indicating the occurrence of the nucleotide incorporation. Nucleotides that are not incorporated during a particular nucleotide flow may not produce signals. The amplitude of the signals from the FET can also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers can permit the instrument to resolve the sequence of many nucleic acid templates simultaneously. Further details regarding the compositions, design and operation of the Ion PGM™ or Ion Proton™ or Ion S5™ or Ion S5XL™ sequencers can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties.

In a typical embodiment of ion-based nucleic acid sequencing, nucleotide incorporations can be detected by detecting the presence and/or concentration of hydrogen ions generated by polymerase-catalyzed extension reactions. In one embodiment, templates, optionally pre-bound to a sequencing primer and/or a polymerase, can be loaded into reaction chambers (such as the microwells disclosed in Rothberg et al, cited herein), after which repeated cycles of nucleotide addition and washing can be carried out. In some embodiments, such templates can be attached as clonal populations to a solid support, such as particles, bead, or the like, and said clonal populations are loaded into reaction chambers.

In another embodiment, the fragmented nucleic acids and/or the control nucleic acid and/or adaptor-joined control nucleic acid is distributed, deposited or positioned to different sites of the array. In some embodiments, the fragmented nucleic acids and/or the control nucleic acid and/or adaptor-joined control nucleic acid is attached to a particle, and the particle is deposited to the array. In some embodiments, the sites of the array include primers and the methods can include hybridizing the deposited nucleic acids to the primers within different sites.

In each addition step of the cycle, the polymerase can extend the primer by incorporating added nucleotide only if the next base in the template is the complement of the added nucleotide. If there is one complementary base, there is one incorporation, if two, there are two incorporations, if three, there are three incorporations, and so on. With each such incorporation there is a hydrogen ion released, and collectively a population of templates releasing hydrogen ions changes the local pH of the reaction chamber. The production of hydrogen ions is monotonically related to the number of contiguous complementary bases in the template (as well as the total number of template molecules with primer and polymerase that participate in an extension reaction). Thus, when there are a number of contiguous identical complementary bases in the template (i.e. a homopolymer region), the number of hydrogen ions generated, and therefore the magnitude of the local pH change, can be proportional to the number of contiguous identical complementary bases. If the next base in the template is not complementary to the added nucleotide, then no incorporation occurs and no hydrogen ion is released. In some embodiments, after each step of adding a nucleotide, an additional step can be performed, in which an unbuffered wash solution at a predetermined pH is used to remove the nucleotide of the previous step in order to prevent misincorporations in later cycles. In some embodiments, the after each step of adding a nucleotide, an additional step can be performed wherein the reaction chambers are treated with a nucleotide-destroying agent, such as apyrase, to eliminate any residual nucleotides remaining in the chamber, which may result in spurious extensions in subsequent cycles.

In one exemplary embodiment, different kinds of nucleotides are added sequentially to the reaction chambers, so that each reaction is exposed to the different nucleotides one at a time. For example, nucleotides can be added in the following sequence: dATP, dCTP, dGTP, dTTP, dATP, dCTP, dGTP, dTTP, and so on; with each exposure followed by a wash step. The cycles may be repeated for 50 times, 100 times, 200 times, 300 times, 400 times, 500 times, 750 times, or more, depending on the length of sequence information desired.

In some embodiments, sequencing is performed according to the user protocols supplied with the Ion PGM™, Ion Proton™, or Ion S5® sequencer. Example 2 provides one exemplary protocol for ion-based sequencing using the Ion PGM™ sequencer (Ion Torrent™ Systems, Thermo Fisher Scientific).

In some embodiments, a CMOS sensor can detect a nucleotide incorporation event, including detect nucleotide incorporation byproducts. In some embodiments, in addition to using CMOS technology to detect reaction byproducts, such as hydrogen ions, phosphate ions, pyrophosphate ions or phosphate chains, CMOS technology may be used as sensor to detect other measurable signals. For example, CMOS technology may be used to detect fluorescence, phosphorescence, luminescence, bio-luminescence. In some embodiments, the surface of the sensors may have receptors or may be treated with a surface treatment so that the sensor surface may attract and/or bind to any molecules being detected. The surface treatment may be used to improve the signal to noise ratio (SNR) of the system. In some embodiments, the sensors may be combined with nanowires.

In some embodiments, provided are methods for sequencing a population of template polynucleotides, comprising: (a) generating a plurality of amplicons by clonally amplifying a plurality of target polynucleotides onto a plurality of particles, wherein the amplifying is performed within a single continuous phase of a reaction mixture and wherein at least 10%, 20%, 30%, 40%, 50%, 60%, 70%, 80%, 90%, or 95% of the resulting amplicons are substantially monoclonal in nature. In some embodiments, a sufficient number of substantially monoclonal amplicons are produced in a single amplification reaction to generate at least 100 MB, 200 MB, 300 MB, 400 MB, 500 MB, 750 MB, 1 GB or 2 GB of AQ20 sequencing reads on an Ion Torrent PGM™ 314, 316 or 318 sequencer. The term "AQ20 and its variants, as used herein, refers to a particular method of measuring sequencing accuracy in the Ion Torrent PGM™ sequencer. Accuracy can be measured in terms of the Phred-like Q score, which measures accuracy on logarithmic scale that: Q10=90%, Q20=99%, Q30=99.9%, Q40=99.99%, and Q50=99.999%. For example, in a particular sequencing reaction, accuracy metrics can be calculated either through prediction algorithms or through actual alignment to a known reference genome. Predicted quality scores ("Q scores") can be derived from algorithms that look at the inherent properties of the input signal and make fairly accurate estimates regarding if a given single base included in the sequencing "read" will align. In some embodiments, such predicted quality scores can be useful to filter and remove lower quality reads prior to downstream alignment. In some embodiments, the accuracy can be reported in terms of a Phred-like Q score that measures accuracy on logarithmic scale such that: Q10=90%, Q17=98%, Q20=99%, Q30=99.9%, Q40=99.99%, and Q50=99.999%. In some embodiments, the data obtained from a given polymerase reaction can be filtered to measure only polymerase reads measuring "N" nucleotides or longer and having a Q score that passes a certain threshold, e.g., Q10, Q17, Q100 (referred to herein as the "NQ17" score). For example, the 100Q20 score can indicate the number of reads obtained from a given reaction that are at least 100 nucleotides in length and have Q scores of Q20 (99%) or greater. Similarly, the 200Q20 score can indicate the number of reads that are at least 200 nucleotides in length and have Q scores of Q20 (99%) or greater.

In some embodiments, the accuracy can also be calculated based on proper alignment using a reference genomic sequence, referred to herein as the "raw" accuracy. This is single pass accuracy, involving measurement of the "true" per base error associated with a single read, as opposed to consensus accuracy, which measures the error rate from the consensus sequence which is the result of multiple reads. Raw accuracy measurements can be reported in terms of "AQ" scores (for aligned quality). In some embodiments, the data obtained from a given polymerase reaction can be filtered to measure only polymerase reads measuring "N" nucleotides or longer having a AQ score that passes a certain threshold, e.g., AQ10, AQ17, AQ100 (referred to herein as the "NAQ17" score). For example, the 100AQ20 score can indicate the number of reads obtained from a given polymerase reaction that are at least 100 nucleotides in length and have AQ scores of AQ20 (99%) or greater. Similarly, the 200AQ20 score can indicate the number of reads that are at least 200 nucleotides in length and have AQ scores of AQ20 (99%) or greater.

In some embodiments, provided are methods, as well as related compositions, kits, and systems, used to prepare fragmented nucleic acids or control nucleic acids are subjected to any one or any combination of nucleic acid manipulation steps including: end-repairing, internal-repairing, end-tailing, size-selecting, adaptor-joining, nick-translating, amplifying, measuring, quantifying, diluting and/or sequencing.

In some embodiments, any of the steps in a nucleic acid library preparation workflow are performed manually or by automation, including the steps of: fragmenting, end-repairing, internal-repairing, end-tailing, size-selection, adaptor-joining, nick-translation, amplification, quantification and/or sequencing. In some embodiments, all of the steps are performed manually or by automation. In some embodiments, any one or any combination of the steps are conducted by any combination of manual or automation modes.

EXAMPLES

Embodiments of the present teachings can be further understood in light of the following examples, which should not be construed as limiting the scope of the present teachings in any way.

Example 1: Preparation of Control DNAs

A Covaris water bath was filled to level 12 and degassed for 30 minutes prior to shearing. A microTUBE was placed in the holder, with water level at the base of the cap and the glass portion of the microTUBE completely submerged. The chiller was set to 4° C.

Prepared DNA containing numerous oncology hotspot mutations is similar to the commercially-available AcroMetrix™ Oncology Hotspot Control DNA (Thermo Fisher Scientific, Inc., catalog No. 969056), however the provided oncology hotspot control DNA contains approximately 50% allelic frequencies. Normal background DNA was GM24385 (e.g, from Coriell Institute for Medical Research, catalog No. NA24385). Two input DNAs were sheared separately, then specified amounts of the sheared oncology hotspot DNA was spiked into the prepared sheared normal background DNA to achieve various concentrations of oncology sequences (e.g., 0.01%, 0.5% and 1%).

The Hotspot Control DNA and normal background DNA was sheared Low TE was added to DNA to bring total volume to 127.4 µl. Add 1.3 µl of 100 mM EDTA. Add 1.3 µl of 100 mM 3-indole propionic acid dissolved in methanol for an effective concentration of 1 mM. In some cases, DNA was sheared with only 3-indole propionic acid, or only EDTA, or only with TE and no 3-indole propionic acid and no EDTA. Keeping the cap on the tube, transfer the entire volume into the 130 µl Covaris microTUBE by inserting the pipette tip through the pre-split septa. Be careful not to introduce any bubbles, especially in the bottom of the tube. Load the sample tube into the Covaris Sample holder.

One mL working stock of 100 mM 3-indole propionic acid was prepared by dissolving 18.9 mg 3-indole propionic acid (MP Biomedicals 10204810) in 1 mL 100% methanol (Fisher Scientific A452-1).

The process configuration for the Covaris S2 system was set up based on the following table:

TABLE 1

| |
|---|
| For genomic DNA (GM24385): Number of Cycles: 6 |
| For plasmid DNA (hotspot oncology): Number of Cycles: 1 |
| Bath Temperature 5° C. |
| Bath Temperature Limit: 30° C. |
| Mode: Frequency sweeping |
| Water Quality Testing Function: Off |
| Duty Cycle: 10% |
| Intensity: 5 |
| Cycles/burst: 100 |
| Time: 60 s |

The process was initiated by clicking "START" to run.

After shearing process was completed, the entire volume of 130 µl of sheared DNA was transferred to 1.5 ml nuclease-free low adhesion tubes by inserting the pipette tip through the pre-split septa and slowly removing the fluid. The snap-cap was removed to ensure all the volume was recovered.

Concentrating the DNA: 260 µl of Agencourt AMPure beads (2 volumes) was added to the sample and incubated for 10 minutes at room temperature on a rotator.

The sample tube was placed in a magnetic rack until the solution became clear.

The supernatant was removed and discarded.

500 µL of freshly prepared 80% ethanol was added. The bead pellet was washed by lifting the tube, turning it 180° and then placing it back in the rack. This washing step was performed a total of 6 times to wash thoroughly. Turning the tube allows the magnet to declump the beads and prevents the need for vigorous vortexing. Using freshly prepared 80% ethanol is critical as a higher percentage will result in an inefficient washing of smaller-sized molecules and using lower than 80% ethanol could cause loss of sample.

The tube of sample was placed in the magnetic rack and the supernatant was removed. The tube was pulse-spun to remove the residual ethanol.

The beads were air-dried completely at room temperature approximately 5 minutes (the beads did not look shiny anymore and had a matte finish).

25 µL low TE was added to the sample and vortexed for 10 seconds. The solution was pipetted up and down several times to ensure homogeneity.

The tube of sample was placed in the magnetic rack. After the solution cleared, the eluted sample (supernatant) was transferred into a new 1.5-mL LoBind tube.

Fragment nucleic acids can be stored in low TE at −20° C.

Prepared oncology DNA was diluted into the prepared GM24385 DNA to achieve various dilutions, wherein concentrations of the oncology hotspot sequences was 0.05%, 0.1% or 1%, and the diluted DNA was used as a control DNA for Example 2 below.

Example 2: Tagging with Unique Randomer Tags

Molecular Tagging Procedures:

Molecular tagged libraries were generated from the prepared diluted control DNA (prepared as described in Example 1) using the Oncomine® Lung cfDNA Assay kit (catalog No. A31149 from Thermo Fisher Scientific) according to manufacturer's instructions. The Lung library panel contains uniquely tagged primers that target ALK, BRAF, EGFR, ERBB2, KRAS, MAP2K1, MET, NRAS, PIK3CA, ROS1 and TP53, and more than 150 mutation hotspots including EFGR (T790M, C797S, L858R and exon 19-del), KRAS (G12X, G13X and Q61X), BRAF (V600E), ALK (exon2l-25) and PIK3CA (E545K, H104R and E542K).

Molecular tagged libraries were also generated from the prepared diluted control DNA (prepared as described in Example 1) using the Oncomine® Colon cfDNA Assay kit (catalog No. A31182 from Thermo Fisher Scientific) according to manufacturer's instructions. The Colon library panel contains uniquely tagged primers that target AKT1, APC, BRAF, CTNNB1, EGFR, ERBB2, FBXW7, GNAS, KRAS, MAP1K1, NRAS, PIK3CA, SMAD4 and TP53, and more than 240 mutation hotspots including KRAS/NRAS (G12/G13/Q61), BRAF (V600E), PIK3CA (E545K and H104R), TP53 (R175H and R273H/C/L), recurring deleterious APC mutations (p.R876*, p.R1114*, p.Q1378* and p.R1450*), SMAD4 (R361C/H) and CTNNB1 (S45F and T41A).

Molecular tagged libraries were also generated from the prepared diluted control DNA (prepared as described in Example 1) using the Oncomine® Breast cfDNA Assay kit (catalog No. A31183 from Thermo Fisher Scientific) which contains uniquely tagged primers that target AKT1, EGFR, ERBB2, ERBB3, ESR1, FBXW7, KRAS, PIK3CA, SF3B1 and TP53, and more than 150 mutation hotspots including PIK3CA (E545K and H104R), AKT1 (E17K), ESR1 (mutations associated with anti-estrogen resistance), TP53 (mutations associates with loss of function) and ERBB2 (mutations associated with sensitivity to anti-ERBB2 therapies).

Resulting prepared libraries using control DNA were each prepared for sequencing on an Ion Torrent semiconductor sequencing chip according to manufacturer's instructions (kit catalog Nos. A25592, A30798, A26772 and A26433, all from Thermo Fisher Scientific).

Control DNA prepared by shearing DNA in the presence of a nucleic acid damage-mitigating reagent (e.g., 3-indole-propionic acid) and a chelating reagent (e.g., EDTA) significantly reduced the number of mutation artifacts from base transitions and base transversions number, which correlated with a reduced the number of false positive sequencing. By contrast, control DNA prepared by shearing DNA with no 3-indole-propionic acid and no EDTA, or with 3-indole-propionic acid alone, or with EDTA alone, exhibited an elevated level of base transitions and transversions, which correlated with an elevated level of false positive sequencing reads.

Figure 1B:
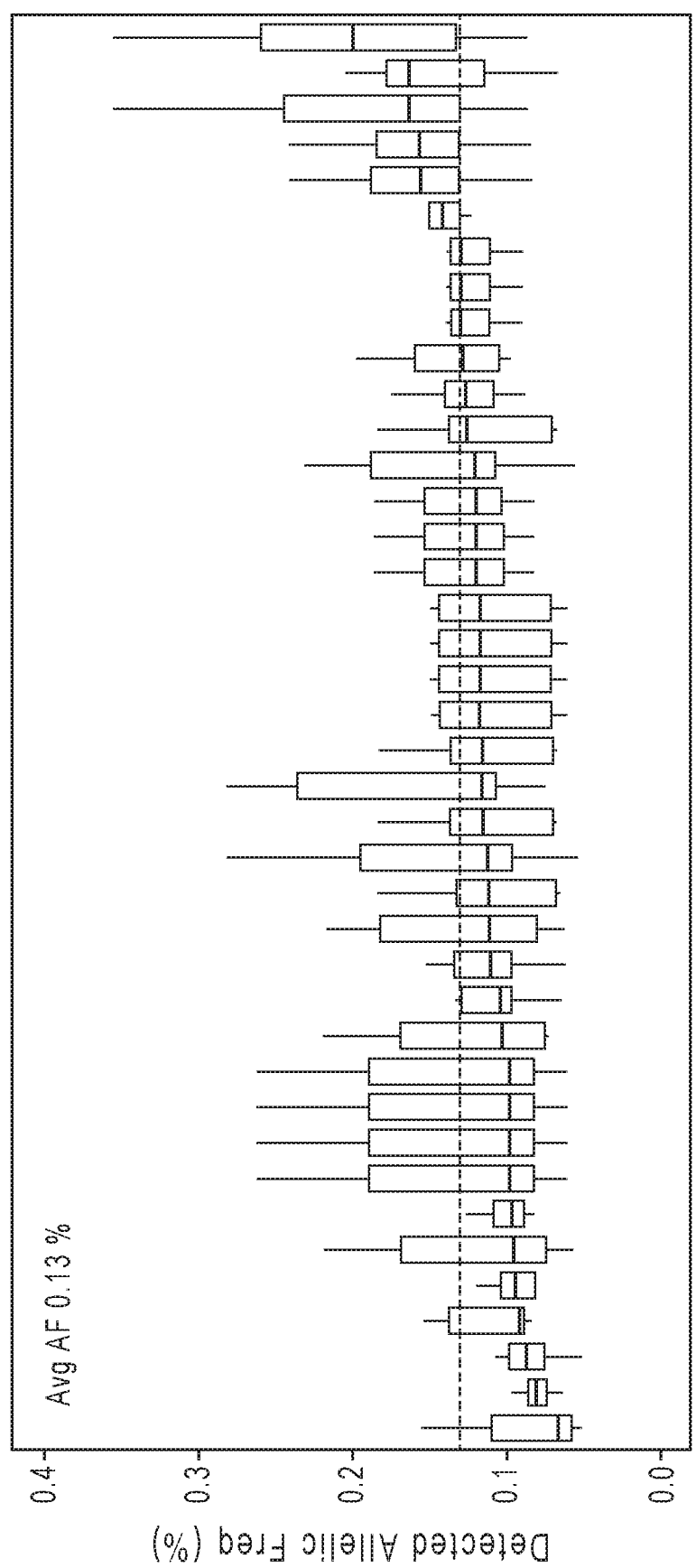
Figure 1C:
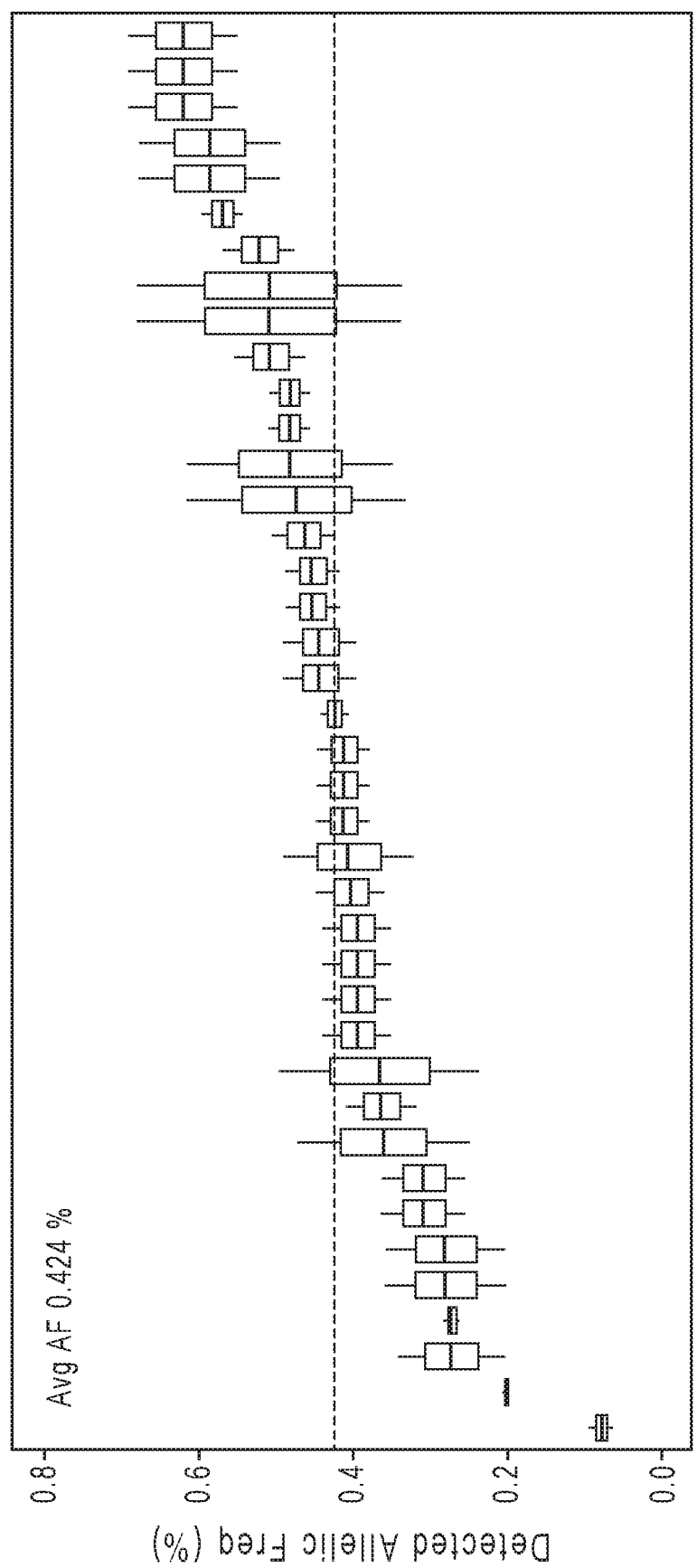
Figure 2A:
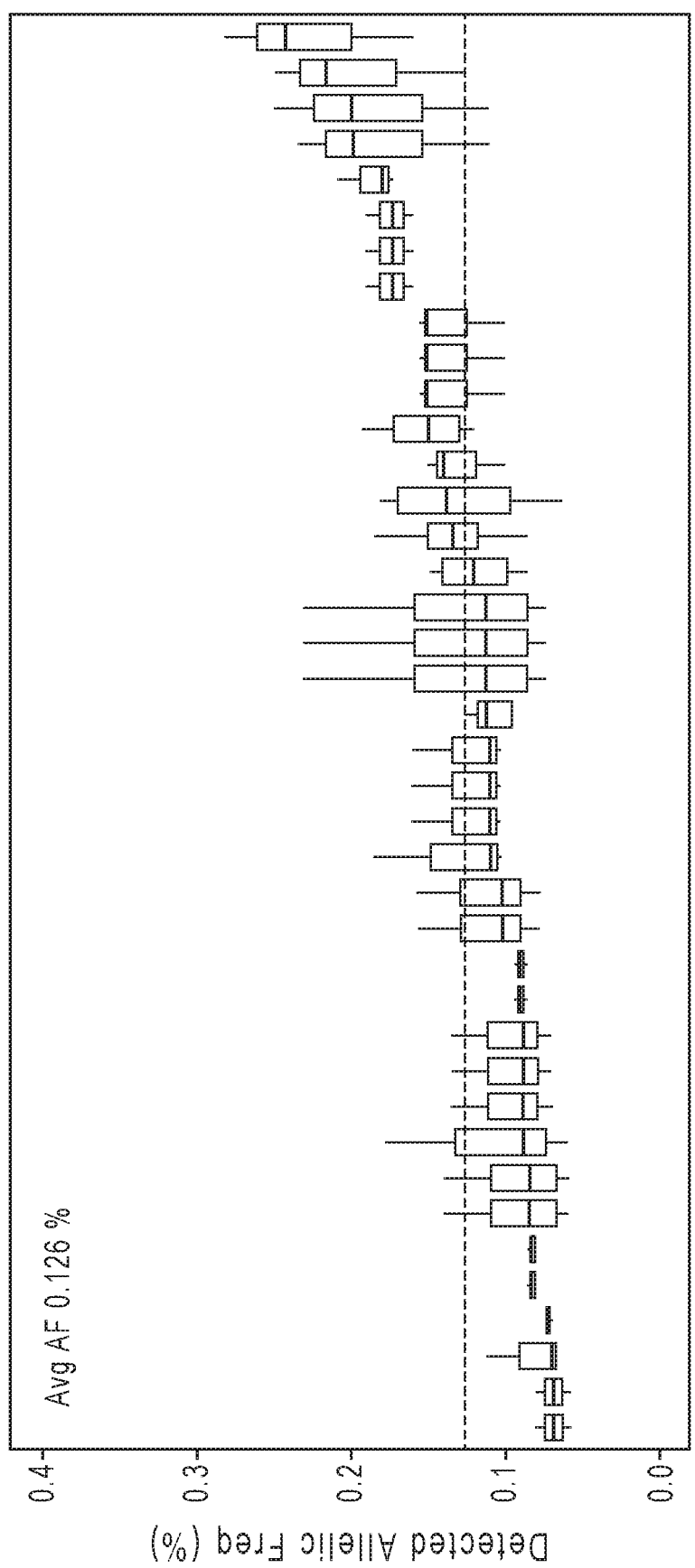
Figure 2B:
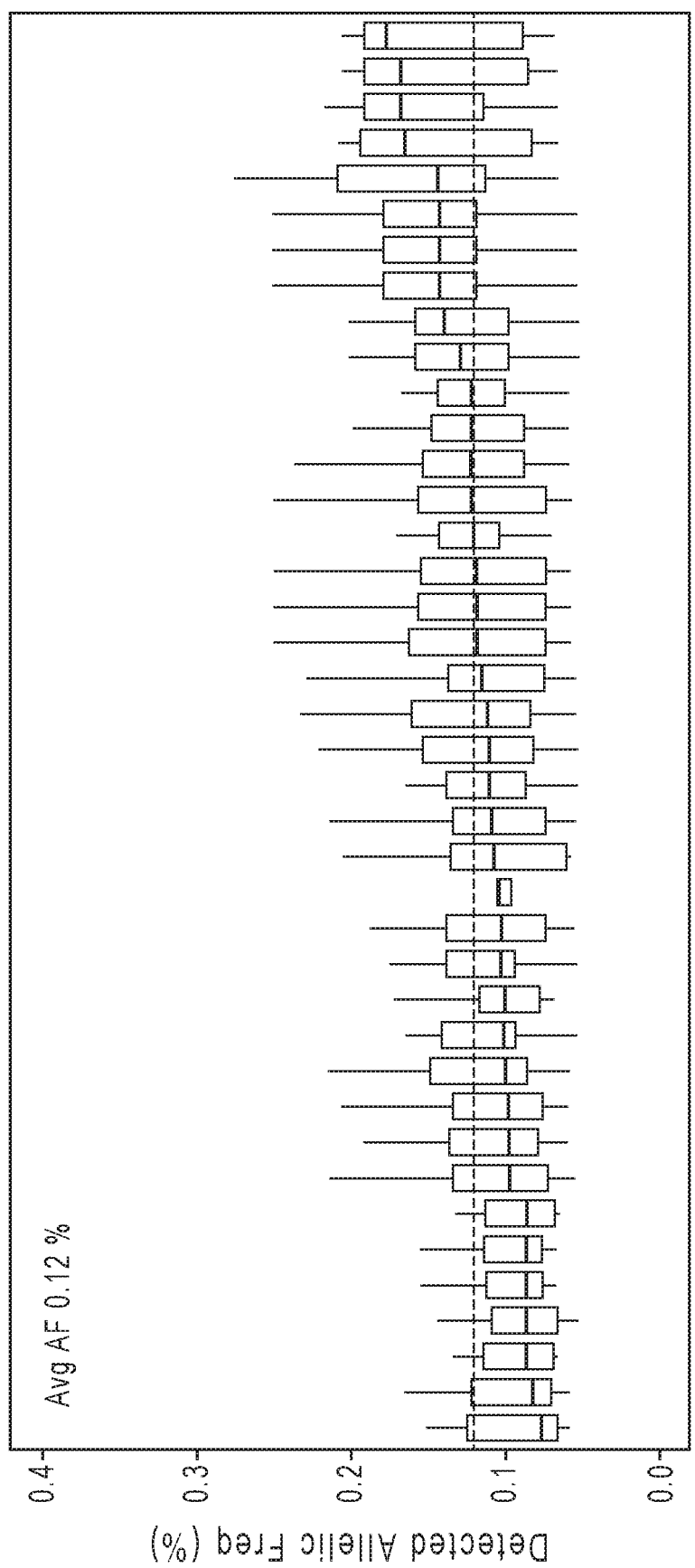
Figure 2C:
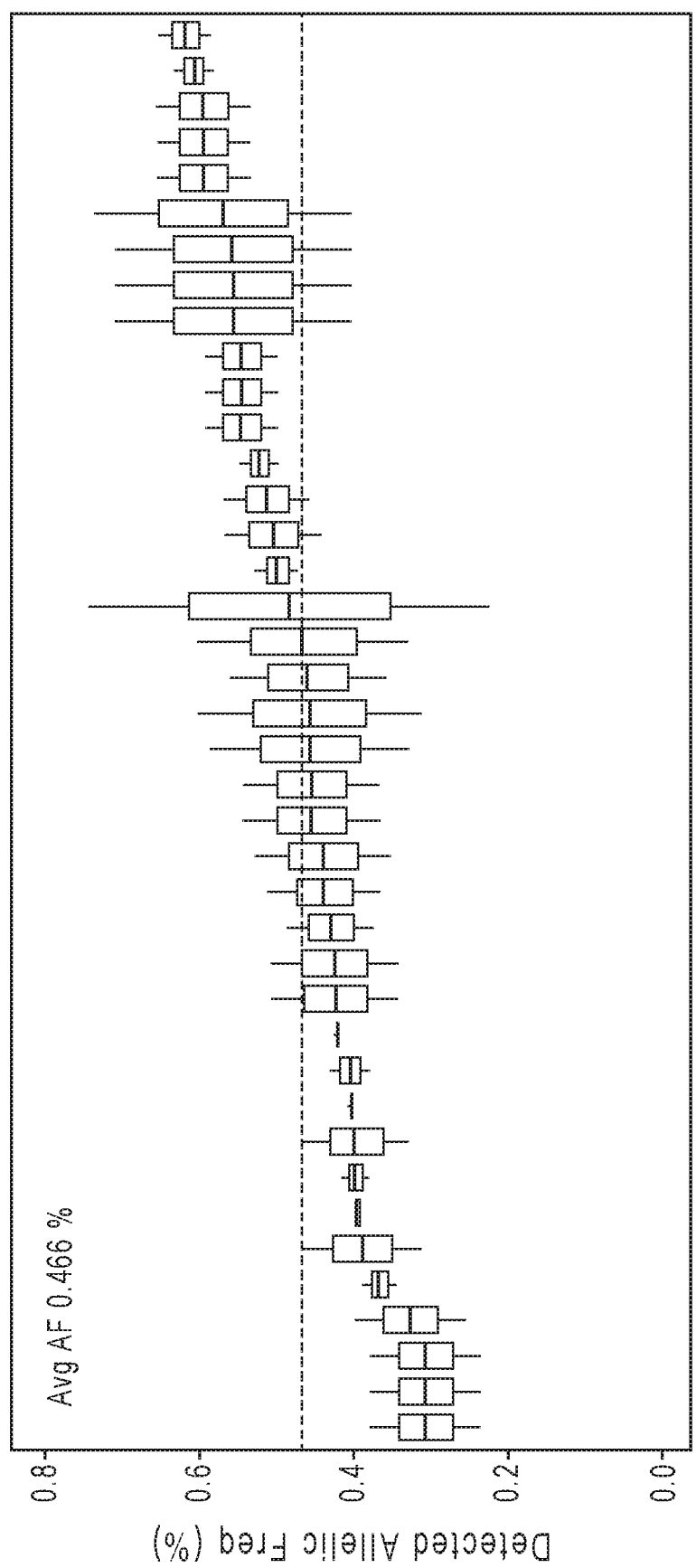
FIG. 2C depicts results of standards detected in a control sample prepared, tagged and sequenced as described in Examples 1 and 2.
Figure 2D:
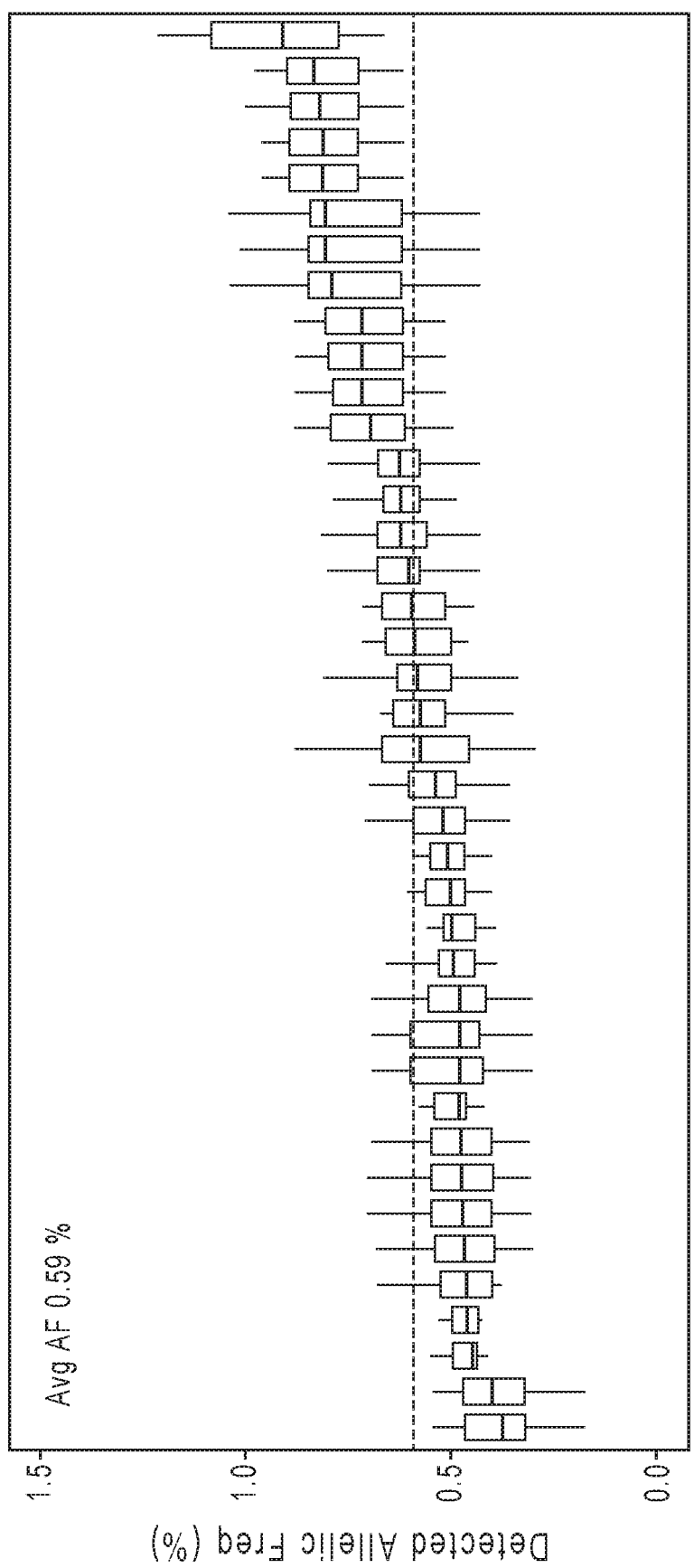

Sequencing results from molecularly tagged libraries using control DNA prepared by shearing with both 3-indole-propionic acid and EDTA are shown in FIGS. 1A-C(Colon panel), and FIGS. 2A-D (Lung panel). FIGS. 1A, B and C are quantile box plots showing detected allelic frequencies of 40 target sequences contained in control DNA prepared by methods described in the teachings herein, where the average allelic frequency is 0.11% (FIG. 1A), 0.13% (FIG. 1B), and 0.424% (FIG. 1C). FIGS. 2A, B, C and D are quantile box plots showing detected allelic frequencies of control DNA prepared by methods described in the teachings herein, where the average allelic frequency is 0.126% (FIG. 2A), 0.12% (FIG. 2B), 0.466% (FIG. 2C) and 0.59% (FIG. 2D). The 40 target sequences are listed in Tables 2 and 3 below. The target sequences listed top to bottom in each column in Tables 2 and 3 correspond to the target sequences in the graphs listed left to right of their respective Figures.

TABLE 2

| FIG. 1A | FIG. 1B | FIG. 1C |
| --- | --- | --- |
| chr3.41266101; C.G | chr17.7578388; C.T | chr5.112175211; T.TA |
| chr3.41266137; C.T | chr1.115258747; C.T | chr5.112175951; G.GA |
| chr3.41266113; C.T | chr17.37880981; A.AGCATACGTGATG SEQ ID NO: 3 | chr17.7578190; T.C |
| chr3.41266124; A.G | ch5.112175211; T.TA | chr20.57484596; A.T |
| chr.1.115256529; T.C | chr4.153247351; C.A | chr17.7578203; C.T |
| chr1.115256537; T.C | chr12.25398284; C.T | chr17.7578196; A.T |
| chr4.153247351; C.A | chr4.153247366; C.T | chr4.153247366; C.T |
| chr17.7578196; A.T | chr3.178936074; C.G | chr4.153247351; C.A |
| chr17.7578203; C.T | chr3.178936091; G.A | chr17.7578388; C.T |
| chr17.7578190; T.C | chr3.178936098; A.G | chr5.112174989; CA.C |
| chr12.25398284; C.T | chr3.178936082; G.A | chr17G7880981; A.AGCATACGTGATG SEQ ID NO: 3 |
| chr12.25398295; T.C | chr12.25398295; T.C | chr17.7577538; C.T |
| chr4.153249384; C.T | chr20.57484420; C.T | chr17.7577548; C.T |
| chr17.7578388; C.T | chr4.153249384; C.T | chr17.7577559; G.A |
| chr5.112175211; T.TA | chr5.112175951; G.GA | chr17.7577580; T.C |
| chr17.37880981; A.AGCATACGTGATG SEQ ID NO: 3 | chr17.7577548; C.T | chr3.41266137; C.T |
| chr20.57484420; C.T | chr1.115256537; T.C | chr4.153249384; C.T |
| chr5.112175951; G.GA | chr17.7577559; G.A | chr3.41266101; C.G |
| chr12.25380283; C.T | chr1.115256529; T.C | chr3.41266124; A.G |
| chr12.25380275; T.G | chr17.7577580; T.C | chr3.41266113; C.T |
| chr4.153247366; C.T | chr3.41266101; C.G | chr17.37881332; G.A |
| chr3.178936074; C.G | chr3.41266113; C.T | chr3.178936098; A.G |
| chr3.178936098; A.G | chr3.41266137; C.T | chr3.178936082; G.A |
| chr3.178936091; G.A | chr3.41266124; A.G | chr3.178936074; C.G |
| chr3.178936082; G.A | chr17.7578203; C.T | chr3.178936091; G.A |
| ch17.37881332.G.A | chr17.7578196; A.T | chr20.57484420; C.T |
| chr20.57484596; A.T | chr17.7578190; T.C | chr12.25380275; T.G |
| chr17.7577538; C.T | chr5.112174989; CA.C | chr12.25380283; C.T |
| chr14.105246551; C.T | chr17.7577538; C.T | chr12.25398295; T.C |
| chr5.112175675; AAG.A | chr20.57484596; A.T | chr12.25398284; C.T |
| chr1.115258747; C.T | chr14.105246551; C.T | chr5.112175675; AAG.A |
| ch5.112174989; CA.C | chr7.140453136; A.T | chr17.7577120; C.T |
| chr17.7577120; C.T | chr7.140453145; A.C | chr17.7577105; G.A |
| chr17.7577105; G.A | chr7.140453154; T.C | chr14.105246551; C.T |
| chr17.7577548; C.T | chr5.112175675; AAG.A | chr1.115258747; C.T |
| chr17.7577559; G.A | chr12.25380283; C.T | chr1.115256537; T.C |
| chr17.7577580; T.C | chr12.25380275; T.G | chr1.115256529; T.C |
| chr7.140453136; A.T | chr17.7577105; G.A | chr7.140453136; A.T |
| chr7.140453145; A.C | chr17.37881332; G.A | chr7.140453145; A.C |
| chr7.140453154; T.C | chr17.7577120; C.T | chr7.140453154; T.C |

TABLE 3

| FIG. 2A | FIG. 2B | FIG. 2C | FIG. 2D |
| --- | --- | --- | --- |
| chr17.7579295; C.T | chr17.7577105; G.A | chr17.7577580; T.C | chr17.7579295; C.T |
| chr17.7579312; C.T | chr17.7577120; C.T | chr17.7577548; C.T | chr17.7579312; C.T |
| chr17.7578235; T.C | chr3.178936082; G.A | chr17.7577559; G.A | chr17.7577105; G.A |
| chr7.116417465; T.C | chr17.37880981; A.AGCATACGTGATG SEQ ID NO: 3 | chr17.7577538; C.T | chr17.7577120; C.T |
| chr17.7577120; C.T | chr3.178936074; C.G | chr17G7880981; A.AGCATACGTGATG SEQ ID NO: 3 | chr17G7880981; A.AGCATACGTGATG SEQ ID NO: 3 |
| chr17.7577105; G.A | chr3.178936091; G.A | chr17.7577120; C.T | chr3.178936082; G.A |
| chr12.25398284; C.T | chr3.178936098; A.G | chr17.7579295; C.T | chr1.115258730; C.T |
| chr12.25398295; T.C | chr17.7577559; G.A | chr12.25398295; T.C | chr1.115258753; C.T |
| chr7.116423428; T.G | chr17.7579295; C.T | chr17.7577105; G.A | chr1.115258747; C.T |
| chr17.7578190; T.C | chr17.7579312; C.T | chr17.7579312; C.T | chr7.55249077; T.C |
| chr17.7578196; A.T | chr7.116417465; T.C | chr12.25398284; C.T | chr3.178936074; C.G |
| chr17.7578203; C.T | chr1.115258753; C.T | chr7.55248995; G.A | chr3.178936091; G.A |
| chr12.25380283; C.T | chr12.25398295; T.C | chr12.25380283; C.T | chr3.178936098; A.G |
| chr12.25380275; T.G | chr1.115258747; C.T | chr12.25380275; T.G | chr12.25380283; C.T |
| chr1.115256529; T.C | chr7.116423428; T.G | chr7.116423428; T.G | chr12.25380275; T.G |
| chr1.115256537; T.C | chr12.25398284; C.T | chr3.178936098; A.G | chr12.25398295; T.C |
| chr17.7578388; C.T | chr7.55248995; G.A | chr3.178936082; G.A | chr12.25398284; C.T |
| chr17.7578442; T.C | chr17.7577580; T.C | chr3.178936074; C.G | chr7.55248995; G.A |
| chr17.7578461; C.A | chr1.115258730; C.T | chr3.178936091; G.A | chr7.116423428; T.G |

TABLE 3-continued

| FIG. 2A | FIG. 2B | FIG. 2C | FIG. 2D |
|---|---|---|---|
| chr17.7578449; C.T | chr2.29432664; C.T | chr1.115258730; C.T | chr2.29432664; C.T |
| chr7.55249077; T.C | chr17.7577548; C.T | chr1.115258753; C.T | chr7.116417465; T.C |
| chr7.140453136; A.T | chr17.7577538; C.T | chr7.55249077; T.C | chr2.29443695; G.T |
| chr7.140453154; T.C | chr17.7578203; C.T | chr1.115258747; C.T | chr1.115256537; T.C |
| chr7.140453145; A.C | chr17.7578196; A.T | chr2.29443695; G.T | chr1.115256529; T.C |
| chr2.29432664; C.T | chr17.7578235; T.C | chr7.116417465; T.C | chr17.7577559; G.A |
| chr17.37880981; A.AGCATACGTGATG SEQ ID NO: 3 | chr2.29443695; G.T | chr1.115256529; T.C | chr17.7577548; C.T |
| chr2.29443695; G.T | chr17.7578190; T.C | chr1.115256537; T.C | chr17.7577538; C.T |
| chr3.178936082; G.A | chr12.25380283; C.T | chr17.7578235; T.C | chr17.7577580; T.C |
| chr7.55248995; G.A | chr12.25380275; T.G | chr17.7578190; T.C | chr17.7578235; T.C |
| chr3.178936074; C.G | chr7.55249077; T.C | chr17.7578196; A.T | chr17.7578203; C.T |
| chr3.178936091; G.A | chr1.115256537; T.C | chr17.7578203; C.T | chr17.7578196; A.T |
| chr3.178936098; A.G | chr1.115256529; T.C | chr17.7578442; T.C | chr17.7578190; T.C |
| chr17.7577548; C.T | chr7.140453136; A.T | chr17.7578461; C.A | chr7.140453154; T.C |
| chr17.7577580; T.C | chr7.140453154; T.C | chr17.7578449; C.T | chr7.140453136; A.T |
| chr17.7577559; G.A | chr7.140453145; A.C | chr17.7578388; C.T | chr7.140453145; A.C |
| chr17.7577538; C.T | chr7.116412044; G.A | chr7.140453136; A.T | chr17.7578442; T.C |
| chr1.115258730; C.T | chr17.7578388; C.T | chr7.140453145; A.C | chr17.7578449; C.T |
| chr1.115258753; C.T | chr17.7578461; C.A | chr7.140453154; T.C | chr17.7578388; C.T |
| chr1.115258747; C.T | chr17.7578442; T.C | chr7.116412044; G.A | chr17.7578461; C.A |
| chr7.116412044; G.A | chr17.7578449; C.T | chr2.29432664; C.T | chr7.116412044; G.A |

Example 3: Reducing Base Transitions and Transversions in Fragmented DNA

Control DNA was prepared as described in Example 1, except that 20 or 50 ng of input DNA as AcroMetrix™ Oncology Hotspot Control DNA (e.g., containing 50% allelic frequencies) or GM24385 DNA (Coriell Institute for Medical Research, catalog No. NA24385) was sheared with or without added reagents, including: standard shearing procedure performed with TE and without 3-indole-propionic acid (FM and SOP shear); or shearing with 3-indole propionic acid (3IPA shear and 3IPA shear 50 ng). To determine if shear-induced damage could be repaired, input DNA was sheared with 3-indole propionic acid and then treated with PreCR® Repair Mix (from New England Biolabs, catalog No. M0309S) according to manufacturer's instructions (3IPA shear PreCR). Non-sheared gDNA was included for comparison (gDNA). Control DNA was used to generate molecular tagged libraries using Oncomine® Lung cfDNA Assay kit (catalog No. A31149 from Thermo Fisher Scientific) according to the manufacturer's instructions. The molecular tagged libraries were prepared for sequencing on an Ion Torrent semiconductor sequencing chip according to manufacturer's instructions (kit catalog Nos. A25592, A30798, A26772 and A26433, all from Thermo Fisher Scientific).

Figure 3A:
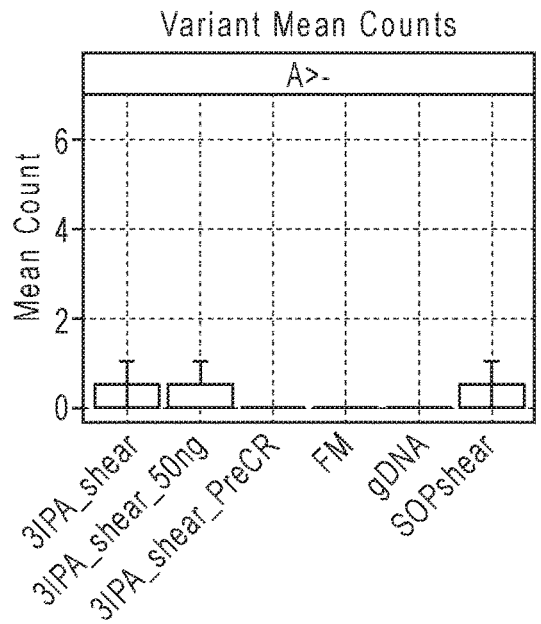
FIGS. 3A-G depict results of control DNA that was fragmented with 3-indole-propionic acid (3IPA shear), 3-indole-propionic acid (3IPA shear 50 ng), 3-indole-propionic acid and PreCR treatment (3IPA shear PreCR), FM, gDNA, or SOP fragmentation without 3-indole-propionic acid. The PreCR® Repair Mix was obtained from New England Biolabs (catalog No. M0309S). Prepared control DNA was subjected library preparation workflow using the Oncomine® Lung cfDNA Assay kit (Oncomine® lung cfDNA Assay kit, catalog No. A31149 from Thermo Fisher Scientific), and sequenced on an Ion Torrent sequencing platform, as described in Example 3. The y-axis depicts the mean count of variant sequences, which correlates with artifact base transitions or transversions, C>A, C>T, G>A, G>T, T>C, or T>G.
Figure 3B:
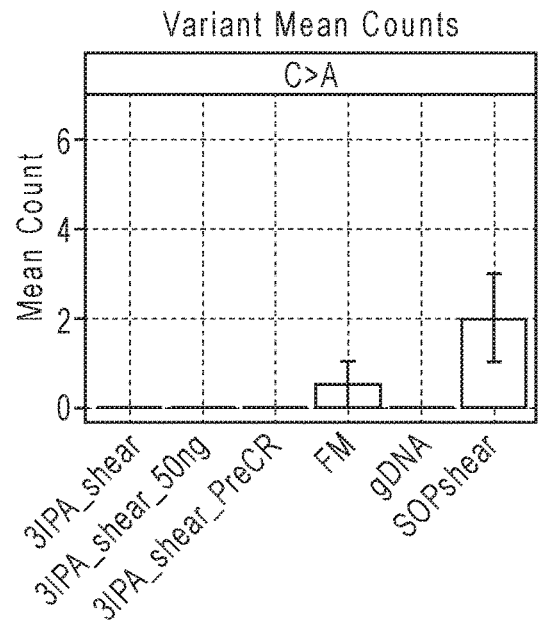
Figure 3C:
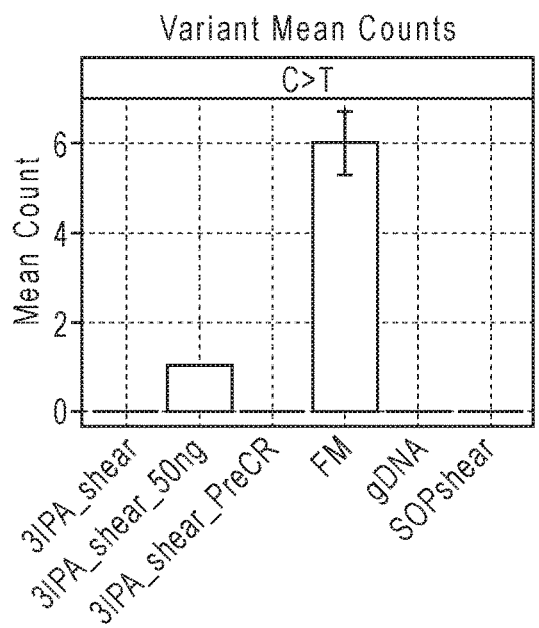
Figure 3D:
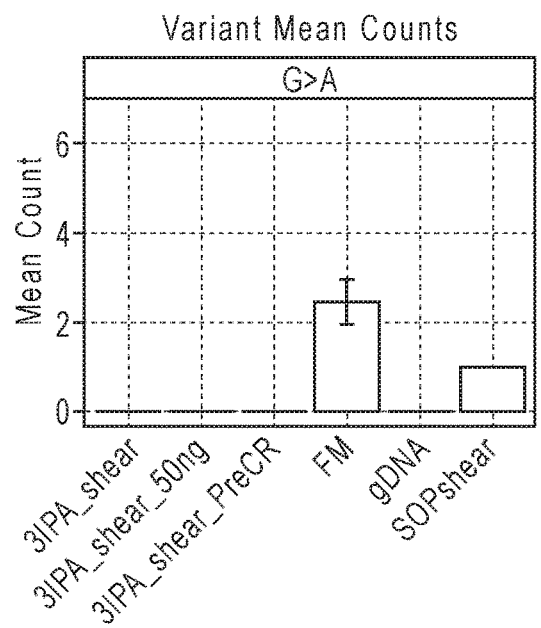
Figure 3E:
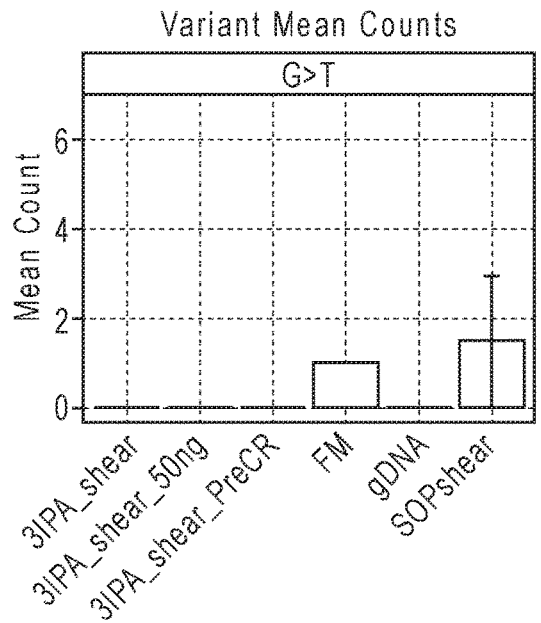
Figure 3F:
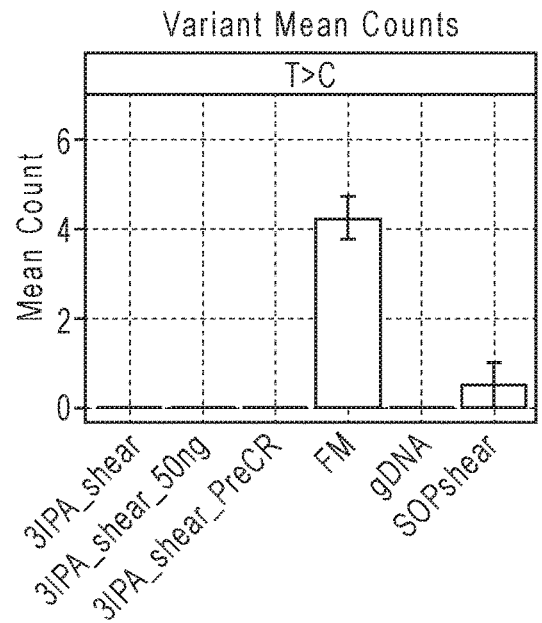
Figure 3G:
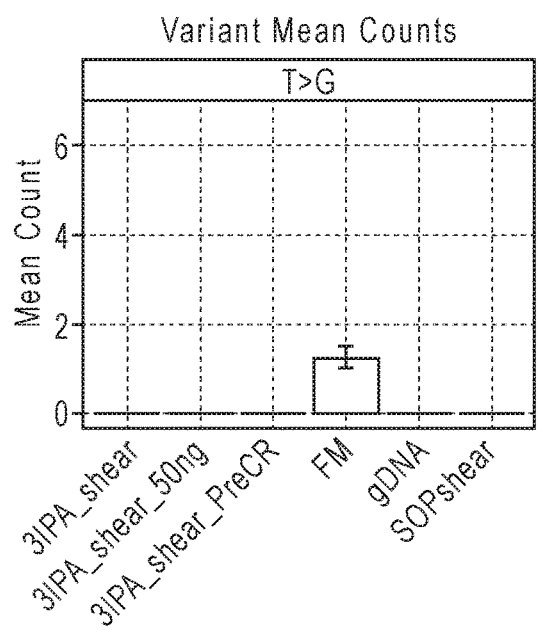

In FIGS. 3A-G, the x-axis for each chart represents the different shearing conditions with or without reagents (from left to right): 3IPA shear; 3IPA shear 50 ng; 3IPA shear PreCR; FM; gDNA; and SOP shear. The y-axis for each chart represents the mean count of variant sequences, which correlates with artifact base transitions or transversions, including C>A, C>T, G>A, G>T, T>C, or T>G. Data in FIGS. 3A-G demonstrate that shearing DNA in the presence of 3-indole-propionic acid reduces mutation artifacts that arise in the form of base substitutions, including base transitions and base transversions. FIGS. 3B, D, E and F show that control DNA prepared by shearing in the presence of 3-indole-propionic acid (3IPA shear and 3IPA shear 50 ng) exhibit reduced damage as base transitions or base transversions compared to DNA that is sheared without 3-indole-propionic acid (FM and SOP shear). Also, FIGS. 3B-G show that PreCR Repair Mix did not repair shear-induced damage (3IPA shear PreCR).

Example 4: Reducing False Positive Sequencing Reads

To determine if reducing mutation artifacts that arise from shear-damage in the form of base transitions and/or base transversion can also reduce the number of false positive sequencing reads, control DNA was prepared by shearing input DNA with TE, or with 3-indole-propionic acid, or EDTA, or with 3-indole-propionic acid and EDTA.

Figure 4A:
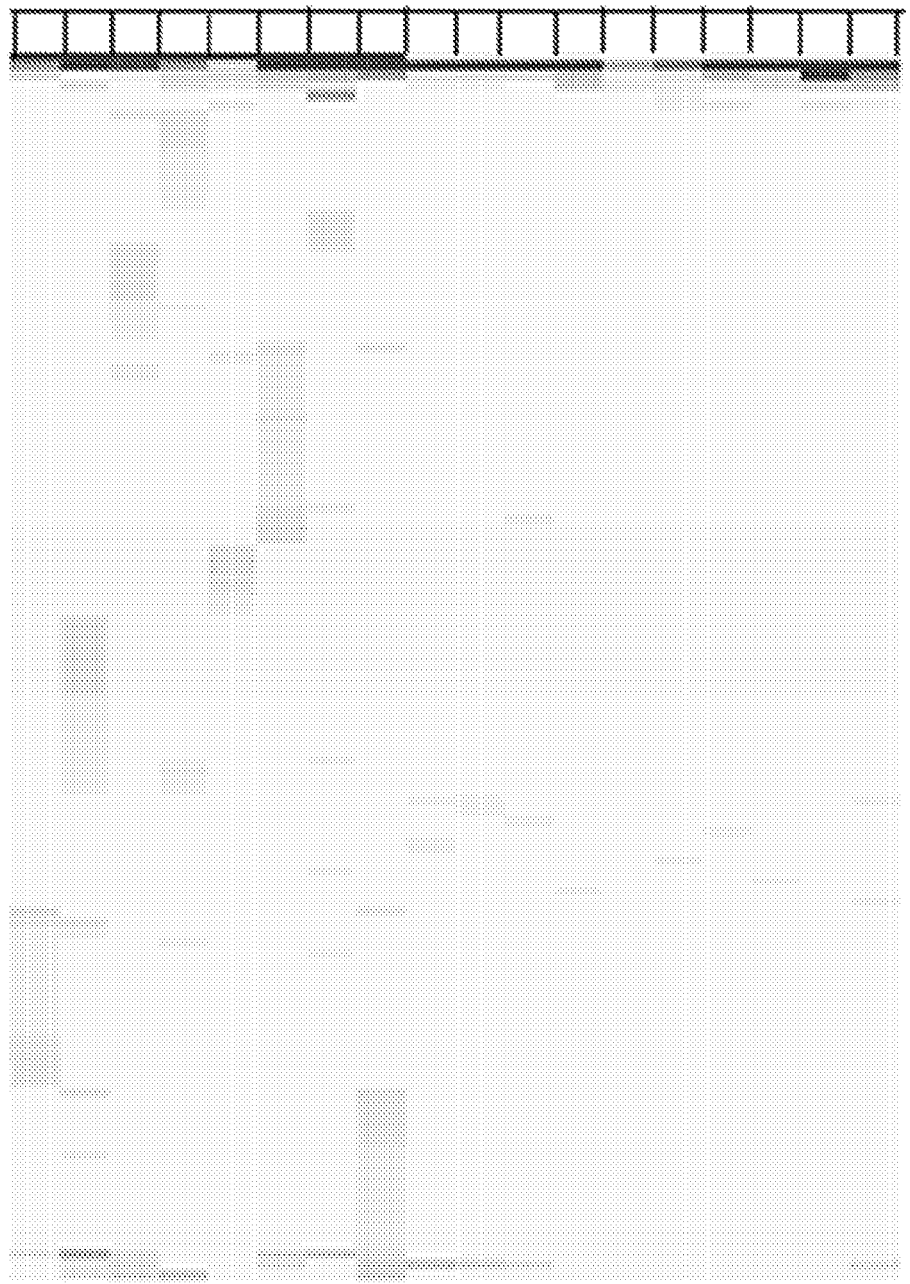
FIGS. 4A and B depict detection of mutation artifacts that arise from shear-damage in the form of base transitions and base transversions. Control DNA was sheared with or without 3-indole-propionic acid (and some samples sheared with or without EDTA), then uniquely tagged using a breast primer panel, and sequenced using a massively parallel sequencing platform, as described in Example 4.
Figure 4B:
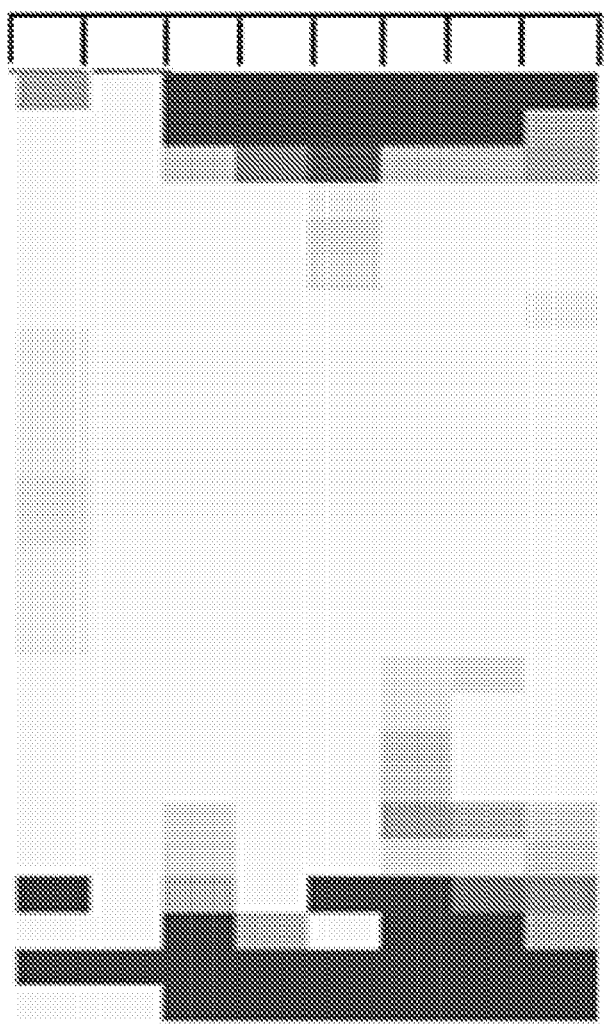
FIG. 4B shows the level of false positive sequencing reads from control DNA prepared by shearing GM24385 DNA.

Control DNA was prepared as described in Example 1. Input DNA as AcroMetrix™ Oncology Hotspot Control DNA (e.g., containing 50% allelic frequencies) was sheared with TE or with 3-indole-propionic acid but no EDTA (FIG. 4A). Input genomic DNA as GM24385 DNA (Coriell Institute for Medical Research, catalog No. NA24385) was sheared with only 3-indole-propionic acid, or sheared only with EDTA, or sheared with both 3-indole-propionic acid and EDTA (FIG. 4B). Control DNA was used to generate molecular tagged libraries using Oncomine® Breast cfDNA Assay kit (catalog No. A31183 from Thermo Fisher Scientific). The molecular tagged libraries were prepared for sequencing on an Ion Torrent semiconductor sequencing chip according to manufacturer's instructions (kit catalog Nos. A25592, A30798, A26772 and A26433, all from Thermo Fisher Scientific).

In FIGS. 4A and B, depicts detection of different sequences of interest, targeted by the breast primer panel, listed in Table 5 (FIG. 4A) and Table 6 (FIG. 4B). The target sequences listed top to bottom in each column in Tables 5 and 6 correspond to the target sequences in the graphs listed top to bottom of their respective Figures. In FIGS. 4A and B, the lighter shaded regions in the center represent control DNA samples having zero false positive or a reduced number of false positive sequencing reads that are associated with reduced mutation artifacts from base transitions and base transversions, while the darker shaded regions represent an increased number of false positive sequencing reads that are associated with an increased level of mutation artifacts from base transitions and base transversions.

FIG. 4A shows sequencing data representing control DNA prepared by separately shearing Acrometrix and GM24385 DNAs and then mixing the sheared DNAs to make a desired dilution series. FIG. 4A: Each column, labeled at the top from left to right, represents control DNA prepared by shearing with TE and without 3-indole-propionic acid or EDTA (lanes 1-8), or sheared in the presence of only 3-indole-propionic acid (lanes 9-18). Each row represents one of 122 different variant base changes (see Table 7) detected by sequencing the control DNA. Results show that control DNA sheared in the presence of 3-indole-propionic acid (lanes 9-18) exhibit reduced false positive sequencing reads, compared to control DNA sheared without 3-indole-propionic acid (lanes 1-8).

FIG. 4B shows sequencing data representing control DNA prepared by shearing GM24385 DNA and then preparing a dilution series. FIG. 4B: Each column, labeled at the top from left to right, represents control DNA sheared in the presence of EDTA only (lane 1), sheared in the presence of 3-indole-propionic acid and EDTA (lane 2), or sheared in the presence of only 3-indole-propionic acid (lanes 3-8). Each row represents one of 26 different variant base changes (See Table 8) detected by sequencing the control DNA. Results show that control DNA sheared in the presence of 3-indole-propionic acid and EDTA (lane 2) exhibits reduced false positive sequencing reads, compared to control DNA sheared with EDTA only (lane 1) or sheared with only 3-indole-propionic acid (lanes 3-8).

Example 5: Reducing False Positive Sequencing Reads

To determine if reducing mutation artifacts that arise from shear-damage in the form of base transitions and/or base transversion can also reduce the number of false positive sequencing reads, control DNA was prepared by shearing input DNA with TE, or with 3-indole-propionic acid, or EDTA, or with 3-indole-propionic acid and EDTA.

Figure 5A:
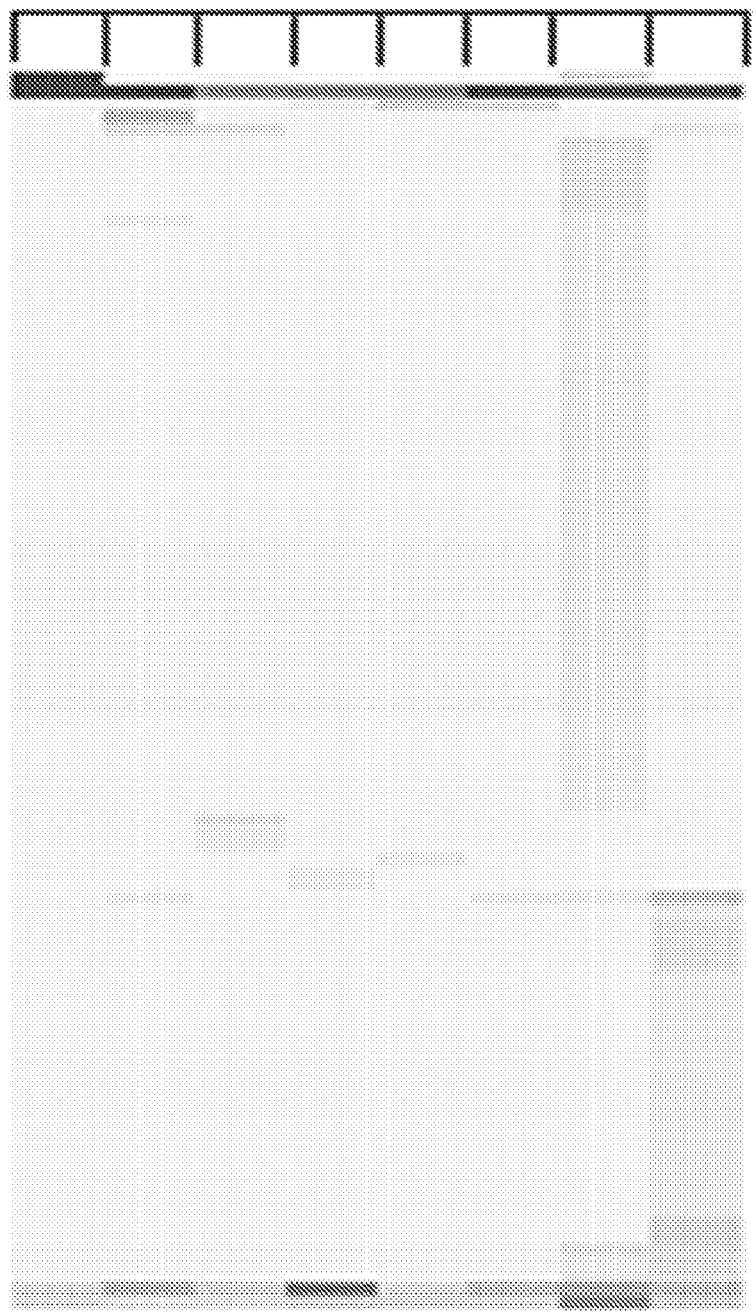
FIGS. 5A and B depict detection of mutation artifacts that arise from shear-damage in the form of base transitions and base transversions. Control DNA was sheared with or without 3-indole-propionic acid (and some samples sheared with or without EDTA), then uniquely tagged using a lung primer panel, and sequenced using a massively parallel sequencing platform, as described in Example 5.
Figure 5B:
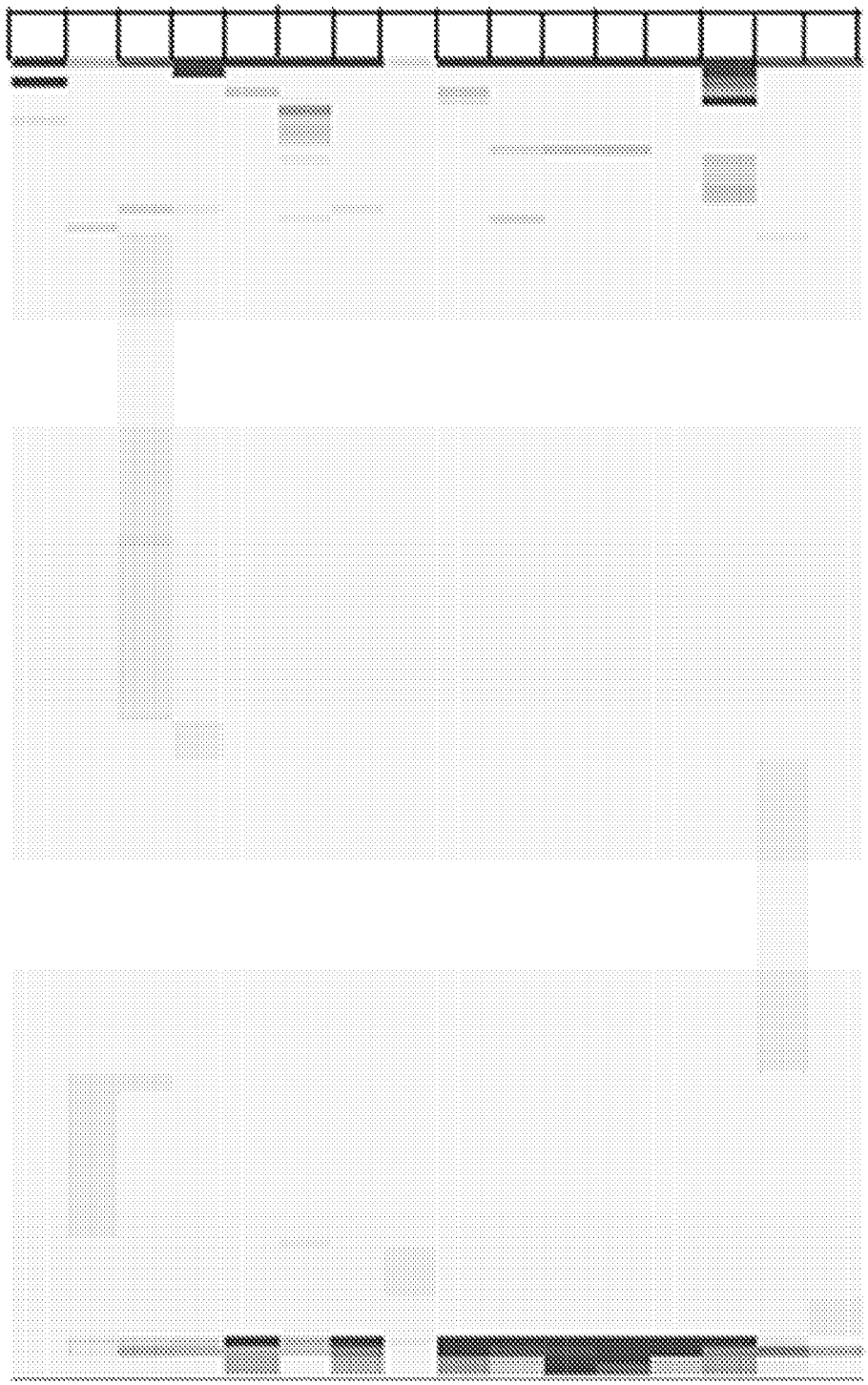
FIG. 5B shows the level of false positive sequencing reads from control DNA prepared by shearing GM24385 DNA.

Control DNA was prepared as described in Example 1. Input DNA as AcroMetrix™ Oncology Hotspot Control DNA (e.g., containing 50% allelic frequencies) was sheared with TE or with 3-indole-propionic acid but no EDTA (FIG. 5A). Input genomic DNA as GM24385 DNA (Coriell Institute for Medical Research, catalog No. NA24385) was sheared with TE, or sheared with only 3-indole-propionic acid, or sheared only with EDTA, or sheared with both 3-indole-propionic acid and EDTA (FIG. 5B). Non-fragmented GM24385 DNA was included for comparison. Control DNA was used to generate molecular tagged libraries using Oncomine® Lung cfDNA Assay kit (catalog No. A31149 from Thermo Fisher Scientific). The molecular tagged libraries were prepared for sequencing on an Ion Torrent semiconductor sequencing chip according to manufacturer's instructions (kit catalog Nos. A25592, A30798, A26772 and A26433, all from Thermo Fisher Scientific).

In FIGS. 5A and B, different sequences of interest, targeted by the lung primer panel, are listed in Table 7 (FIG. 5A) and Table 8 (FIG. 5B). The target sequences listed top to bottom in each column in Tables 7 and 8 correspond to the target sequences in the graphs listed top to bottom of their respective Figures. In FIGS. 5A and B, the lighter shaded regions in the center represent control DNA samples having zero false positive or a reduced number of false positive sequencing reads that are associated with reduced mutation artifacts from base transitions and base transversions, while the darker shaded regions represent an increased number of false positive sequencing reads that are associated with an increased level of mutation artifacts from base transitions and base transversions.

FIG. 5A shows sequencing data representing control DNA prepared by separately shearing Acrometrix and GM24385 DNAs and then mixing the sheared DNAs to make a desired dilution series. FIG. 5A: Each column, labeled at the top from left to right, represents DNA sheared with 3-indole-propionic acid (lanes 1-6), or sheared with TE (lanes 7-8). Each row represents one of 95 different variant base changes (see Table 7) detected by sequencing the control DNA. Results show that control DNA sheared in the presence of 3-indole-propionic acid (lanes 1-6) exhibit reduced false positive sequencing reads, compared to control DNA sheared without 3-indole-propionic acid (lanes 7-8).

FIG. 5B shows sequencing data representing control DNA prepared by shearing GM24385 DNA and then preparing a dilution series. FIG. 5B: Each column, labeled at the top from left to right, represents non-fragmented DNA (lane 1), DNA sheared using standard conditions using TE (lanes 2-3), DNA prepared by shearing with 3-indole-propionic acid (lanes 4-14), DNA sheared with EDTA (lane 15), and DNA sheared with 3-indole-propionic acid and EDTA (lane 16). Each row represents one of 135 different variant base changes (see Table 8) detected by sequencing the control DNA. Results show that control DNA prepared by shearing in the presence of 3-indole-propionic acid and EDTA (lane 15) exhibit reduced false positive sequencing reads, compared to control DNA sheared without 3-indole-propionic acid and EDTA (lanes 2-14).

Example 6: Reducing False Positive Sequencing Reads

To determine if reducing mutation artifacts that arise from shear-damage in the form of base transitions and/or base transversion can also reduce the number of false positive sequencing reads, control DNA was prepared by shearing input DNA with TE, or with 3-indole-propionic acid, or EDTA, or with 3-indole-propionic acid and EDTA.

Figure 6A:
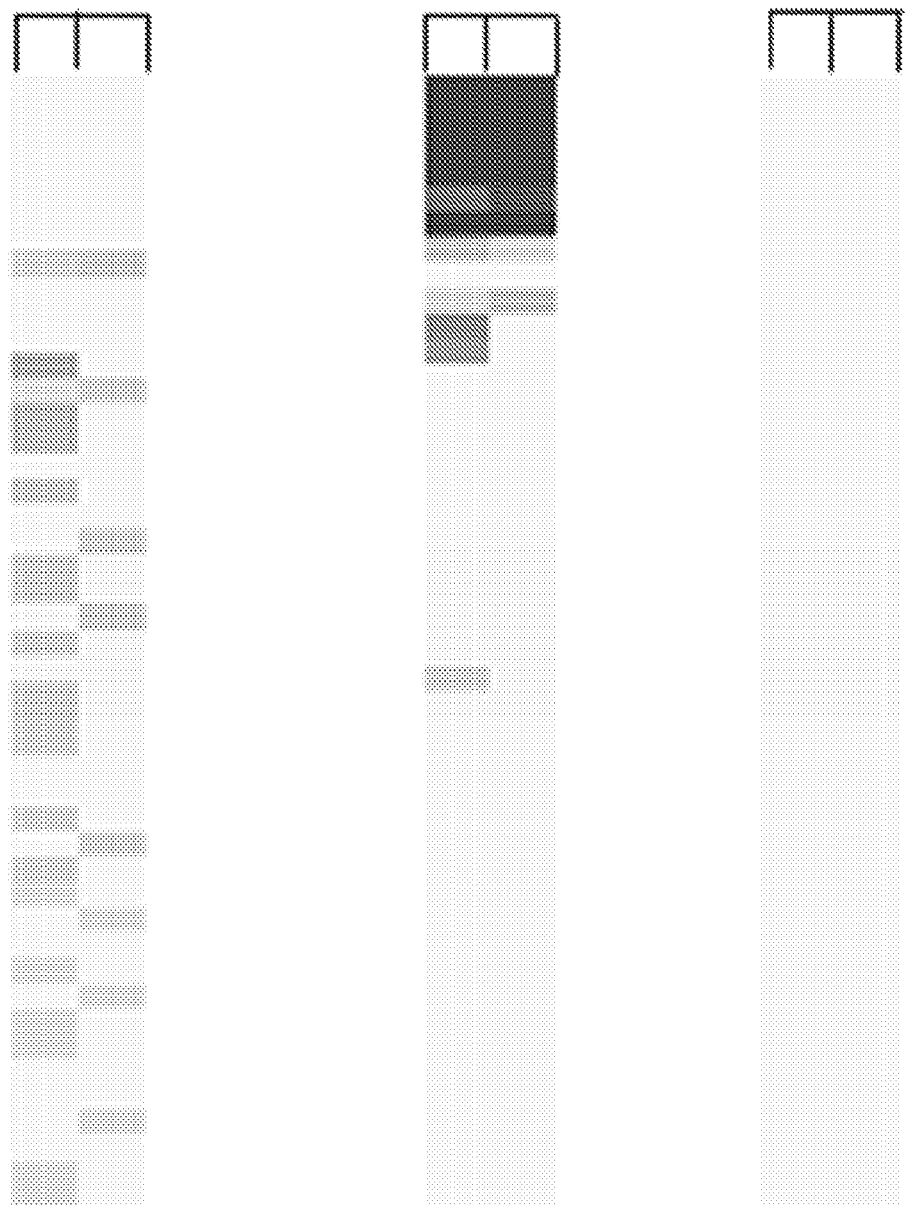
FIGS. 6A and B depict detection of mutation artifacts that arise from shear-damage in the form of base transitions and base transversions. Control DNA was sheared with or without 3-indole-propionic acid (and some samples sheared with or without EDTA), then uniquely tagged using a colon primer panel, and sequenced using a massively parallel sequencing platform, as described in Example 6.
Figure 6B:
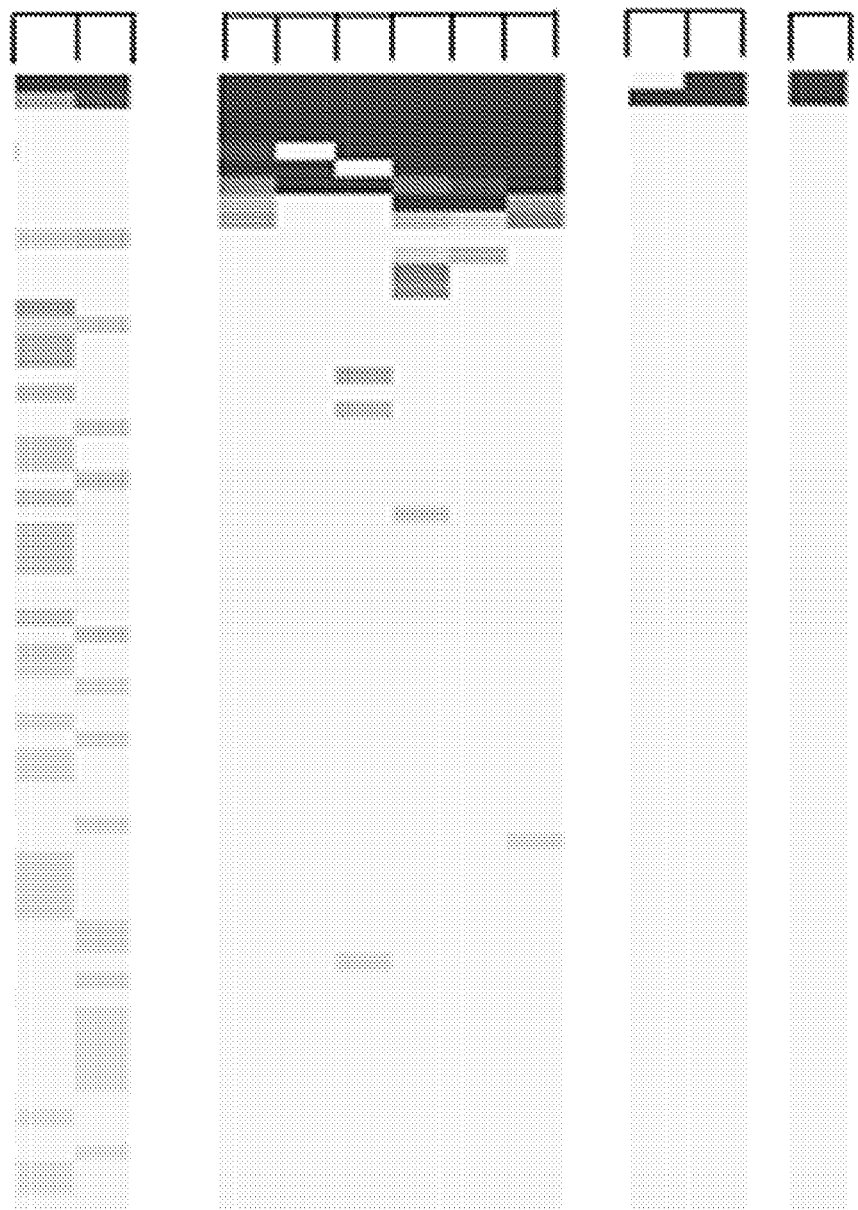
FIG. 6B shows the level of false positive sequencing reads from control DNA prepared by shearing GM24385 DNA.

Control DNA was prepared as described in Example 1. Input DNA as AcroMetrix™ Oncology Hotspot Control DNA (e.g., containing 50% allelic frequencies) was sheared with TE or with 3-indole-propionic acid or with 3-indole-propionic acid and EDTA (FIG. 6A). Input genomic DNA as GM24385 DNA (Coriell Institute for Medical Research, catalog No. NA24385) was sheared with TE, or sheared with only 3-indole-propionic acid, or sheared only with EDTA, or sheared with both 3-indole-propionic acid and EDTA (FIG. 6B). Non-fragmented GM24385 DNA was included for comparison. Control DNA was used to generate molecular tagged libraries using Oncomine® Colon cfDNA Assay kit (catalog No. A31182 from Thermo Fisher Scientific). The molecular tagged libraries were prepared for sequencing on an Ion Torrent semiconductor sequencing chip according to manufacturer's instructions (kit catalog Nos. A25592, A30798, A26772 and A26433, all from Thermo Fisher Scientific).

In FIGS. 6A and B, different sequences of interest, targeted by the colon primer panel, are listed in Table 0 (FIG. 6A) and Table 10 (FIG. 6B). The target sequences listed top to bottom in each column in Tables 9 and 10 correspond to the target sequences in the graphs listed top to bottom of their respective Figures. In FIGS. 6A and B, the lighter shaded regions in the center represent control DNA samples having zero false positive or a reduced number of false positive sequencing reads that are associated with reduced mutation artifacts from base transitions and base transversions, while the darker shaded regions represent an increased number of false positive sequencing reads that are associated with an increased level of mutation artifacts from base transitions and base transversions.

FIG. 6A shows sequencing data representing control DNA prepared by separately shearing Acrometrix and GM24385 DNAs and then mixing the sheared DNAs to make a desired dilution series. FIG. 6A: Each column, labeled at the top from left to right, represents DNA sheared with TE (lanes 1-2), or sheared with 3-indole-propionic acid (lanes 3-4), or sheared with 3-indole-propionic acid and EDTA (lanes 5-6). Each row represents one of 45 different variant base changes (see Table 9) detected by sequencing the control DNA. Results show that control DNA sheared in the presence of 3-indole-propionic acid and EDTA (lanes 5-6) exhibit reduced false positive sequencing reads, compared to control DNA sheared with only 3-indole-propionic acid (lanes 3-4) or sheared with TE (lanes 1-2).

FIG. 6B shows sequencing data representing control DNA prepared by shearing GM24385 DNA and then preparing a dilution series. FIG. 6B: Each column, labeled at the top from left to right, represents DNA sheared with TE (lanes 1-2), sheared with 3-indole-propionic acid (lanes 3-8), sheared with 3-indole-propionic acid and EDTA (lanes 9-10), and non-fragmented DNA (lane 11). Each row represents one of 66 different variant base changes (see Table 12) detected by sequencing the control DNA. Results show that control DNA prepared by shearing in the presence of 3-indole-propionic acid and EDTA (lanes 9-10) exhibit reduced false positive sequencing reads, compared to control GM24385 DNA sheared with TE (lanes 1-2) or sheared with only 3-indole-propionic acid (lanes 3-8).

Example 7: Preparing Control DNA

Two input DNAs are sheared separately and then mixed together to achieve a preparation of control DNA that contains known sequence variants at specified concentrations (allelic frequencies). One input DNA is normal background genomic DNA. An example of normal background DNA is GM24385 which can be obtained from Coriell Institute for Medical Research (catalog No. NA24385) or from Horizon Discovery (catalog No. GM24385). Another input DNA is a mixture of DNAs from different plasmid constructs that provide known variant sequences (e.g., hotspot mutations associated with cancer). A mixture of plasmid constructs can contain 1-50,000 different variant sequences. In the mixture, individual plasmid constructs contain a plasmid joined to at least one insert sequence having a known sequence. Known sequences include a known wild-type or known variant sequence. Plasmid constructs can include at least one restriction endonuclease recognition sequence that flanks the insert sequence to enable release of the insert sequence upon treatment with an appropriate restriction enzymes. Some plasmid constructs can contain multiple insert sequences, where each insert contains a different known sequence. Optionally, restriction endonuclease recognition sequences are located between the different inserts to permit release of the different insert sequences (e.g., cassettes which are described in U.S. published application No. 2015/0133314, entitled Reagents and Methods for Sequencing, which is incorporated herein by reference in its entirety). Inserts that contain variant sequences include at least one single nucleotide polymorphism (SNP), one or more multiple nucleotide polymorphisms (MNPs), substitution, insertion, deletion, rearrangement, aberrant splice junction, truncation, transversion, nonsense mutation, gene fusion, duplication, inversion, repeat polymorphism, or homopolymer sequence. A known sequence represents a wild-type or variant sequence from at least one human chromosome, including chromosome 1, 2, 3, 4, 5, 6, 7, 8, 9, 10, 11, 12, 13, 14, 15, 16, 17, 18, 19, 20, 21, 22, X or Y. Variant sequences of interest include KRAS (p.G12D); PIK3CA (p.E545K); EGFR (p.E746_A750delELREA); and EGFR (p.790M).

A mixture of plasmid constructs can contain a single type of plasmid or a mixture of different types of plasmids. Plasmids are extrachromosomal DNA that can be amplified in a host bacteria or yeast cell. Selection of the type of plasmid can be based on available restriction enzyme sites for insertion and/or based on available amplification primer binding sites. Plasmid constructs are amplified by transforming host cells to take in the plasmids, growing the transformed bacteria, lysing the grown bacteria and isolating the plasmid constructs from the lysate. The isolated plasmid constructs contain at least one insert sequence. Alternatively, the insert sequences can be amplified by performing PCR using primer binding sites in the plasmid construct.

The two input DNAs are sheared separately. The concentration of each of the input DNA is typically 250-500 ng/uL for GM24385 and about 40-60 ng/uL for plasmid constructs. For each input DNA to be sheared, a Covaris water bath is filled to level 12 and degassed for 30 minutes prior to shearing. A microTUBE is placed in the holder, with water level at the base of the cap and the glass portion of the microTUBE completely submerged. The chiller is set to 4° C.

Input DNA (100 ng-10 ug) is placed in an Eppendorf tube. Low TE is added to the input DNA to bring total volume to 127.4 µl. 1.3 µl of 100 mM EDTA is added. Add 1.3 µl of 100 mM 3-indole propionic acid dissolved in methanol for an effective concentration of 1 mM. Keeping the cap on the tube, transfer the entire volume into the 130 µl Covaris microTUBE by inserting the pipette tip through the pre-split septa. Be careful not to introduce any bubbles, especially in the bottom of the tube. Load the sample tube into the Covaris Sample holder.

One mL working stock of 100 mM 3-indole propionic acid is prepared by dissolving 18.9 mg 3-indole propionic acid (MP Biomedicals 10204810) in 1 mL 100% methanol (Fisher Scientific A452-1).

The process configuration for the Covaris S2 system is set up based on the following table:

TABLE 4

| For genomic DNA (GM24385): Number of Cycles: 6 |
|---|
| For plasmid DNA: Number of Cycles: 1 |
| Bath Temperature 5° C. |
| Bath Temperature Limit: 30° C. |
| Mode: Frequency sweeping |
| Water Quality Testing Function: Off |
| Duty Cycle: 10% |
| Intensity: 5 |
| Cycles/burst: 100 |
| Time: 60 s |

The process is initiated by clicking "START" to run.

Shearing conditions for preparing control DNA will yield fragmented DNA in a size range of about 50-300 bp.

After shearing process is completed, the entire volume of 130 µl of sheared DNA is transferred to 1.5 ml nuclease-free low adhesion tubes by inserting the pipette tip through the pre-split septa and slowly removing the fluid. The snap-cap is removed to ensure all the volume was recovered.

Concentrating the DNA: 260 µl of Agencourt AMPure beads (2 volumes) is added to the sample and incubated for 10 minutes at room temperature on a rotator.

The sample tube was placed in a magnetic rack until the solution becomes clear.

The supernatant is removed and discarded.

500 µL of freshly prepared 80% ethanol is added. The bead pellet is washed by lifting the tube, turning it 180° and then placing it back in the rack. This washing step is performed a total of 6 times to wash thoroughly. Turning the tube allows the magnet to declump the beads and prevents the need for vigorous vortexing. Using freshly prepared 80% ethanol is critical as a higher percentage will result in an inefficient washing of smaller-sized molecules and using lower than 80% ethanol could cause loss of sample.

The tube of sample is placed in the magnetic rack and the supernatant was removed. The tube was pulse-spun to remove the residual ethanol.

The beads are air-dried completely at room temperature approximately 5 minutes.

25 µL low TE is added to the sample and vortexed for 10 seconds. The solution is pipetted up and down several times to ensure homogeneity.

The tube of sample is placed in the magnetic rack. After the solution cleared, the eluted sample (supernatant) is transferred into a new 1.5-mL LoBind tube.

Sheared nucleic acids can be stored in low TE at −20° C.

Quantstudio 3D Digital PCR System (from Thermo Fisher Scientific, catalog No. A29154) is used to quantitate the sheared DNAs according to the manufacturer's instructions. A dilution series is prepared by mixing sheared GM24385 with sheared plasmid DNA to achieve 4.8%, 1.1%, 0.5% and 0.1% variant sequence frequency in a background of GM24385 DNA (according to Quantstudio manufacturer's instructions). These dilutions are used to prepare several control DNAs which contain either 0.01%, 0.05%, 0.1% or 1% variant sequence frequency in a background of GM24385 DNA. Digital PCR is used to confirm the variant sequence frequency of the dilution series. In a 0.1% diluted control DNA preparation, each of the known variant sequences are present in the control DNA preparation at the same concentration of about 0.1%. The same can be applied to the other diluted control DNA preparations (e.g., 0.05%, 0.1% and 1%).

A control nucleic acid prepared by any of the methods described in the present teachings contains a reduced level of damage and a reduced level of artifact sequence mutations, compared to input nucleic acids that are sheared in the absence of at least one damage mitigating reagent and/or at least one chelating reagent.

A control nucleic acid prepared by any of the methods described in the present teachings can be used as a reference nucleic acid in a massively parallel sequencing workflow to monitor the sensitivity, accuracy and/or precision of the sequencing data of a test sample. Since a control nucleic acid contains reduced damage and artifact sequence mutations, the control nucleic acid can yield sequencing data having reduced (or zero) false positive sequencing reads.

A control DNA prepared by any of the methods described in the present teachings comprises at least one known sequence (e.g., a variant or wild-type sequence) from human chromosomes, including chromosomes 1, 2, 3, 4, 5, 6, 7, 8, 9, 10, 11, 12, 13, 14, 15, 16, 17, 18, 19, 20, 21, 22, X and Y. A known sequence can be associated with a disease or abnormal condition, including any type of cancer.

A control DNA prepared by any of the methods described in the present teachings contains a mixture of at least one known sequence (e.g., variant or wild-type sequence) and background nucleic acids, where the known sequence is present at a low abundance level that mimics a sequence-of-interest in a test nucleic acid sample, to validate that a sequencing workflow is capable of accurately detecting and analyzing these low abundance species. Methods for preparing a control DNA can be used to prepare a dilution series containing known sequence frequencies ranging from 0.0001-10%.

A control DNA prepared by any of the methods described in the present teachings contains a mixture of at least one known sequence (e.g., variant or wild-type sequence) and background nucleic acids that are fragmented to a size range that mimics the size range of nucleic acids in a test sample. A control DNA can contain nucleic acid fragments ranging from about 100-250 bp.

Molecular Tagging Procedures:

Molecular tagged libraries are generated from the prepared diluted control DNA using the Oncomine® Lung cfDNA Assay kit (catalog No. A31149 from Thermo Fisher Scientific) according to manufacturer's instructions. The library panel contains uniquely tagged primers that target ALK, BRAF, EGFR, ERBB2, KRAS, MAP2K1, MET, NRAS, PIK3CA, ROS1 and TP53, and more than 150 mutation hotspots including EFGR (T790M, C797S, L858R and exon 19-del), KRAS (G12X, G13X and Q61X), BRAF (V600E), ALK (exon21-25) and PIK3CA (E545K, H104R and E542K).

Molecular tagged libraries are also generated from the prepared diluted control DNA (prepared as described in Example 1) using the Oncomine® Colon cfDNA Assay kit (catalog No. A31182 from Thermo Fisher Scientific) according to manufacturer's instructions. The library panel contains uniquely tagged primers that target AKT1, APC, BRAF, CTNNB1, EGFR, ERBB2, FBXW7, GNAS, KRAS, MAP1K1, NRAS, PIK3CA, SMAD4 and TP53, and more than 240 mutation hotspots including KRAS/NRAS (G12/G13/Q61), BRAF (V600E), PIK3CA (E545K and H104R), TP53 (R175H and R273H/C/L), recurring deleterious APC mutations (p.R876*, p.R1114*, p.Q1378* and p.R1450*), SMAD4 (R361C/H) and CTNNB1 (S45F and T41A).

Molecular tagged libraries are also generated from the prepared diluted control DNA (prepared as described in Example 1) using the Oncomine® Breast cfDNA Assay kit (catalog No. A31183 from Thermo Fisher Scientific) which contains uniquely tagged primers that target AKT1, EGFR, ERBB2, ERBB3, ESR1, FBXW7, KRAS, PIK3CA, SF3B1 and TP53, and more than 150 mutation hotspots including PIK3CA (E545K and H104R), AKT1 (E17K), ESR1 (mutations associated with anti-estrogen resistance), TP53 (mutations associates with loss of function) and ERBB2 (mutations associated with sensitivity to anti-ERBB2 therapies).

Resulting prepared libraries using control DNA are each prepared for sequencing on an Ion Torrent semiconductor sequencing chip according to manufacturer's instructions (kit catalog Nos. A25592, A30798, A26772 and A26433, all from Thermo Fisher Scientific). Sequencing data is analyzed to determine the allelic frequency of known variant sequences contained in the dilution series (control DNA), which can be compared with the allelic frequency of the same variant sequences present in a test nucleic acid sample.

TABLE 5

(See FIG. 4A):

| Variants detected with base changes | Amplicon identification: |
|---|---|
| Chr17.7578279; AG.A | TP53_chr17_7578268 |
| Chr3.178927977; C.CT | PIK3CA_chr3_178927980 |
| Chr3.178952085; A.G | PIK3CA_SP_28.120542 |
| Chr17.37880220; T.C | ERBB2_chr17_37880220 |
| Chr3.178938897; T.TA | PIK3CA_chr3_178938934 |
| Chr3.178921553; T.A | PIK3CA_chr3_178921553 |
| Chr14.105246565; C.A | AKT1_chr14_105246551 |
| Chr17.7578407; G.T | TP53_chr17_7578403 |
| Chr17.7578474; C.A | TP53_chr17_7578479 |
| Chr3.178927950; G.T | PIK3CA_chr3_178927980 |
| Chr3.178936078; C.A | PIK3CA_SP_27.58329 |
| Chr17.7578475; G.T | TP53_chr17_7578479 |
| Chr17.7577091; G.T | TP53_chr17_7577118 |
| Chr17.7577547; C.A | TP53_chr17_7577547 (p.Gly245Val) |
| Chr4.153245453; G.T | FBXW7_chr4_153245446 |
| Chr7.55259475; G.C | EGFR_chr7_55259485 |
| Chr2.198266827; C.A | SF3B1_chr2_198266834 |
| Chr12.56478854; G.T | ERBB3_chr12_56478854 (p.V104L) |
| Chr6.152419921; C.A | ESR1_chr6_152419923 |
| Chr17.7577549; G.T | TP53_chr17_7577547 |
| Chr17.37880235; C.A | ERBB2_chr17_37880220 |
| Chr6.152415520; G.T | ESR1_chr6_152415537 |
| Chr2.198266820; G.T | SF3B1_chr2_198266834 |
| Chr12.56478842; C.A | ERBB3_chr12_56478854 |
| Chr12.56482597; G.A | ERBB3_chr12_56482607 |
| Chr4.153245400; C.A | FBXW7_chr4_153245446 |
| Chr17.7577522; G.T | TP53_chr17_7577547 |
| Chr7.55259450; C.A | EGFR_chr7_55259485 |
| Chr7.55259513; G.A | EGFR_chr7_55259485 |
| Chr12.56492646; G.T | ERBB3_chr12_56492633 |
| Chr17.7577539; G.T | TP53_chr17_7577547 |
| Chr17.7577082; C.A | TP53_chr17_7577118 |
| Chr4.153245411; G.T | FBXW7_chr4_153245446 |
| Chr7.55259525; G.T | EGFR_chr7_55259485 |
| Chr7.55259445; C.A | EGFR_chr7_55259485 |
| Chr7.55259468; C.A | EGFR_chr7_55259485 |
| Chr12.56482624; C.A | ERBB3_chr12_56482607 |
| Chr7.55259451; G.T | EGFR_chr7_55259485 |
| Chr3.178921540; C.A | PIK3CA_chr3_178921553 |
| Chr17.7578497; G.T | TP53_chr17_7578479 |
| Chr17.7578495; C.A | TP53_chr17_7578479 |
| Chr17.7577555; G.T | TP53_chr17_7577547 |
| Chr17.7577137; C.A | TP53_chr17_7577118 |
| Chr12.56481946; C.A | ERBB3_chr12_56481922 |
| Chr17.7577124; C.A | TP53_chr17_7577118 (p.Val272Leu) |
| Chr17.7578468; G.T | TP53_chr17_7578479 |
| Chr3.178921532; T.TA | PIK3CA_chr3_178921553 |
| Chr17.7578388; C.A | TP53_chr17_7578403 |
| Chr3.178921550; G.T | PIK3CA_chr3_178921553 |
| Chr14.105246543; G.T | AKT1_chr14_105246551 |
| Chr17.7578385; C.A | TP53_chr17_7578403 |
| Chr2.198266809; G.T | SF3B1_chr2_198266834 |
| Chr12.56482362; G.T | ERBB3_chr12_56482341 |
| Chr3.178928087; G.T | PIK3CA_chr3_178928079 |
| Chr17.7577125; C.A | TP53_chr17_7577118 |
| Chr17.7578481; G.T | TP53_chr17_7578479 |
| Chr3.178938931; G.T | PIK3CA_chr3_178938934 |
| Chr6.152419930; G.T | ESR1_chr6_152419923 |
| Chr6.152419928; C.A | ESR1_chr6_152419923 |
| Chr2.198266826; C.A | SF3B1_chr2_198266834 |
| Chr17.7578406; C.A | TP53_chr17_7578403 (p.Arg175Leu) |
| Chr17.7577547; G.T | TP53_chr17_7578403 |
| Chr12.56478860; C.A | ERBB3_chr12_56478854 |
| Chr12.56481934; G.T | ERBB3_chr12_56481922 |
| Chr7.55259516; G.T | EGFR_chr7_55259485 |
| Chr7.55259513; G.T | EGFR_chr7_55259485 |
| Chr6.152332832; G.T | ESR1_chr6_152332832 |
| Chr4.153245426; G.T | FBXW7_chr4_153245446 |
| Chr12.56481939; C.A | ERBB3_chr12_56481922 |
| Chr12.56481945; C.A | ERBB3_chr12_56481922 |
| Chr4.153245434; C.A | FBXW7_chr4_153245446 |
| Chr12.56482642; C.A | ERBB3_chr12_56482607 |
| Chr7.55259495; C.A | EGFR_chr7_55259485 |
| Chr7.55259514; C.A | EGFR_chr7_55259485 |
| Chr7.55259446; AC.A | EGFR_chr7_55259485 (SYS_ERR) |
| Chr17.7578463; C.T | TP53_chr17_7578479 |
| Chr17.7578457; C.T | TP53_chr17_7578479 (p.Arg158His) |
| Chr17.7578262; C.T | TP53_chr17_7578268 |
| Chr17; 7577091; G.A | TP53_chr17_7577118 |
| Chr17; 7577103; C.G | TP53_chr17_7577118 |
| Chr7.55259468; C.T | EGFR_chr7_55259485 |
| Chr4.153245402; C.A | FBXW7_chr4_153245446 |
| Chr17.7578500; G.A | TP53_chr17_7578479 |
| Chr17.7578462; G.A | TP53_chr17_7578479 |
| Chr17.7578464; G.A | TP53_chr17_7578479 |
| Chr3.178921564; G.T | PIK3CA_chr3_178921553 |
| Chr6.152415534; C.A | ESR1_chr6_152415537 |
| Chr17.7577131; G.T | TP53_chr17_7577118 |
| Chr17.7577122; C.A | TP53_chr17_7577118 |
| Chr7.55259465; G.T | EGFR_chr7_55259485 |
| Chr7.55259489; G.T | EGFR_chr7_55259485 |
| Chr4.153245406; G.T | FBXW7_chr4_153245446 |
| Chr17.7577112; C.A | TP53_chr17_7577118 |
| Chr12.56482620; C.A | ERBB3_chr12_56482607 |
| Chr12.56482608; C.A | ERBB3_chr12_56482607 |
| Chr12.56478861; G.T | ERBB3_chr12_56478854 |
| Chr12.56478840; TG.T | ERBB3_chr12_56478854 |
| Chr12.56478859; G.T | ERBB3_chr12_56478854 |
| Chr12.56492636; G.T | ERBB3_chr12_56492633 |
| Chr17.7578403; C.A | TP53_chr17_7578403 (p.Cys176Phe) |
| Chr6.152419956; G.T | ESR1_chr6_152419923 |
| Chr3.178936097; G.T | PIK3CA_SP_27.58329 |
| Chr3.178938745; C.A | PIK3CA_chr3_178938934 |
| Chr17.7578195; C.A | TP53_chr17_7578211 |
| Chr17.7578287; G.T | TP53_chr17_7578268 |
| Chr6.152332843; G.T | ESR1_chr6_152332832 |
| Chr2.198266837; G.T | SF3B1_chr2_198266834 |
| Chr14.105246526; C.A | AKT1_chr14_105246551 |
| Chr17.7577543; C.A | TP53_chr17_7577547 |
| Chr3.178927948; G.T | PIK3CA_chr3_178927980 |
| Chr7.55259474; G.T | EGFR_chr7_55259485 |
| Chr17.7577547; C.T | TP53_chr17_7577547 (p.Gly245Asp) |
| Chr17.7577141; C.A | TP53_chr17_7577118 (p.Gly266Val) |
| Chr12.56482351; C.A | ERBB3_chr12_56482341 |
| Chr12.56482344; C.A | ERBB3_chr12_56482341 |
| Chr12.56482316; C.A | ERBB3_chr12_56482341 |
| Chr12.56482313; C.A | ERBB3_chr12_56482341 |
| Chr12.56478847; C.A | ERBB3_chr12_56478854 |
| Chr12.56478856; G.T | ERBB3_chr12_56478854 |
| Chr6.152419949; GC.G | ESR1_chr6_152419923 |
| Chr12.56492643; A.AG | ERBB3_chr12_56492633 |
| Chr12.56481952; T.TC | ERBB3_chr12_56481922 |

TABLE 6

(See FIG. 4B):

| Variants detected with base changes: | Amplicon identification: |
|---|---|
| Chr17.7578279; AG.A | TP53_chr17_7578268 |
| Chr7.55259452; AC.A | EGFR_chr7_55259485 |
| Chr17.7578467; T.TG | TP53_chr17_7578479 |
| Chr6.152332875; GC.G | ESR1_chr6_152332832 |
| Chr6.152419915; G.GC | ESR1_chr6_152419923 |
| Chr3.178952100; C.CA | PIK3CA_SP_28.120542 |
| Chr17.7578480; T.TC | TP53_chr17_7578479 |
| Chr7.55259533; C.T | EGFR_chr7_55259485 |
| Chr7.55259486; G.A | EGFR_chr7_55259485 |
| Chr4.153245400; C.A | FBXW7_chr4_153245446 |
| Chr7.55259458; C.A | EGFR_chr7_55259485 |
| Chr17.7578403; C.A | TP53_chr17_7578403 (p.Cys176Phe) |
| Chr3.178928074; G.T | PIK3CA_chr3_178928079 |
| Chr17.7578388; C.A | TP53_chr17_7578403 |
| Ch17.7577148; G.T | TP53_chr17_7577118 |
| Chr17.7578386; A.AG | TP53_chr17_7578403 |
| Chr17.7578388; C.CG | TP53_chr17_7578403 |

TABLE 6-continued (See FIG. 4B):

| Variants detected with base changes: | Amplicon identification: |
|---|---|
| Chr17.7577091; G.GA | TP53_chr17_7577118 |
| Chr14.105246538; G.GC | AKT1_chr14_105246551 |
| Chr17.7578394; T.TG | TP53_chr17_7578403 |
| Chr3.178938927; G.GA | PIK3CA_chr3_178938934 |
| Chr3.178927964; GT.G | PIK3CA_chr3_178927980 |
| Chr12.56492643; A.AG | ERBB3_chr12_56492633 |
| Chr3.178938897; T.TA | PIK3CA_chr3_178938934 |
| Chr3.178927977; C.CT | PIK3CA_chr3_178927980 |
| Chr6.152419949; GC.G | ESR1-chr6_152419923 |

TABLE 7

(See FIG. 5A):

| Variants detected with base changes: | Amplicon identification: |
|---|---|
| Chr17.7578420; C.CG | SP_13.459207 |
| Chr17.7578474; CG.C | SP_13.459207 |
| Chr7.55259446; AC.A | EGFR_chr7_55259485 (SYS_ERR) |
| Chr2.29445315; T.TG | SP_22.1279 |
| Chr7.55249008; T.TC | SP_34.238517 |
| Chr3.178936094; C.A | SP_27.58329 |
| Chr3.178952087; C.A | SP_28.120542 |
| Chr7.55259490; C.A | EGFR_chr7_55259485 |
| Chr7.55241703; G.T | SP_32.90482 |
| Chr17.7577539; G.T | TP53_chr17_7577548 |
| Chr2.29436847; C.A | SP_20.17292 |
| Chr17.7578458; G.A | SP_13.459207 |
| Chr7.55259452; AC.A | EGFR_chr7_55259485 |
| Chr7.55249061; C.A | SP_34.342338 |
| Chr7.55249001; G.T | SP_34.238517 |
| Chr7.55242493; G.T | SP_33.185537 |
| Chr7.140481414; G.T | SP_41.257210 |
| Chr7.116423407; G.T | SP_39.150176 |
| Chr3.178952094; G.T | SP_28.120542 |
| Chr2.29445464; G.T | SP_22.347670 |
| Chr2.29445448; C.A | SP_22.347670 |
| Chr2.29445446; C.A | SP_22.347670 |
| Chr2.29445195; T.TG | SP_22.103754 |
| Chr2.29445186; G.T | SP_22.103754 |
| Chr2.29443676; G.T | SP_21.316843 |
| Chr2.29443675; C.A | SP_21.316843 |
| Chr2.29443617; C.A | SP_21.253043 |
| Chr2.29432692; C.A | SP_19.139310 |
| Chr2.29432668; C.A | SP_19.139310 |
| Chr17.7579301; G.T | SP_14.132920 |
| Chr17.7579294; C.A | SP_14.132920 |
| Chr17.7578448; G.T | SP_13.459207 |
| Chr17.7577131; G.T | SP_12.465452 |
| Chr17.7577122; C.A | SP_12.465452 |
| Chr17.7577091; G.T | SP_12.465452 |
| Chr17.7574018; G.T | SP_11.83369 |
| Chr15.66774140; C.A | SP_9.104576 |
| Chr15.66774120; AC.A | SP_9.104576 |
| Chr15.66729150; G.T | SP_8.178049 |
| Chr15.66727448; C.T | SP_7.208631 |
| Chr1.115256535; G.T | SP_1.225761 |
| Chr15.66727438; G.T | SP_7.208631 |
| Chr7.55259533; C.T | EGFR_chr7_55259485 |
| Chr7.55259532; G.T | EGFR_chr7_55259485 |
| Chr7.55259514; C.A | EGFR_chr7_55259485 |
| Chr7.55259498; G.T | EGFR_chr7_55259485 |
| Chr7.55259477; G.A | EGFR_chr7_55259485 |
| Chr7.55259450; C.A | EGFR_chr7_55259485 |
| Chr7.55249019; C.A | SP_34.238517 |
| Chr7.116412061; G.A | SP_37.22932 |
| Chr7.116412028; G.T | SP_37.22932 |
| Chr17.7578468; G.T | SP_13.459207 |
| Chr17.7578455; C.A | SP_13.459207 |
| Chr17.7578406; C.A | SP_13.459207 |
| Chr17.7578245; G.A | TP53_chr17_7578208 |

TABLE 7-continued (See FIG. 5A):

| Variants detected with base changes: | Amplicon identification: |
|---|---|
| Chr17.7578185; G.T | TP53_chr17_7578208 |
| Chr17.7578240; C.A | TP53_chr17_7578208 |
| Chr1.115256507; T.C | SP_1.225761 |
| Chr2.29443675; C.T | SP_21.316843 |
| Chr7.55259472; C.T | EGFR_chr7_55259485 |
| Chr7.55259450; C.T. | EGFR_chr7_55259485 |
| Chr17.7578408; C.T | SP_13.459207 |
| Chr7.116412025; C.T | SP_37.22932 |
| Chr2.29445187; A.AG | SP_22.103754 |
| Chr17.37880983; C.A | SP_15.175577 |
| Chr7.116412052; C.A | SP_37.22932 |
| Chr6.117641128; C.A | SP_30.260736 |
| Chr17.7578195; C.A | TP53_chr17_7578208 |
| Chr17.7579303; G.T | SP_14.132920 |
| Chr7.55259489; G.T | EGFR_chr7_55259485 |
| Chr7.55259486; G.T | EGFR_chr7_55259485 |
| Chr7.55249089; G.T | SP_34.342338 |
| Chr7.55242457; G.T | SP_33.185537 |
| Chr7.140453127; C.G | BRAF_chr7_140453146 |
| Chr7.140453104; C.A | BRAF_chr7_140453146 |
| Chr7.116417445; C.A | SP_38.10493 |
| Chr6.117641120; G.T | SP_30.260736 (p.L1951M) |
| Chr2.29445443; C.A | SP_22.347670 |
| Chr2.29445289; G.T | SP_22.1279 |
| Chr2.29445280; C.A | SP_22.1279 |
| Chr2.29436864; G.T | SP_20.17292 |
| Chr2.29436854; G.T | SP_20.17292 |
| Chr17.7579308; T.TC | SP_14.132920 |
| Chr17.37881005; C.T | SP_15.175577 |
| Chr15.66774131; G.T | SP_9.104576 |
| Chr15.66727424; G.T | SP_7.208631 |
| Chr12.25380277; G.T | SP_4.215017 |
| Chr12.25398274; G.T | SP_5.288759 |
| Chr12.25398276; C.T | SP_5.288759 |
| Chr12.25398282; C.T | SP_5.288759 |
| Chr2.29445199; T.TG | SP_22.103754 |
| Chr2.29445196; C.CG | SP_22.103754 |
| Chr3.178936068; G.T | SP_27.58329 |
| Chr3.178936092; A.C | SP_27.58329 |
| Chr15.66729146; G.T | SP_8.178049 |

TABLE 8

(See FIG. 5B):

| Variants detected with base changes: | Amplicon identification: |
|---|---|
| Chr17.7578474; CG.C | SP_13.459207 |
| Chr17.7578420; C.CG | SP_13.459207 |
| Chr7.55241701; G.GA | SP_32.90482 |
| Chr2.29445485; A.AC | SP_22.347670 |
| Chr7.55249008; T.TC | SP_34.238517 |
| Chr2.29445315; T.TG | SP_22.1279 |
| Chr2.29445187; A.AG | SP_22.103754 |
| Chr2.29445312; C.CG | SP_22.1279 |
| Chr2.29445199; T.TG | SP_22.103754 |
| Chr7.55259452; AC.A | EGFR_chr7_55259485 |
| Chr2.29445196; C.CG | SP_22.103754 |
| Chr2.29443621.A.AC | SP_21.253043 |
| Chr7.116417455; G.GT | SP_38.10493 |
| Chr17.7579308; T.TC | SP_14.132920 |
| Chr2.29445195; T.TG | SP_22.103754 |
| Chr7.55241677; GA.G | SP_32.90482 |
| Chr15.66729172; TG.T | SP_8.178049 |
| Chr1.115255520; T.A | SP_1.225761 |
| Chr7.55249084; C.A | SP_34.342338 |
| Chr7.55259525; G.T | EGFR_chr7_55259485 |
| Chr7.55259474; G.T | EGFR_chr7_55259485 |
| Chr7.55249087; C.A | SP_34.342338 |
| Chr7.55249006; C.A | SP_34.238517 |
| Chr7.55249005; G.T | SP_34.238517 (p.S768I) |

TABLE 8-continued (See FIG. 5B):

| Variants detected with base changes: | Amplicon identification: |
|---|---|
| Chr7.55242454; G.A | SP_33.185537 |
| Chr7.140453135; C.A | BRAF_chr7_140453146 |
| Chr7.140453127; C.T | BRAF_chr7_140453146 |
| Chr7.140453123; C.A | BRAF_chr7_140453146 |
| Chr7.140453108; C.A | BRAF_chr7_140453146 |
| Chr2.29445321; G.T | SP_22.1279 |
| Chr2.29445277; G.T | SP_22.1279 |
| Chr2.29445272; C.A | SP_22.1279 |
| Chr2.29445265; C.A | SP_22.1279 |
| Chr2.29445218; C.A | SP_22.103754 |
| Chr2.29445203; G.T | SP_22.103754 |
| Chr2.29445186; G.T | SP_22.103754 |
| Chr2.29436849; C.T | SP_20.17292 |
| Chr2.29436830; G.T | SP_20.17292 |
| Chr17.7578458; G.A | SP_13.459207 |
| Chr17.7578212; G.T | TP53_chr17_7578208 |
| Chr17.7578179; C.A | TP53_chr17_7578208 |
| Chr17.7577570; C.A | TP53_chr17_7577548 |
| Chr17.7577539; G.T | TP53_chr17_7577548 |
| Chr17.7577525; G.C | TP53_chr17_7577548 |
| Chr17.7577522; G.A | TP53_chr17_7577548 |
| Chr17.7577139; G.A | SP_12.465452 |
| Chr17.7577102; C.A | SP_12.465452 |
| Chr17.7577091; G.T | SP_12.465452 |
| Chr17.7577094; G.A | SP_12.465452 (p.R282W) |
| Chr7.55249029; G.T | SP_34.238517 |
| Chr7.55242469; T.C | SP_33.185537 |
| Chr7.55242456; C.A | SP_33.185537 |
| Chr7.55241703; G.T | SP_32.90482 |
| Chr7.55241697; C.A | SP_32.90482 |
| Chr7.140481403; C.A | SP_41.257210 |
| Chr7.140453143; C.A | BRAF_chr7_140453146 |
| Chr7.116417444; G.T | SP_38.10493 |
| Chr6.117641121; C.A | SP_30.260736 |
| Chr2.29445318; G.T | SP_22.1279 |
| Chr2.29445280; C.A | SP_22.1279 |
| Chr2.29443631; G.T | SP_21.253043 (p.L1196M) |
| Chr2.29443626; C.A | SP_21.253043 |
| Chr17.7574024; G.T | SP_11.83369 |
| Chr17.37880994; G.T | SP_15.175577 |
| Chr15.66774146; G.T | SP_9.104576 |
| Chr15.66774133; G.T | SP_9.104576 |
| Chr1.115258738; C.A | NRAS_chr1_115258747 |
| Chr1.115258748; C.A | NRAS_chr1_115258747 (p.G12C) |
| Chr15.66774130; G.A | SP_9.104576 |
| Chr7.55259468; C.T | EGFR_chr7_55259485 |
| Chr1.115256540; A.AG | SP_1.225761 |
| Chr15.66727423; C.T | SP_7.208631 |
| Chr1.115256532; C.A | SP_1.225761 |
| Chr7.55259486; G.T | EGFR_chr7_55259485 |
| Chr7.55259485; C.A | EGFR_chr7_55259485 (SYS_ERR) |
| Chr7.55259445; C.A | EGFR_chr7_55259485 |
| Chr7.55249100; G.T | SP_34.342338 |
| Chr7.55248997; G.T | SP_34.238517 |
| Chr7.55241694; G.T | SP_32.90482 |
| Chr7.116423407; G.T | SP_39.150176 |
| Chr7.116417451; G.T | SP_38.10493 |
| Chr7.116412025; C.A | SP_37.22932 |
| Chr6.117641132; G.T | SP_30.260736 |
| Chr6.117641129; G.A | SP_30.260736 |
| Chr3.178952097; G.T | SP_28.120542 |
| Chr2.29445465; C.A | SP_22.347670 |
| Chr2.29445449; C.T | SP_22.347670 |
| Chr2.29445434; G.T | SP_22.347670 |
| Chr2.29445311; G.T | SP_22.1279 |
| Chr2.29445305; G.T | SP_22.1279 |
| Chr2.29445293; G.T | SP_22.1279 |
| Chr2.29445271; G.T | SP_22.1279 |
| Chr2.29443595; G.T | SP_21.253043 |
| Chr2.29432692; C.A | SP_19.139310 |
| Chr17.7578438; C.A | SP_13.459207 |
| Chr17.7577120; C.A | SP_12.465452 (p.R273L) |
| Chr17.7574037; C.A | SP_11.83369 |
| Chr17.37881005; C.A | SP_15.175577 |
| Chr17.37880983; C.A | SP_15.175577 |
| Chr15.66729170; C.A | SP_8.178049 |
| Chr15.66729158; C.A | SP_8.178049 |
| Chr15.66727456; C.A | SP_7.208631 |
| Chr1.115256519; G.T | SP_1.225761 |
| Chr12.25398275; C.A | SP_5.288759 |
| Chr17.7577137; C.A | SP_12.465452 |
| Chr2.29445310; G.T | SP_22.1279 |
| Chr7.55259526; C.A | EGFR_chr7_55259485 |
| Chr7.55259514; C.A | EGFR_chr7_55259485 |
| Chr7.55259464; G.C | EGFR_chr7_55259485 |
| Chr7.116423404; C.A | SP_39.150176 |
| Chr3.178952098; G.A | SP_28.120542 |
| Chr3.178952094; G.T | SP_28.120542 |
| Chr2.29443705; C.G | SP_21.316843 |
| Chr2.29443676; G.T | SP_21.316843 |
| Chr17.7579311; C.A | SP_14.132920 |
| Chr17.7579295; C.A | SP_14.132920 |
| Chr17.7578205; C.A | TP53_chr17_7578208 |
| Chr17.7577121; G.A | SP_12.465452 (p.R273C) |
| Chr17.7577101; C.A | SP_12.465452 |
| Chr1.115258732; C.A | NRAS_chr1_115258747 |
| Chr17.7574023; C.A | SP_11.63369 |
| Chr17.7578462; G.A | SP_13.459207 |
| Chr7.140453130; G.GC | BRAF_chr7_140453146 |
| Chr7.140453127; C.CG | BRAF_chr7_140453146 |
| Chr7.140453119; C.CA | BRAF_chr7_140453146 |
| Chr17.7577133; T.C | SP_12.465452 |
| Chr17.7577140; T.A | SP_12.465452 |
| Chr7.55259446; AC.A | EGFR_chr7_55259485 (SYS_ERR) |
| Chr2.29445273; G.T | SP_22.1279 |
| Chr17.7577592; G.A | TP53_chr17_7577548 |
| Chr17.7578244; C.T | TP53_chr17_7578208 |
| Chr15.66729146; G.T | SP_8.178049 |
| Chr3.178936092; A.C | SP_27.58329 |
| Chr12.25398282; C.T | SP_5.288759 |
| Chr12.25398276; C.T | SP_5.288759 |

TABLE 9

(See FIG. 6A):

Variants detected with base changes:

Chr6.152419949; GC.G
Chr7.55259452; AC.A
Chr12.56492643; A.AG
Chr3.178938897; T.TA
Chr17.7578467; T.TG
Chr3.178938927; G.GA
Chr3.178927964; GT.G
Chr12.56481952; T.TC
Chr17.7578388; C.CG
Chr14.105246538; G.GC

TABLE 9-continued (See FIG. 6A):

Variants detected with
base changes:

Chr17.7578394; T.TG
Chr12.56492647; C.A
Chr3.178921563; C.A
Chr12.56492658; C.A
Chr6.152415524; G.T
Chr6.152419915; G.GC
Chr17.7578195; C.A
Chr3.178952100; C.CA
Chr12.25398287; G.T
Chr12.56481945; C.A
Chr12.56482337; G.T
Chr14.105246526; C.A
Chr14.105246533; G.T
Chr17.7577091; G.GA
Chr17.7577519; G.T
Chr17.7578183; C.A
Chr17.7578389; G.T
Chr17.7578403; C.A
Chr3.178928074; G.T
Chr3.178928088; C.A
Chr3.178952098; G.T
Chr7.55259461; C.A
Chr17.7577111; G.T
Chr17.7577141; C.A
Chr17.7577148; G.T
Chr17.7577156; C.A
Chr17.7577534; C.A
Chr17.7577539; G.T
Chr17.7577573; G.T
Chr17.7578386; A.AG
Chr17.7578388; C.A
Chr17.7578470; C.T
Chr17.7578480; T.TC
Chr17.7578507; G.T
Chr17.7578508; C.A

TABLE 10

(See FIG. 6B):

| Variants detected with base changes: | Amplicon identification: |
|---|---|
| Chr17.7578279; AG.A | TP53_chr17_7578268 |
| Chr3.178927977; C.CT | PIK3CA_chr3_178927980 |
| Chr6.152419949; GC.G | ESR1_chr6_152419923 |
| Chr7.55259452; AC.A | EGFR_chr7_55259485 |
| Chr12.56492643; A.AG | ERBB3_chr12_56492633 |
| Chr3.178938897; T.TA | PIK3CA_chr3_178938934 |
| Chr17.7578467; T.TG | TP53_chr17_7578479 |
| Chr3.178938927; G.GA | PIK3CA_chr3_178938934 |
| Chr3.178927964; GT.G | PIK3CA_chr3_178927980 |
| Chr12.56481952; T.TC | ERBB3_chr12_56481922 |
| Chr17.7578388; C.CG | TP53_chr17_7578403 |
| Chr14.105246538; G.GC | AKT1_chr14_105246551 |
| Chr17.7578394; T.TG | TP53_chr17_7578403 |
| Chr12.56492647; C.A | ERBB3_chr12_56492633 |
| Chr3.178921563; C.A | PIK3CA_chr3_178921553 |
| Chr12.56492658; C.A | ERBB3_chr12_56492633 |
| Chr6.152415524; G.T | ESR1_chr6_152415537 |
| Chr6.152419915; G.GC | ESR1_chr6_152419923 |
| Chr17.7578195; C.A | TP53_chr17_7578211 |
| Chr3.178952100; C.CA | PIK3CA_SP_28.120542 |
| Chr12.25398287; G.T | KRAS_SP_5.288759 |
| Chr12.56481945; C.A | ERBB3_chr12_56481922 |

TABLE 10-continued (See FIG. 6B):

| Variants detected with base changes: | Amplicon identification: |
|---|---|
| Chr12.56482337; G.T | ERBB3_chr12_56482341 |
| Chr14.105246526; C.A | AKT1_chr14_105246551 |
| Chr14.105246533; G.T | AKT1_chr14_015246551 |
| Chr17.7577091; G.GA | TP53_chr17_7577118 |
| Chr17.7577519; G.T | TP53_chr17_7577547 |
| Chr17.7578183; C.A | TP53_chr17_7578211 |
| Chr17.7578389; G.T | TP53_chr17_7578403 |
| Chr17.7578403; C.A | TP53_chr17_7578403 (p.Cys176Phe) |
| Chr3.178928074; G.T | PIK3CA_chr3_178928079 |
| Chr3.178928088; C.A | PIK3CA_chr3_178928079 |
| Chr3.178952098; G.T | PIK3CA_SP_28.120542 |
| Chr7.55259461; C.A | EGFR_chr7_55259485 |
| Chr17.7577111; G.T | TP53_chr17_7577118 |
| Chr17.7577141; C.A | TP53_chr17_7577118 (p.Gly266Val) |
| Chr17.7577148; G.T | TP53_chr17_7577118 |
| Chr17.7577156; C.A | TP53_chr17_7577118 |
| Chr17.7577534; C.A | TP53_chr17_7577547 (p.Arg249Ser) |
| Chr17.7577539; G.T | TP53_chr17_7577547 |
| Chr17.7577573; G.T | TP53_chr17_7577547 |
| Chr17.7578386; A.AG | TP53_chr17_7578403 |
| Chr17.7578388; C.A | TP53_chr17_7578403 |
| Chr17.7578470; C.T | TP53_chr17_7578479 |
| Chr17.7578480; T.TC | TP53_chr17_7578479 |
| Chr17.7578507; G.T | TP53_chr17_7578479 |
| Chr17.7578508; C.A | TP53_chr17_7578479 |
| Chr3.178921548; G.T | PIK3CA_chr3_178921553 |
| Chr3.178921564; G.T | PIK3CA_chr3_178921553 |
| Chr3.178927950; G.T | PIK3CA_chr3_178927980 |
| Chr4.153245450; G.T | FBXW7_chr4_153245446 |
| Chr6.152332875; GC.G | ESR1_chr6_152332832 |
| Chr7.55259451; G.T | EGFR_chr7_55259485 |
| Chr4.153245400; C.A | FBXW7_chr4_153245446 |
| Chr7.55259445; C.A | EGFR_chr7_55259485 |
| Chr7.55259446.AC.A | EGFR_chr7_55259485 (SYS_ERR) |
| Chr7.55259448; C.A | EGFR_chr7_55259485 |
| Chr7.55259448; C.G | EGFR_chr7_55259485 |
| Chr7.55259448; C.T | EGFR_chr7_55259485 |
| Chr7.55259458; C.A | EGFR_chr7_55259485 |
| Chr7.55259475; G.T | EGFR_chr7_55259485 |
| Chr7.55259486; G.A | EGFR_chr7_55259485 |
| Chr7.55259487; C.A | EGFR_chr7_55259485 |
| Chr7.55259513; G.T | EGFR_chr7_55259485 |
| Chr7.55259525; G.T | EGFR_chr7_55259485 |
| Chr7.55259533; C.T | EGFR_chr7_55259485 |

What is claimed:

1. A method, comprising,
providing a single reaction mixture containing (i) a first plurality of polynucleotides, (ii) at least one nucleic acid damage-mitigating reagent, and optionally (iii) at least one chelating reagent; and
fragmenting the first plurality of polynucleotides to generate a plurality of nucleic acid fragments from the first plurality of polynucleotides,
wherein the at least one nucleic acid damage-mitigating reagent is selected from a group consisting of 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; and indole-3-acetic acid.

2. A method, comprising,
providing a first single reaction mixture containing (i) a first plurality of polynucleotides, (ii) at least one nucleic acid damage-mitigating reagent, and (iii) at least one chelating reagent;
fragmenting the first plurality of polynucleotides to generate a first plurality of nucleic acid fragments having reduced damage compared to a plurality of polynucleotides that are fragmented in the absence of the nucleic acid damage-mitigating reagent and the chelating reagent;
optionally providing a second single reaction mixture containing (i) a second plurality of polynucleotides, (ii) the at least one nucleic acid damage-mitigating reagent, and (iii) the at least one chelating reagent; and
optionally fragmenting the second plurality of polynucleotides to generate a second plurality of nucleic acid fragments having reduced damage compared to a plurality of polynucleotides that are fragmented in the absence of the nucleic acid damage-mitigating reagent and the chelating reagent,
wherein the at least one nucleic acid damage-mitigating reagent is selected from a group consisting of 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; and indole-3-acetic acid.

3. The method of claim 1, wherein the damage-mitigating reagent is 3 indole-propionic acid.

4. The method of claim 1, wherein the chelating reagent is selected from an aminopolycarboxlic acid and a phosphonic acid.

5. The method of claim 4, wherein the chelating reagent is selected from a group consisting of EDTA, EDDHA, EDDS, EDTMP and EGTA.

6. The method of claim 1 wherein the nucleic acid fragments have a reduced number of any one or any combination of nucleic acid transitions C>T, T>C, A>G, and G>A and/or nucleic acid transversions A>T, T>A, C>T, T>C, A>C, C>A, G>T and T>G, compared to the nucleic acid fragments that have been fragmented in the absence of the nucleic acid damage-mitigating reagent and the chelating reagent.

7. The method of claim 1 wherein (i) the reduced damage of the first plurality of nucleic acid fragments and the second plurality of nucleic acid fragments comprises reduced transitions which are selected from a group consisting of C>T, T>C, A>G, and G>A, and wherein (ii) the reduced damage of the first plurality of nucleic acid fragments and the second plurality of nucleic acid fragments comprises reduced transversions which are selected from a group consisting of, A>T, T>A, C>T, T>C, A>C, C>A, G>T and T>G.

8. The method of claim 1 wherein the fragmenting is conducted with mechanical force which comprises: acoustic force, nebulizing force, sonication force, cavitation force or shearing force.

9. The method of claim 1, wherein the plurality of polynucleotides comprise DNA or RNA or a combination of DNA/RNA.

10. The method of claim 9, wherein the first plurality of polynucleotides comprise DNA or RNA, and wherein the second plurality of polynucleotides comprise DNA or RNA.

11. The method of claim 2, further comprising mixing together the first plurality of nucleic acid fragments and the second plurality of nucleic acid fragments to form a mixture of fragmented nucleic acids.

12. The method of claim 11, wherein mixture of fragmented nucleic acids comprises a known amount of at least one wild-type target sequence and/or at least one variant target sequence from the first plurality of nucleic fragments.

13. The method of claim 11, wherein mixture of fragmented nucleic acids comprises a known amount of at least one wild-type target sequence and/or at least one variant target sequence from the second plurality of nucleic fragments.

14. The method of claim 1, further comprising joining one end or both ends of the first plurality of nucleic acid fragments and/or the second plurality of nucleic acid fragments to an oligonucleotide adaptor to generate adaptor-joined nucleic acid fragments, wherein the adaptor-joining is performed by ligation or primer extension or PCR amplification.

15. The method of claim 14, further comprising amplifying the adaptor-joined nucleic acid fragments to generate nucleic acid amplicons.

16. The method of claim 15, further comprising sequencing the nucleic acid amplicons.

17. The method of claim 16, wherein the sequencing generates no more than 10 false positive sequencing reads which comprise,
fragmentation-induced nucleic acid transitions which are selected from a group consisting of C>T, T>C, A>G, and G>A; and/or
transversions which are selected from a group consisting of, A>T, T>A, C>T, T>C, A>C, C>A, G>T and T>G.

18. The method of claim 16, wherein the sequencing comprises:
depositing the adaptor-joined nucleic acids fragments, or the nucleic acid amplicons, onto an array of reaction chambers, wherein at least one reaction chamber is capacitively coupled to a field effect transistor (FET) that detects byproducts of nucleotide incorporations;
contacting the adaptor-joined nucleic acid fragments, or the nucleic acid amplicons with a plurality of polymerases;
flowing a plurality of nucleotides onto the array of reaction chambers under conditions suitable for nucleotide incorporation, wherein the plurality of nucleotides comprises at least one type of un-labeled non-terminator nucleotide;
detecting incorporation of the at least one type of un-labeled non-terminator nucleotide by detecting byproducts of nucleotide incorporation; and
identifying the incorporated un-labeled non-terminator nucleotide.

19. A composition comprising nucleic acid prepared according to the method of claim 1.

20. A kit comprising the composition of claim 19.

21. A kit for carrying out the method according to claim 1, comprising, a first plurality of polynucleotides; and
at least one nucleic acid damage-mitigating reagent selected from a group consisting of 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; and indole-3-acetic acid; and
optionally at least one chelating reagent.

22. A system for carrying out the method according to claim 1, comprising,
a first plurality of polynucleotides, and
at least one nucleic acid damage-mitigating reagent selected from a group consisting of 3-indole-propionic acid; phenylacetic acid; DL-indole-3-lactic acid; 1-methyl-2-oxindole; indole-3-pyruvic acid; indole-3-carboxylic acid; 3-indoleacrylic acid; N-(3-indolylacetyle)-L-alanine; indole lactic acid; and indole-3-acetic acid, and
optionally at least one chelating reagent; and
a device for fragmenting nucleic acids.

* * * * *